United States Patent
Xin et al.

(10) Patent No.: US 9,416,173 B2
(45) Date of Patent: Aug. 16, 2016

(54) PEPTIDE AND CONJUGATE VACCINES FOR FUNGAL INFECTIONS

(75) Inventors: Hong Xin, Marrero, LA (US); Jim E. Cutler, Minneapolis, MN (US)

(73) Assignee: Board of Supervisors of Louisiana State University And Agricultural and Mechanical College, Baton Rouge, LA (US)

(*) Notice: Subject to any disclaimer, the term of this patent is extended or adjusted under 35 U.S.C. 154(b) by 0 days.

(21) Appl. No.: 14/112,561

(22) PCT Filed: Apr. 20, 2012

(86) PCT No.: PCT/US2012/034511
§ 371 (c)(1),
(2), (4) Date: Oct. 18, 2013

(87) PCT Pub. No.: WO2012/145666
PCT Pub. Date: Oct. 26, 2012

(65) Prior Publication Data
US 2014/0037641 A1 Feb. 6, 2014

Related U.S. Application Data

(60) Provisional application No. 61/477,738, filed on Apr. 21, 2011.

(51) Int. Cl.
*A61K 39/00* (2006.01)
*C07K 16/14* (2006.01)
(Continued)

(52) U.S. Cl.
CPC ............ *C07K 16/14* (2013.01); *A61K 39/0002* (2013.01); *A61K 47/4833* (2013.01); *A61K 47/48261* (2013.01); *C07K 14/40* (2013.01); *C07K 16/40* (2013.01);
(Continued)

(58) Field of Classification Search
CPC ........................................ A61K 39/00
USPC ................. 530/388.1; 424/133.1, 130.1
See application file for complete search history.

(56) References Cited

U.S. PATENT DOCUMENTS

| 4,771,127 A | 9/1988 | Cryz | 530/395 |
| 5,578,309 A | 11/1996 | Cutler | 424/274.1 |

(Continued)

FOREIGN PATENT DOCUMENTS

| WO | WO 03/090787 | 6/2003 |
| WO | 2005/060713 | * 7/2005 |

(Continued)

OTHER PUBLICATIONS

Xin et al, PNAS, Sep. 9, 2008, vol. 105, No. 36, pp. 13526-13531 and supplemental material, Synthetic glycopeptide vaccines combining B-mannan and peptide epitopes induce protection against candidiasis.*

(Continued)

*Primary Examiner* — Albert Navarro
*Assistant Examiner* — Ginny Portner

(57) ABSTRACT

Several new peptides have been developed that show effectiveness as vaccines against candidiasis and other fungal diseases. A new conjugate vaccine of a β-mannotriose linked to a fungal peptide linked to tetanus toxin has been shown to be effective as a vaccine with or without use of an adjuvant. In addition, a monoclonal antibody has been identified that offers protection from a *Candida* infection.

6 Claims, 48 Drawing Sheets

(51) Int. Cl.
    *C07K 14/40*     (2006.01)
    *C07K 16/40*     (2006.01)
    *A61K 47/48*     (2006.01)

(52) U.S. Cl.
    CPC .. *A61K 2039/505* (2013.01); *A61K 2039/5158* (2013.01); *A61K 2039/55505* (2013.01); *A61K 2039/55566* (2013.01); *A61K 2039/55572* (2013.01); *A61K 2039/6037* (2013.01); *C07K 2319/00* (2013.01)

(56) References Cited

U.S. PATENT DOCUMENTS

| | | | |
|---|---|---|---|
| 6,309,642 | B1 | 10/2001 | Cutler .................... 424/185.1 |
| 6,391,587 | B1 | 5/2002 | Cutler .................... 424/184.1 |
| 6,403,090 | B1 | 6/2002 | Cutler .................... 424/152.1 |
| 6,488,929 | B2 | 12/2002 | Cutler .................... 424/184.1 |
| 6,630,146 | B2 | 10/2003 | Cutler .................... 424/184.1 |
| 6,747,137 | B1* | 6/2004 | Weinstock ........... C12Q 1/6895 435/6.13 |
| 6,849,419 | B1* | 2/2005 | Wakasugi et al. ............ 435/7.32 |
| 7,052,915 | B2* | 5/2006 | Aebersold .............. C07K 1/107 435/7.5 |
| 7,067,138 | B1 | 6/2006 | Edwards et al. ............... 424/274 |
| 7,122,320 | B2* | 10/2006 | Reiter .................. C07K 16/121 435/7.1 |
| 7,722,890 | B2 | 5/2010 | Bundle ....................... 424/274.1 |
| 8,092,800 | B2* | 1/2012 | Cassone ................ C07K 16/14 424/130.1 |
| 2002/0054886 | A1 | 5/2002 | Cutler .................... 424/234.1 |
| 2003/0072775 | A1 | 4/2003 | Cutler .................... 424/130.1 |
| 2003/0087283 | A1* | 5/2003 | Koopmann et al. ............... 435/6 |
| 2003/0124134 | A1 | 7/2003 | Edwards ................... 424/184.1 |
| 2004/0023316 | A1* | 2/2004 | Reiter et al. ................ 435/7.32 |
| 2005/0019931 | A1* | 1/2005 | Roemer ............... C12N 15/815 435/483 |
| 2006/0058506 | A1 | 3/2006 | Bundle ....................... 424/274.1 |
| 2006/0211085 | A1* | 9/2006 | Bobrowicz ............ C07K 14/39 435/69.1 |
| 2008/0193481 | A1 | 8/2008 | Bundle ......................... 514/124 |
| 2010/0119533 | A1* | 5/2010 | Clancy .................. C07K 14/40 424/185.1 |
| 2010/0209448 | A1 | 8/2010 | Bundle ...................... 424/274.1 |
| 2012/0093836 | A1* | 4/2012 | Hernando Echevarria ............. A61K 31/00 424/172.1 |
| 2014/0004538 | A1* | 1/2014 | Damiens .......... G01N 33/56961 435/7.31 |

FOREIGN PATENT DOCUMENTS

| | | |
|---|---|---|
| WO | WO 2006/096970 | 9/2006 |
| WO | WO 2006/121895 | 11/2006 |
| WO | 2008/109833 | * 9/2008 ............. C07K 14/00 |
| WO | WO 2008/109833 | 9/2008 |

OTHER PUBLICATIONS

Pitarch, A et al, Proteomics, 2001, vol. 1, pp. 550-559, Analysis of the serologic response to systemic Candida albicans infection in a murine model.*

Xin, Hong et al, Synthetic glycopeptide vaccines combining B-mannan and peptide epitopes induce protection against candidiasis.*

Han, Yongmoon, International Immunopharmacology, vol. 10, 2010, pp. 1526-1531, Efficacy of combination immunotherapy of IgM MAb B6.1 and amphotericin B against disseminated candidiasis.*

Han, Y et al, Infection and Immunity, Mar. 2000, vol. 68(3), pp. 1649-1654, Protection against Candidiasis by an Immunoglobulin G3 (IgG3) Monoclonal Antibody Specific for the Same Mannotriose as an IgM Protective Antibody.*

Cassone, A. et al., "An outline of the role of anti-Candida antibodies within the context of passive immunization and protection from candidiasis," Curr.Mol.Med., vol. 5, pp. 377-382 (2005).

Cutler, J. E., "Defining criteria for anti-mannan antibodies to protect against candidiasis," Curr.Mol.Med., vol. 5, pp. 383-392 (2005).

Cutler, J. E. et al., "Advances in combating fungal diseases: Vaccines on the threshold," Nat.Rev.Microbiol., vol. 5, pp. 13-28 (2007).

De Bernardis, F., M. et al., "Protective role of antimannan and anti-aspartyl proteinase antibodies in an experimental model of Candida albicans vaginitis in rats," Infect.Immun., vol. 65, pp. 3399-3405 (1997).

Eggimann, P. et al., "Epidemiology of *Candida* species infections in critically ill non-immunosuppressed patients," Lancet Infect.Dis, vol. 3, pp. 685-702 (2003).

Han, Y. 2010. Efficacy of combination immunotherapy of IgM MAb B6.1 and amphotericin B against disseminated candidiasis, Int.Immunopharmacol., vol. 10, pp. 1526-1531 (2010).

Horn, D. L. et al., "Epidemiology and outcomes of candidemia in 2019 patients: data from the prospective antifungal therapy alliance registry," Clin.Infect.Dis., vol. 48, pp. 1695-1703 (2009).

Hsu, F. C. et al., "Prognostic factors for patients with culture-positive Candida infection undergoing abdominal surgery," J.Microbiol.Immunol.Infect., vol. 42, pp. 378-384 (2009).

Jarvis, W. R. et al., "Predominant pathogens in hospital infections. J.Antimicrob.Chemother," vol. 29, pp. 19-24 (1992).

Marsh, J.J. et al., "Fructose-bisphosphate aldolases: an evolutionary history," Trends Biochem.Sci., vol. 17, pp. 110-113 (1992).

Matthews, R. C. et al., "Preclinical assessment of the efficacy of mycograb, a human recombinant antibody against fungal HSP90," Antimicrob.Agents Chemother., vol. 47, pp. 2208-2216 (2003).

Mochon, A. B. et al., Is a vaccine needed against Candida albicans? Med.Mycol., vol. 43, pp. 97-115 (2005).

Nooney, L. M. et al., "Evaluation of Mycograb, amphotericin B, caspofungin, and fluconazole in combination against Cryptococcus neoformans by checkerboard and time-kill methodologies," Diagn. Microbiol.Infect.Dis., vol. 51, pp. 19-29 (2005).

Richards, M. J. et al., "Nosocomial infections in coronary care units in the United States," Am.J.Cardiol, vol. 82, pp. 789-793 (1998).

Rodaki, A. et al., "Effects of depleting the essential central metabolic enzyme fructose-1,6-bisphosphate aldolase on the growth and viability of Candida albicans: implications for antifungal drug target discovery," Eukaryot Cell, vol. 5, pp. 1371-1377 (2006).

Xin, H. et al., "Anti-candidasis synthetic glycopeptides vaccine with adjuvant can induce protective immunity in mice," an abstract for the 111th General Meeting of the American Society of Microbiology, New Orleans, Louisiana (May 20-24, 2011).

Xin, H. et al., "New strategies to present an anti-Candidiasis synthetic glycopeptides vaccine acceptable for human use," a poster presented at the Gordon Conference, Galveston, Texas (Jan. 2011).

Xin, H. et al., Self-adjuvanting glycopeptide conjugate vaccine against disseminated Candidiasis, accepted by PLoS (2012).

Xin, H. et al., "Synthetic glycopeptide vaccines combining b-mannan and peptide epitopes induce protection against candidiasis," Proc. Natl.Acad .Sci.USA, vol. 105, pp. 13526-13531 (2008).

Xin, H. et al., "Vaccine and monoclonal antibody that enhance mouse resistance to Candidiasis, Clinical and Vaccine Immunoogy," vol. 18, pp. 1656-1667 (2011, epub Aug. 10, 2011).

Yang, Q., L. et al., "Prophylactic vaccination with phage-displayed epitope of C. albicans elicits protective immune responses against systemic candidiasis in C57Bl/6 mice," Vaccine, vol. 23, pp. 4088-4096. (2005).

Casadevall, A. et al., "A reappraisal of humoral immunity based on mechanisms of antibody-mediated protection against intracellular pathogens," Advances in Immunology, vol. 91, pp. 1-44 (2006).

Bromuro, C. et al., "Interplay between protective and inhibitory antibodies dictates the outcome of experimentally disseminated candidiasis in recipients of a *Candida albicans* vaccine," Infection and Immunology, vol. 70, No. 10, pp. 5462-5470 (2002).

Cutler, J. et al., "Advances in combating fungal diseases: vaccines on the threshold," Nature Reviews Microbiology, vol. 5, No. 1, pp. 13-28 (2007).

Han, Y., "Efficacy of combination immunotherapy of IgM MAb B6.1 and amphotericin B against disseminated candidiasis," International Immunopharmacology., vol. 10, pp. 1526-1531 (2010).

(56) References Cited

OTHER PUBLICATIONS

Ibrahim, A. et al., "Vaccination with recombinant N-terminal domain of Als1p improves survival during murine disseminated candidiasis by enhancing cell-mediated, not humoral, immunity," Infection and Immunity, pp. 999-1005 (2005).

Mencacci, A. et al., "Defective antifungal T-helper (TH1) immunity in a murine model of allogeneic T-cell-depleted bone marrow transplantation and its restoration by treatment with TH2 cytokine antagonists," Blood Journal, vol. 97, No. 5, pp. 1483-1490 (2001).

Montagnoli, C. et al., "A role for antibodies in the generation of memory antifungal immunity," European Journal of Immunology., vol. 33, pp. 1193-1204 (2003).

Spellberg, B. et al., "Antibody titer threshold predicts anti-candidal vaccine efficacy even though the mechanism of protection is induction of cell-mediated immunity," Journal of Infectious Diseases., vol. 197, pp. 967-971 (2008).

Wang, H. et al., "Prediction of B-cell linear epitopes with a combination of support vector machine classification and amino acid propensity identification," Journal of Biomedicine and Biotechnology, Article ID 432830, pp. 1-12 (2011).

Wee, L. et al., "SVM-based prediction of linear B-cell epitopes using Bayes Feature Extraction," BMC Genomics, vol. 11, suppl. 4, pp. 1-9 (2010).

\* cited by examiner

Candida albicans strain: 3153A

Peptide 1:  YGKDVKDLFDYAQE
Peptide 2:  {NMe-Tyr}GKDVKDLFDYAQE
Peptide 3:  Y{NMe-Gly}KDVKDLFDYAQE
Peptide 4:  YG{Lys(Me)}DVKDLFDYAQE
Peptide 5:  YGKD{NMe-Val}KDLFDYAQE
Peptide 6:  YGKDV{Lys(Me)}DLFDYAQE
Peptide 7:  YGKDVKD{NMe-Leu}FDYAQE
Peptide 8:  YGKDVKDL{NMe-Phe}DYAQE
Peptide 9:  YGKDVKDLFD{NMe-Tyr}AQE
Peptide 10: {NMe-Tyr}GKDVKD{NMe-Leu}FDYAQE
Peptide 11: YGKDCVKCDLFDYAQE

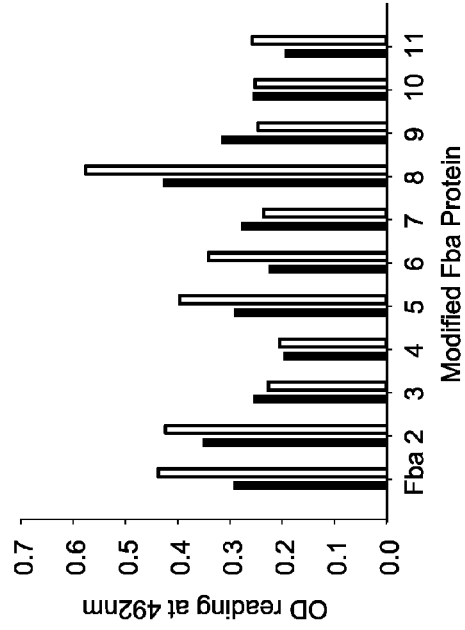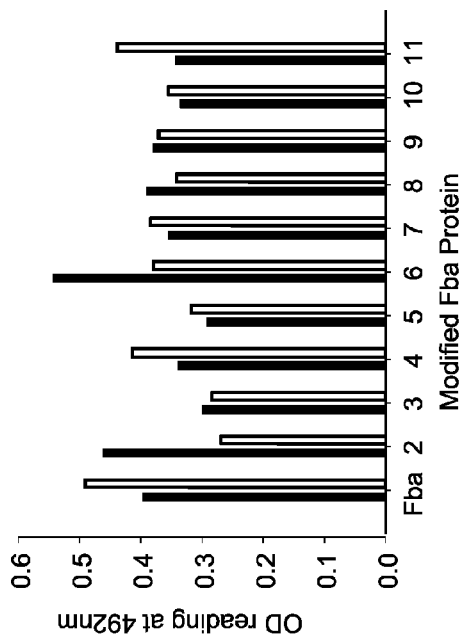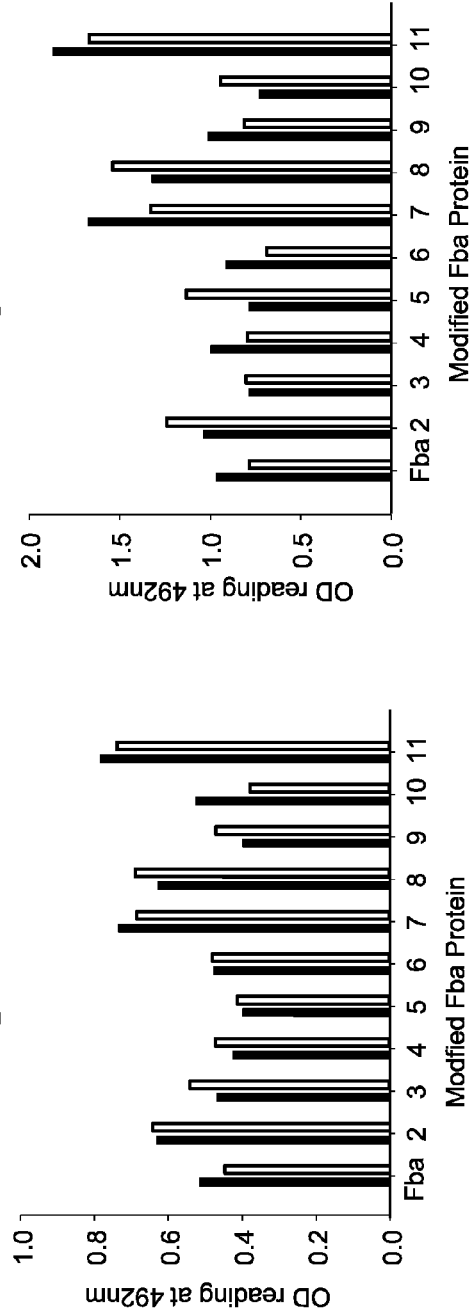
Fig. 20A  Fig. 20B  Fig. 20C  Fig. 20D

Building blocks

SEQUENCE LISTING

<160> NUMBER OF SEQ ID NOS: 20

<210> SEQ ID NO 1
<211> LENGTH: 14
<212> TYPE: PRT
<213> ORGANISM: Candida albicans

<400> SEQUENCE: 1

Tyr Gly Lys Asp Val Lys Asp Leu Phe Asp Tyr Ala Gln Glu
1               5                   10

<210> SEQ ID NO 2
<211> LENGTH: 14
<212> TYPE: PRT
<213> ORGANISM: Candida albicans

<400> SEQUENCE: 2

Pro Arg Ile Gly Gly Gln Arg Glu Leu Lys Lys Ile Thr Glu
1               5                   10

<210> SEQ ID NO 3
<211> LENGTH: 14
<212> TYPE: PRT
<213> ORGANISM: Candida albicans

<400> SEQUENCE: 3

Gln Gly Glu Thr Glu Glu Ala Leu Ile Gln Lys Arg Ser Tyr
1               5                   10

<210> SEQ ID NO 4
<211> LENGTH: 14
<212> TYPE: PRT
<213> ORGANISM: Candida albicans

<400> SEQUENCE: 4

Asp Ser Arg Gly Asn Pro Thr Val Glu Val Asp Phe Thr Thr
1               5                   10

<210> SEQ ID NO 5
<211> LENGTH: 14
<212> TYPE: PRT
<213> ORGANISM: Candida albicans

<400> SEQUENCE: 5

Asn Arg Ser Pro Ser Thr Gly Glu Gln Lys Ser Ser Gly Ile
1               5                   10

<210> SEQ ID NO 6
<211> LENGTH: 14
<212> TYPE: PRT
<213> ORGANISM: Candida albicans

<400> SEQUENCE: 6

Val Pro Leu Asp Gly Lys Thr Ile Thr Asn Asn Gln Arg Ile
1               5                   10

<210> SEQ ID NO 7
<211> LENGTH: 14
<212> TYPE: PRT
<213> ORGANISM: Candida albicans

<400> SEQUENCE: 7

Phe Ala Ile Pro Ala Ile Asn Val Thr Ser Ser Ser Thr Val
1               5                   10

```
<210> SEQ ID NO 8
<211> LENGTH: 19
<212> TYPE: PRT
<213> ORGANISM: Candida albicans

<400> SEQUENCE: 8

Phe Ala Ile Pro Ala Ile Asn Val Thr Ser Ser Ser Thr Val Val Ala
1               5                   10                  15

Ala Leu Glu

<210> SEQ ID NO 9
<211> LENGTH: 9
<212> TYPE: PRT
<213> ORGANISM: Candida albicans

<400> SEQUENCE: 9

Ser Ser Ser Thr Val Val Ala Ala Leu
1               5

<210> SEQ ID NO 10
<211> LENGTH: 15
<212> TYPE: PRT
<213> ORGANISM: Candida albicans

<400> SEQUENCE: 10

Tyr Asp Gln Val Leu Asp Leu Ser Leu Leu Phe Asn Ala Ile Pro
1               5                   10                  15

<210> SEQ ID NO 11
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: METHYLATION of Tyr

<400> SEQUENCE: 11

Xaa Gly Lys Asp Val Lys Asp Leu Phe Asp Tyr Ala Gln Glu
1               5                   10

<210> SEQ ID NO 12
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: METHYLATION of Gly

<400> SEQUENCE: 12

Tyr Xaa Lys Asp Val Lys Asp Leu Phe Asp Tyr Ala Gln Glu
1               5                   10

<210> SEQ ID NO 13
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: METHYLATION of Lys
```

```
<400> SEQUENCE: 13

Tyr Gly Xaa Asp Val Lys Asp Leu Phe Asp Tyr Ala Gln Glu
1               5                   10

<210> SEQ ID NO 14
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: METHYLATION of Val

<400> SEQUENCE: 14

Tyr Gly Lys Asp Xaa Lys Asp Leu Phe Asp Tyr Ala Gln Glu
1               5                   10

<210> SEQ ID NO 15
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: METHYLATION of Lys

<400> SEQUENCE: 15

Tyr Gly Lys Asp Val Xaa Asp Leu Phe Asp Tyr Ala Gln Glu
1               5                   10

<210> SEQ ID NO 16
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: METHYLATION of Leu

<400> SEQUENCE: 16

Tyr Gly Lys Asp Val Lys Asp Xaa Phe Asp Tyr Ala Gln Glu
1               5                   10

<210> SEQ ID NO 17
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: METHYLATION of Phe

<400> SEQUENCE: 17

Tyr Gly Lys Asp Val Lys Asp Leu Xaa Asp Tyr Ala Gln Glu
1               5                   10

<210> SEQ ID NO 18
<211> LENGTH: 14
<212> TYPE: PRT
<213> ORGANISM: Artificial sequence
```

```
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: METHYLATION of Tyr

<400> SEQUENCE: 18

Tyr Gly Lys Asp Val Lys Asp Leu Phe Asp Xaa Ala Gln Glu
1               5                   10

<210> SEQ ID NO 19
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: METHYLATION of Tyr
<220> FEATURE:
<221> NAME/KEY: MOD_RES
<222> LOCATION: (8)..(8)
<223> OTHER INFORMATION: METHYLATION of Leu

<400> SEQUENCE: 19

Xaa Gly Lys Asp Val Lys Asp Xaa Phe Asp Tyr Ala Gln Glu
1               5                   10

<210> SEQ ID NO 20
<211> LENGTH: 16
<212> TYPE: PRT
<213> ORGANISM: Artificial sequence
<220> FEATURE:
<223> OTHER INFORMATION: Synthetic peptide

<400> SEQUENCE: 20

Tyr Gly Lys Asp Cys Val Lys Cys Asp Leu Phe Asp Tyr Ala Gln Glu
1               5                   10                  15
```

PEPTIDE AND CONJUGATE VACCINES FOR FUNGAL INFECTIONS

This is the United States national stage of international application PCT/US2012/034511, international filing date Apr. 20, 2012, which claims the benefit of the filing date of provisional U.S. application Ser. No. 61/477,738, filed Apr. 1, 2011 under 35 U.S.C. §119(e).

This invention was made with government support from the National Institutes of Health under the NIH-NIAID program grant number PO1 AI061537. The government has certain rights in this invention.

TECHNICAL FIELD

This invention relates to new peptide and peptide conjugate vaccines to induce long lasting immunological protection against fungal infections and diseases, and new monoclonal antibodies to provide rapid but short lived protection against fungal infection.

BACKGROUND ART

The polymorphic fungus *Candida albicans* is a commensal organism that colonizes the gastrointestinal tract, vagina and some cutaneous areas of the majority of healthy humans. However, under certain conditions the fungus is able to cause a variety of infections, ranging from mucosal to life-threatening invasive candidiasis (18). *C. albicans* continues to be the most common cause of various forms of candidaisis (34, 47), but several other *Candida* spp. are also important agents. Invasive disease is associated with billions of dollars each year in healthcare costs and a mortality rate estimated at ~40% (32, 33). The limited number and toxicity of antifungal agents, and, most importantly, the poor outcome of almost half of the number of candidemia patients treated with appropriate antifungal therapy, militates in favor of disease prevention, possibly through active and passive immunization strategies (10, 15, 41).

The protective role of antibodies against *Candida* has been controversial, but the evidence is mounting in favor for this mode of protection. Specificity of protective antibodies may be for *C. albicans* cell wall polysaccharides, proteins and peptides (13, 17, 40, 53, 55). As a prevention strategy, protection against disease may be actively or passively acquired by vaccination and transfer of preformed monoclonal antibodies, respectively. As a therapeutic measure, experimental evidence indicates that preformed antibodies may enhance the effectiveness of antifungal agents (24, 43).

The first fully synthetic glycopeptide vaccines against *C. albicans* induced protection against disseminated candidiasis in mice (53). Six putative T-cell peptides found in *C. albicans* cell wall proteins were conjugated to the protective β-1,2-mannotriose [β-(Man)$_3$] glycan epitope to create glycopeptide conjugates. The six proteins from which the peptides, denoted in parentheses, were derived because of expression during human candidiasis and cell wall association and included: fructose-bisphosphate aldolase (Fba) (YGKDVKDLDYAQE; SEQ ID NO:1); methyltetrahydropteroyltriglutamate homocysteine methyltransferase (Met6) (PRIGGQRELKKITE; SEQ ID NO:2); hyphal wall protein-1 (Hwp1) (QGETEEALIQKRSY; SEQ ID NO:3); enolase (Enol) (DSRGNPTVEVDFTT; SEQ ID NO:4); glyceraldehyde-3-phosphate dehydrogenase (Gap1) (NRSPSTGEQKSSGI; SEQ ID NO:5); and phosphoglycerate kinase (Pgk1) (VPLDGKTITNNQRI; SEQ ID NO:6) (53). The intent of this work was that the peptides would serve as T-cell epitopes, promoting protective antibody responses against the glycan part of the glycopeptide conjugates. Thus, the immunization protocols were designed to favor antibody, rather than cell-mediated immune (CMI) responses and antibodies were generated against both the glycan and peptide parts of the various conjugates. That is, by DC based immunization protocols favoring antibody production, the three glycoconjugates β-(Man)$_3$-Fba, β-(Man)$_3$-Meth and β-(Man)$_3$-Hwp1 induced protection from hematogenous challenge with the fungus as evidenced by mouse survival and low kidney fungal burden (53). The β-(Man)$_3$-Enol and β-(Man)$_3$-Gap1 gave moderate protection, and the β-(Man)$_3$-Pgk1 slightly enhanced disease. For the β-(Man)$_3$-Fba conjugate, protection was uniquely acquired through immunity against the glycan and the Fba peptide. The native protein fructose-1,6-bisphosphate aldolase (Fba1p), which catalyzes the reversible cleavage of fructose-1,6-bisphosphate to dihydroxyacetone phosphate and glyceraldehyde 3-phosphate, has become an attractive antifungal target for several reasons. First, this key enzyme is required for growth on both fermentative and nonfermentative carbon sources; therefore it is essential for *C. albicans* viability and other pathogenic fungi (48). Second, fungal fructose-1,6-bisphosphate aldolases are distinct from human fructose-1,6-bisphosphate aldolases. *C. albicans* Fba1p belongs to the family of class II aldolases found predominantly in fungi and prokaryotes (39). In contrast, the human enzyme belongs to the class I aldolases, and the sequence of human aldolase is significantly different from those of fungal aldolases (39), thus it is reasonable to expect that it may be possible to achieve an immunologic response specific only to the fungal enzyme. Indeed, the Fba 14 mer peptide sequence (YGKDVKDLFDYAQE; SEQ ID NO:1) is unique to *C. albicans* (53).

U.S. Pat. No. 4,771,127 discloses polysaccharide-protein conjugate vaccines synthesized using polysaccharide derived from *Pseudomonas aeruginosa* lipopolysaccharide coupled to either tetanus toxoid or *P. aeruginosa* toxin A.

U.S. Pat. Nos. 5,578,309; 6,488,929; and 6,30,146 disclose vaccines for *Candida albicans* based on the isolated phosphomannoprotein cell wall complexes of *C. albicans*, including β-1,2-linked tri-mannose residues.

U.S. Pat. Nos. 6,309,642; 6,391,587; and 6,403,090 and U.S. Patent Application Publication U.S. 2003/0072775 disclose vaccines based on peptides that mimic phosphormanna epitopes or polyneucleotides encoding the peptide mimotopes, and discloses monoclonal antibodies, including MAb B6.1, for passive immunization against infections of *Candida albicans*.

U.S. Pat. No. 7,722,890; U.S. Patent Application Publication Nos. 2006/0058506, 2008/0193481 and 2010/0209448; and International Publication Nos. WO 03/090787 and WO 2006/096970 disclose vaccines against *Candida* species based on immunogenic oligosaccharide compositions comprising native O-linked and S-linked oligosaccharides, including β-(1-2)-β-D-mannopyrose triose (also referred to as β-(Man)$_3$ or β-(1,2)-mannotriose), coupled to a protein carrier, including the protein carrier tetanus toxoid.

DISCLOSURE OF INVENTION

We have designed several new peptides based on *Candida* cell wall proteins that show efficacy as a vaccine development against candidiasis, and potentially other fungal diseases for some of the peptides. The protective capacity of these peptide vaccines, whether either formulated with a human-approved adjuvant or by a DC-based immunization approach that favors production of protective antibody, was assessed in a murine model of human disseminated candidiasis. The vaccine conferred protection. In addition, using the Fba peptide (SEQ ID NO:1), we have shown that vaccine protection was associated with production of anti-Fba peptide antibodies in the sera of immunized mice. Importantly, the Fba peptide may be expected to be immunogenic in humans. A monoclonal antibody (MAb E2-9) specific for the Fba peptide was isolated from splenocytes of Fba-immunized mice and was shown to be protective against candidiasis in passive transfer experiments. This monoclonal antibody can be used for short-term protection against candidiasis. We have also designed peptide vaccines based on Fba or Met6 (Fba3 (SEQ ID NO:8); Fba4 (SEQ ID NO:9; and Met6-2 (SEQ ID NO:10) that would be more general fungal vaccines, and have shown that these peptides have efficacy as vaccines. In addition, we modified the Fba sequence by methylating amino acids at different positions (SEQ ID NOS:11-19) or by adding two cysteine residues (SEQ ID NO:20). These modified Fba indicated a degree of effectiveness as vaccines.

In addition, we developed a new vaccine conjugate by modifying the β-(Man)$_3$-Fba conjugate by coupling it to tetanus toxoid (TT) to improve immunogenicity and allow for use of an adjuvant suitable for human use. The modified β-(Man)$_3$-Fba-TT was administered either alone or as a mixture made with alum or monophosphoryl lipid A (MPL) adjuvants and given to mice by a subcutaneous (s.c.) route. Mice vaccinated with or surprisingly, without adjuvant responded well by making robust antibody responses. The immunized groups showed a high degree of protection against a lethal challenge with C. albicans as evidenced by increased survival times and reduced kidney fungal burden as compared to control groups that received only adjuvant or DPBS buffer prior to challenge. To confirm that induced antibodies were protective, sera from mice immunized against the β-(Man)$_3$-Fba-TT conjugate transferred protection against disseminated candidiasis to naïve mice, whereas C. albicans-absorbed immune sera did not. Similar antibody responses and protection induced by the β-(Man)$_3$-Fba-TT vaccine was observed in inbred BALB/c and outbred Swiss Webster mice. The addition of TT to the glycopeptide conjugate resulted in a new self-adjuvanting vaccine that promotes robust antibody responses without the need for additional adjuvant, which is a major benefit to a vaccine design against disseminated candidiasis.

BRIEF DESCRIPTION OF THE DRAWINGS

FIG. 4A shows the percent survival in the four groups. FIG. 4B shows the CFUs in kidneys, and FIG. 4C shows the CFUs in brain tissue of the mice that survived the experiment. The bar of each panel in FIGS. 4B and 4C indicates mean of CFUs for each group, and each point represents an individual mouse.

FIG. 6A shows the level of antibody production as measured using ELISA from serum samples collected 14 days after immunization, diluted 1:100 and tested by ELISA on plates coated with synthetic Fba-MAP. FIG. 6B shows survival curves of the mice from the treatments with adjuvant alone, control, and adjuvant with Fba peptide. FIG. 6C shows the number of viable fungal units (CFUs) per kidney pairs compared to DPBS control group or adjuvant only groups.

FIG. 7A shows the size of heavy and light chains of E2-9 and B7-18 with corresponding sizes as shown on 12.5% SDS page gel under reducing condition. FIG. 7B shows the isotype of E2-9, B7-18 and B7-22 confirmed as IgM by SDS-PAGE analysis as indicating a whole molecular size consistent with IgM molecule; the putative IgM pentamer was observed by western blots of 10% SDS-PAGE gel run under nonreducing conditions and the molecular mass of the purified anti-Fba IgM MAb (E2-9) was estimated at 900 kD.

*cans* using both yeast and hyphal forms of the fungus. MAb B6.1, which is specific to β-(Man)$_3$, was used as a positive control.

Figure 8A:
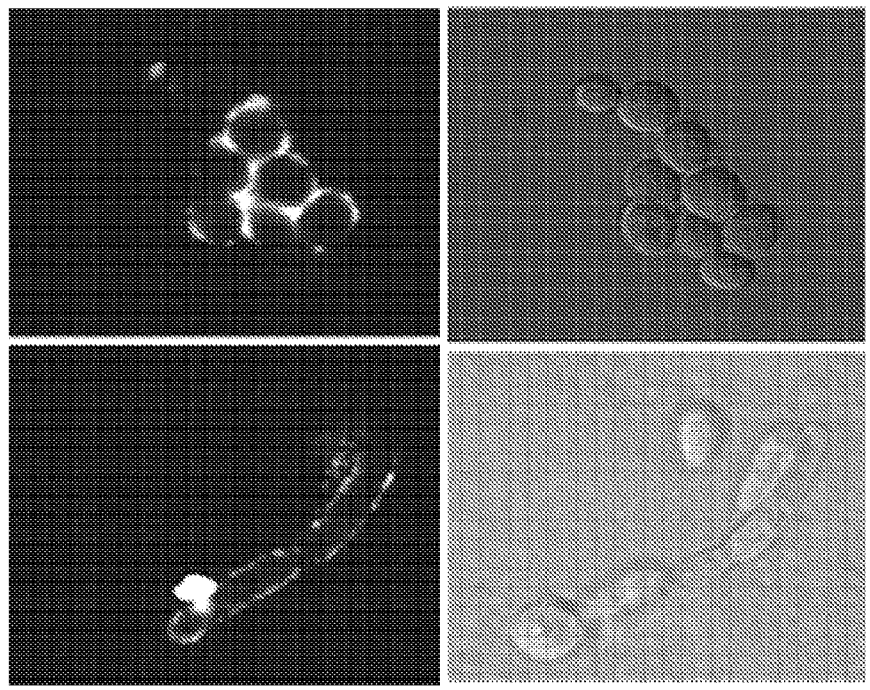
FIG. 8A show the use of MAb E2-9 to detect Fba peptide in confocal microscopic analyses on the cell surface of C. albi-
Figure 8B:
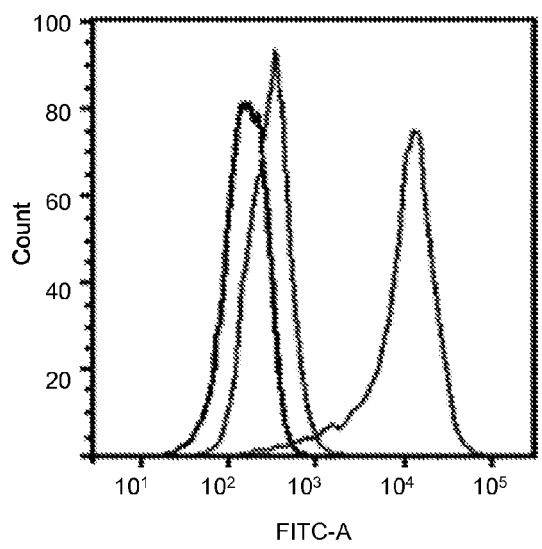

FIG. 8B indicates results from flow cytometric analysis for binding to the cell surface of *C. albicans*, using MAb B6.1, Fba MAb E2-9, and 2$^{nd}$ FITC-conjugated Ab only.

Figure 8C:
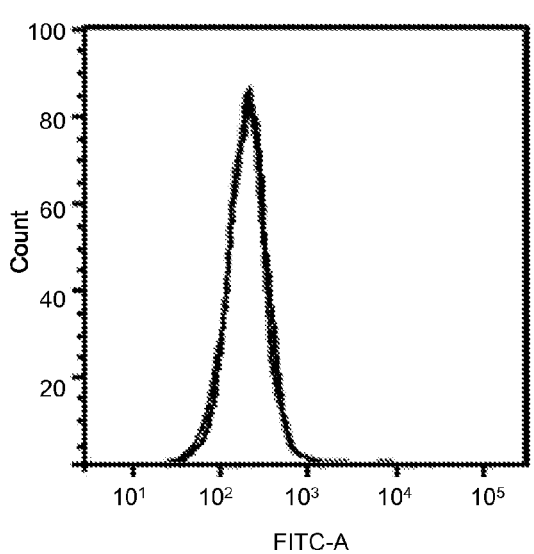

FIG. 8C shows results from flow cytometric analysis using an important additional negative control, binding of both MAbs E2-9 and B6.1 to live *Saccharomyces cerevisiae*, which should not express either Fba or the β-trimannose epitope.

Figure 9A:
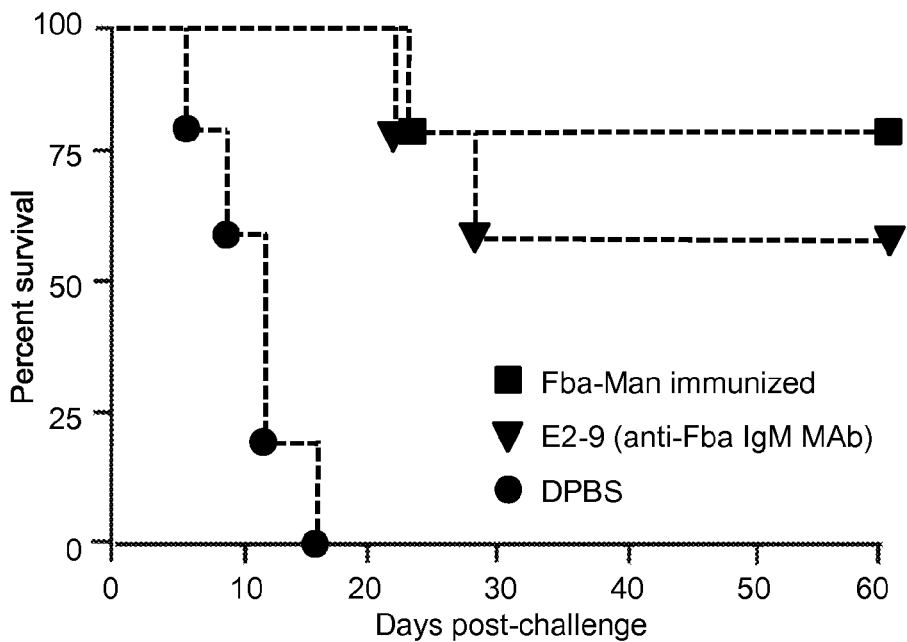
Figure 9B:
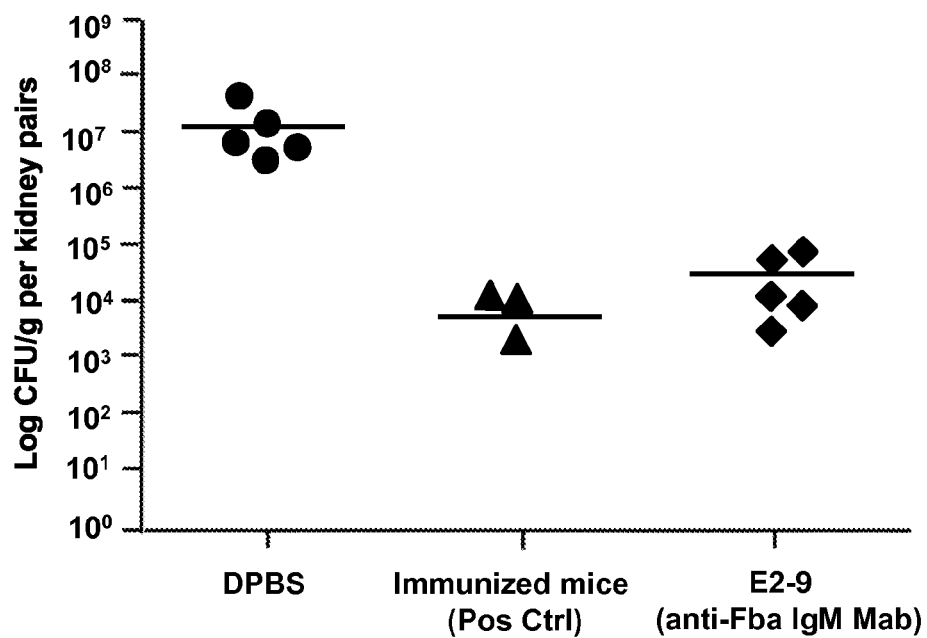

FIGS. 9A and 9B show percent survival (FIG. 9A) and kidney CFUs (FIG. 9B) of mice given MAb E2-9 (16 ng/ml, 0.5 ml) 4 h before i.v. *C. albicans* challenge, and another 0.2 ml of MAb E2-9 was given 24 h after the first dose. Mice that were immunized with the β-(Man)$_3$-Fba conjugate were used as a positive control for survival and DPBS and MAb E2-9 absorbed by *C. albicans* yeast cells was given to naïve mice as a negative control.

Figure 10A:
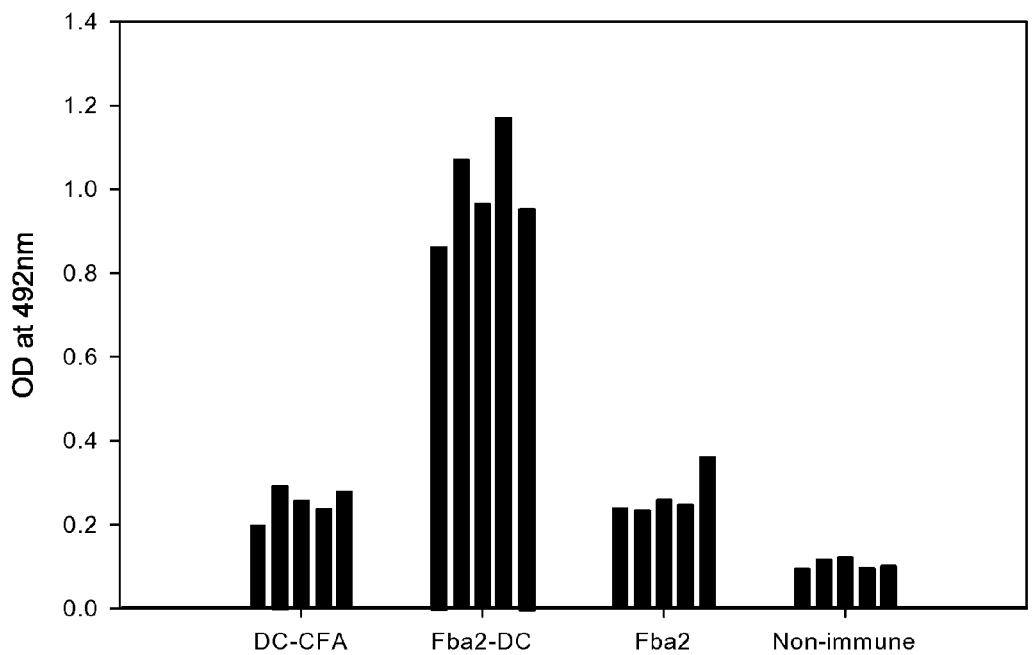
Figure 10B:
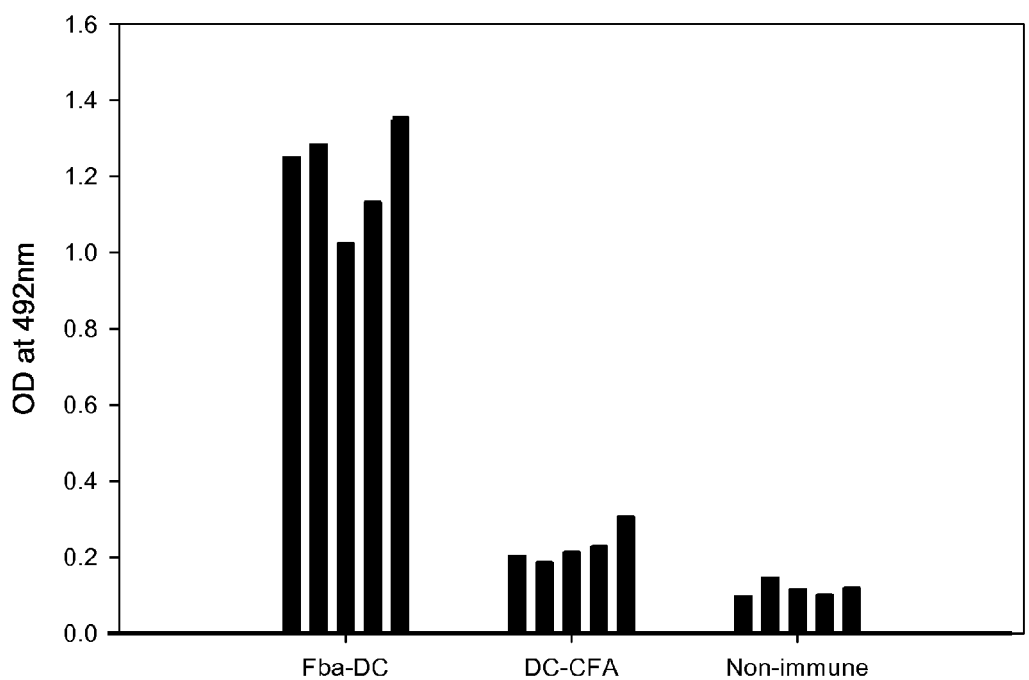

FIGS. 10A and 10B show the antibody production as measured by ELISA from serum collected from BALB/c mice after immunization with a control (DC-CFA), Fba2-DC, Fba2-DC, and non immunized mice. Fba2 was used to pulse DC, and Fba-DC was used as positive control. Serum samples were tested after each injection. As a positive control, anti-Fba responses were also tested, and results are shown in FIG. 10B.

Figure 11:
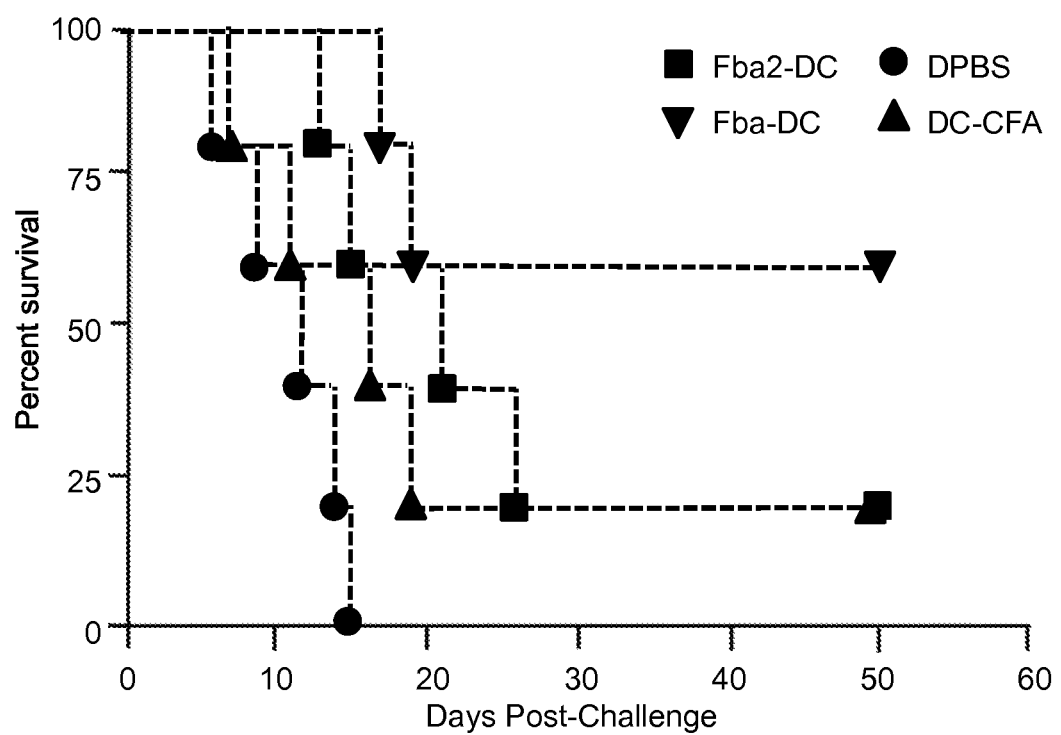

FIG. 11 shows the percent survival in mice immunized with Fba2-DC, Fba-DC, and two controls, DPBS and DC-CFA prior to challenge with *C. albicans*.

Figure 12:
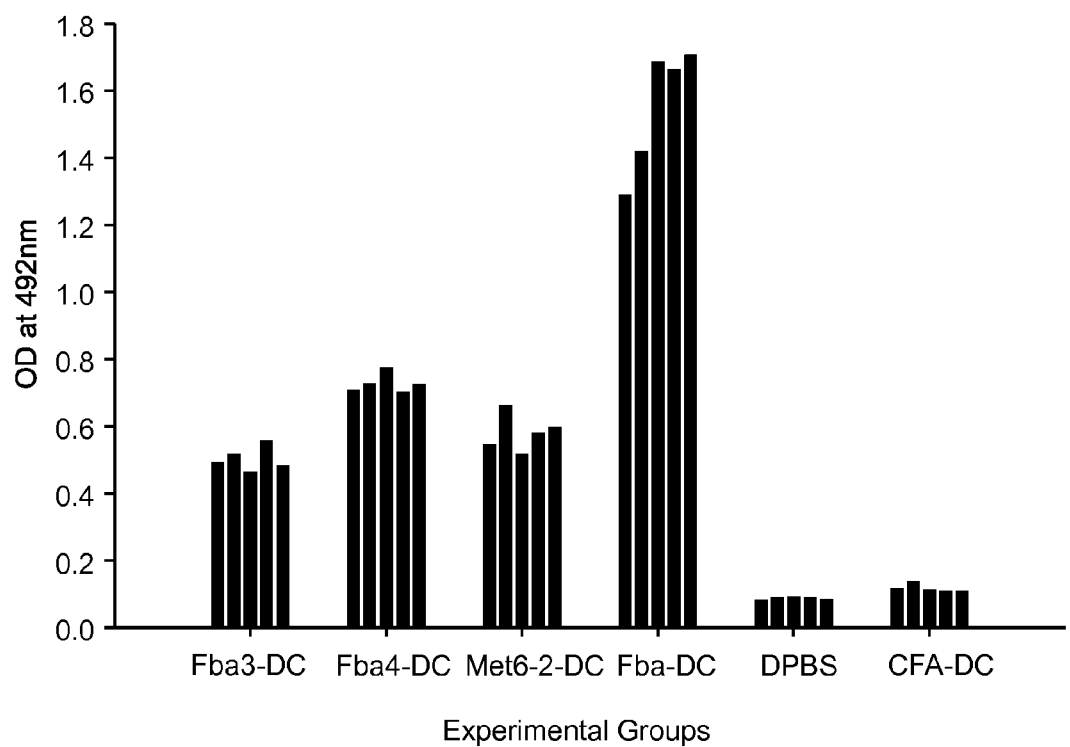

FIG. 12 shows the antibody production as measured by ELISA from serum collected from BALB/c mice after immunization with controls (DPBS and CFA-DC) and four peptide-DCs (Fba3-DC, Fba4-DC, Met6-2-DC, and Fba-DC).

Figure 13A:
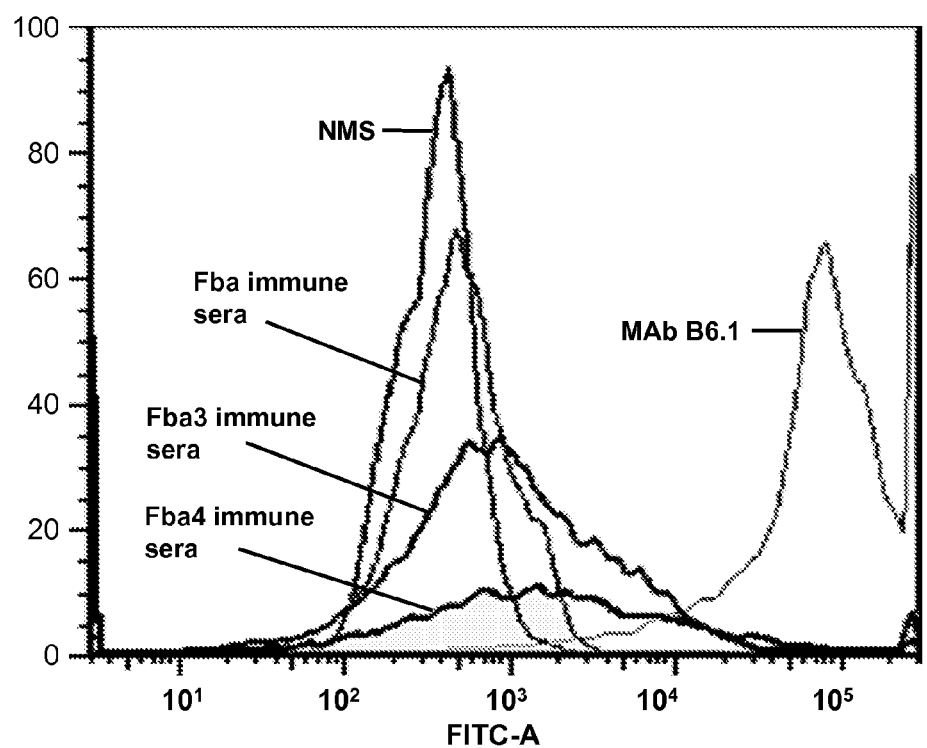
Figure 13B:
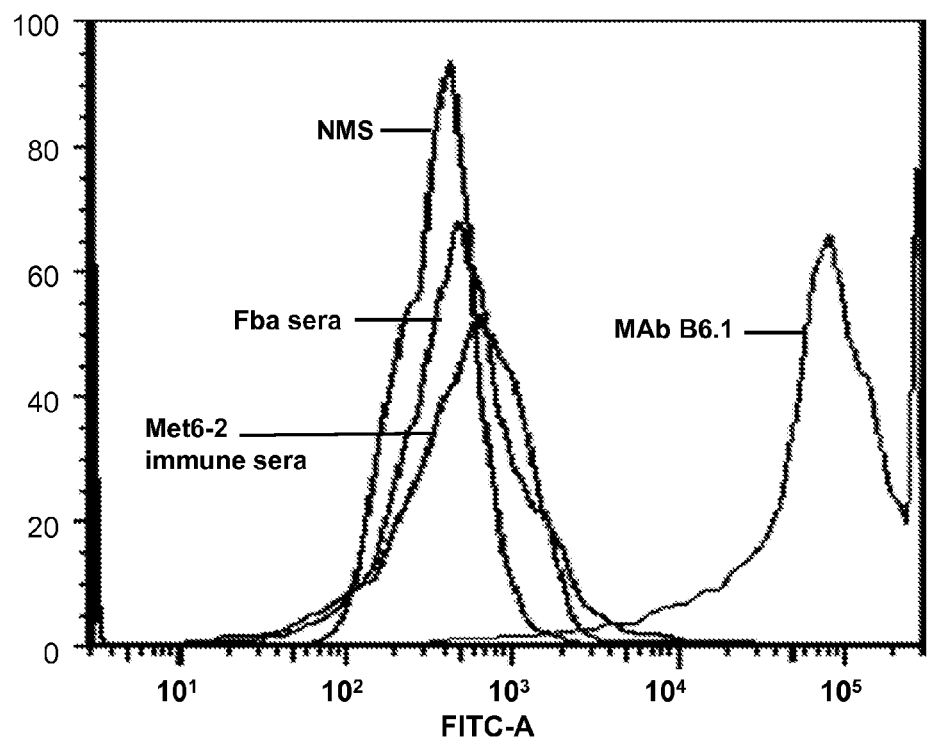

FIGS. 13A and 13B show the results of a flow cytometric analysis to specifically test the binding of antibody in the immune serum to the general peptides expressed on *C. albicans* cell surface. Live fungal cells were reacted with immune serum, and then with goat anti-mouse FITC conjugated 2nd antibodies, and a negative control of cells reacted with Rt normal mouse serum (NMS). The positive control was the monoclonal antibody, MAb B6.1.

Figure 14:
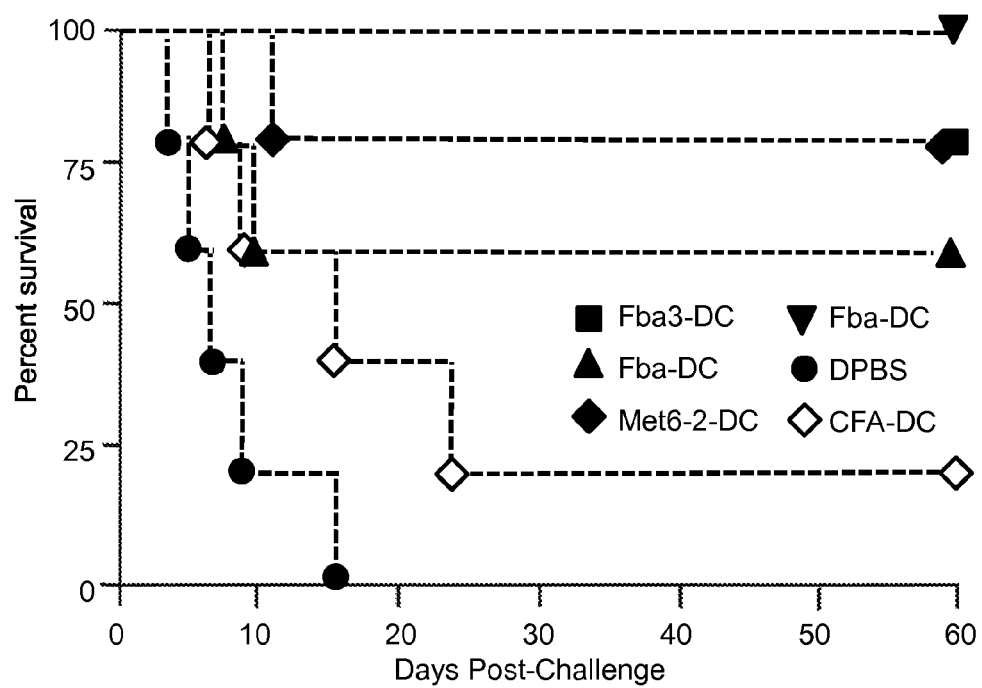

FIG. 14 shows the percent survival in mice immunized with Fba3-DC, Fba4-DC, Fba-DC, Met6-2-DC, and with two controls DPBS and CFA-DC, and then challenged with a lethal dose of *C. albicans*.

Figure 15:
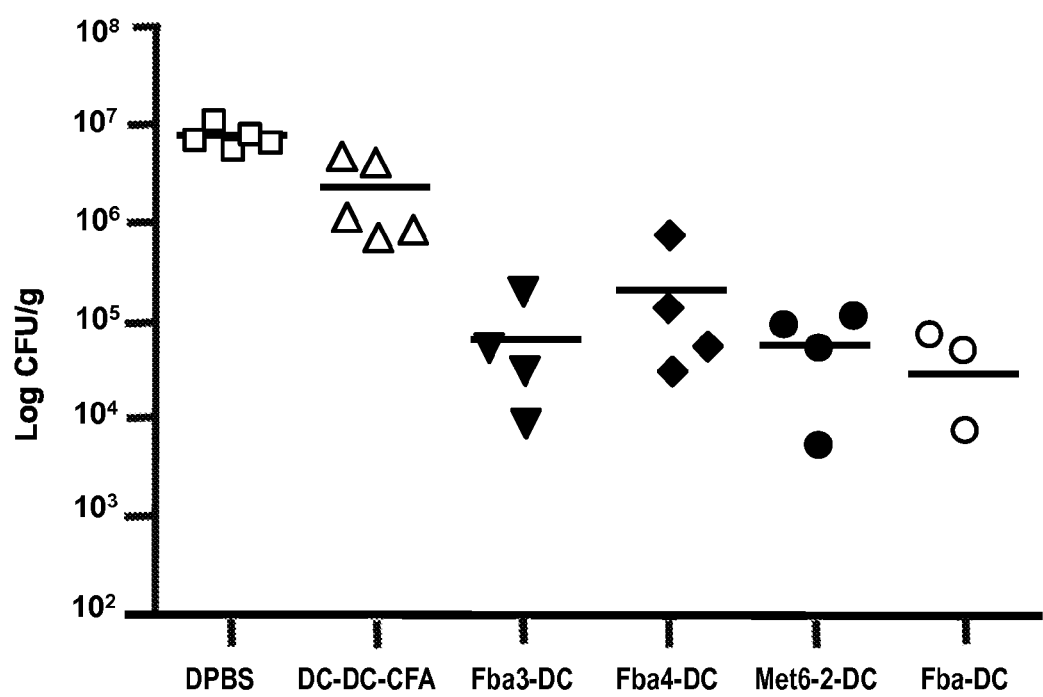

FIG. 15 shows the CFUs from kidneys collected from mice immunized with Fba3-DC, Fba4-DC, Fba-DC, Met6-2-DC, and with two controls DPBS and CFA-DC, then challenged with a lethal dose of *C. albicans*.

Figure 16:
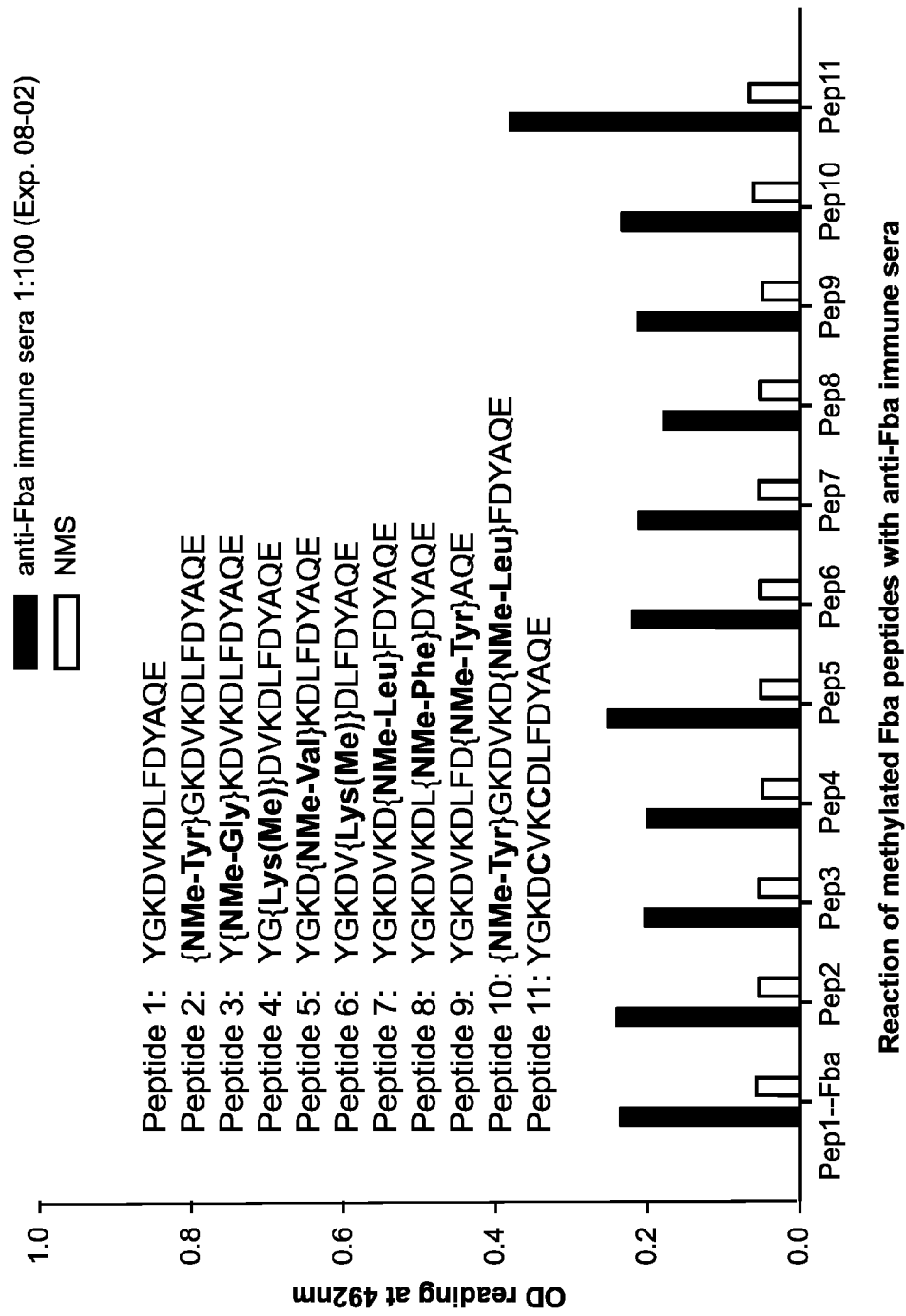

FIG. 16 shows the reaction of modified peptides based on Fba with anti-Fba immune sera and with non-immunized mice sera (NMS). The peptides are defined below in Table 1, and as shown on the figure.

Figure 17:
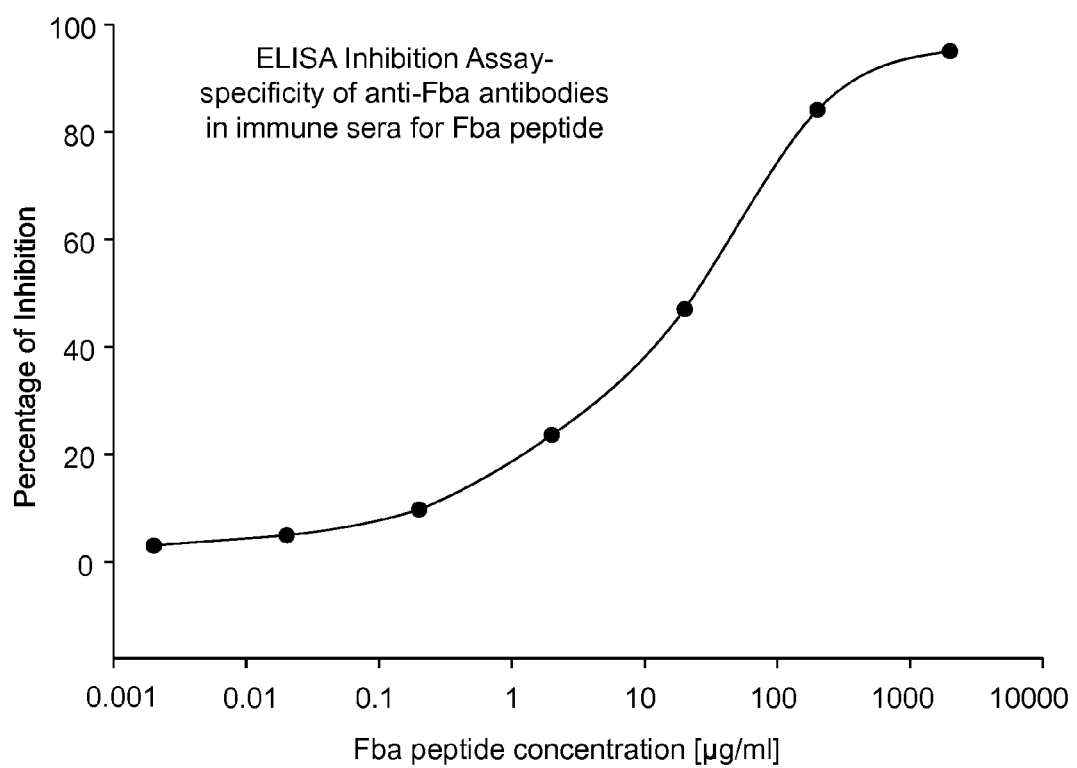

FIG. 17 shows the results of an ELISA inhibition assay testing for the specificity of anti-Fba antibodies in immune sera for Fba peptide.

FIGS. 18A-18J show the results of an ELISA inhibition assay testing for the specificity of anti-Fba antibodies in immune sera for each of the 10 modified Fba peptides, as defined in Table 1 and FIG. 16.

Figure 19:
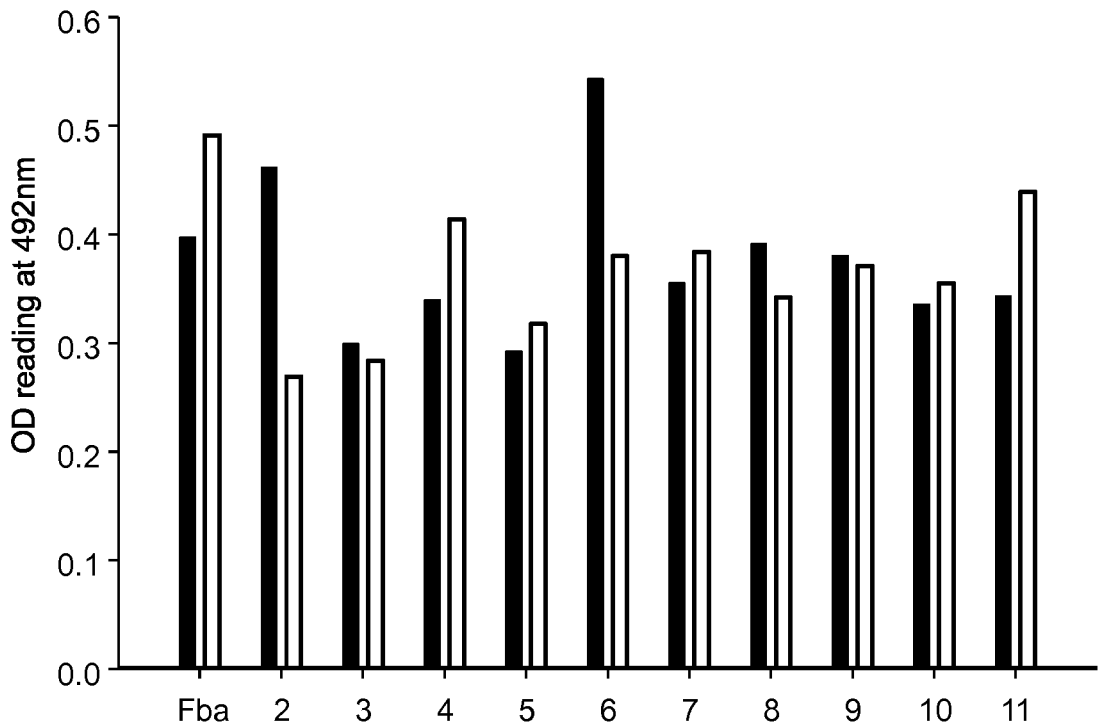

FIG. 19 shows the anti-Fba response of immune sera from mice after a second booster with either Fba or one of the modified Fba peptides as shown in FIG. 19.

FIGS. 20A-20D show the anti-Fba response of immune sera from mice after a second booster with either Fba or one of the modified Fba peptides using different routes of injection and different adjuvants. In FIG. 20A the mice were immunized by i.p. injection and using peptides in alum; FIG. 20B, mice were immunized by i.p. injection and using peptides in alum and MPL; FIG. 20C, mice were immunized by s.c. injection and using peptides in alum; and in FIG. 20D, mice were immunized with the Fba derivatives by s.c. injection and using peptides in alum and MPL.

Figure 21A:
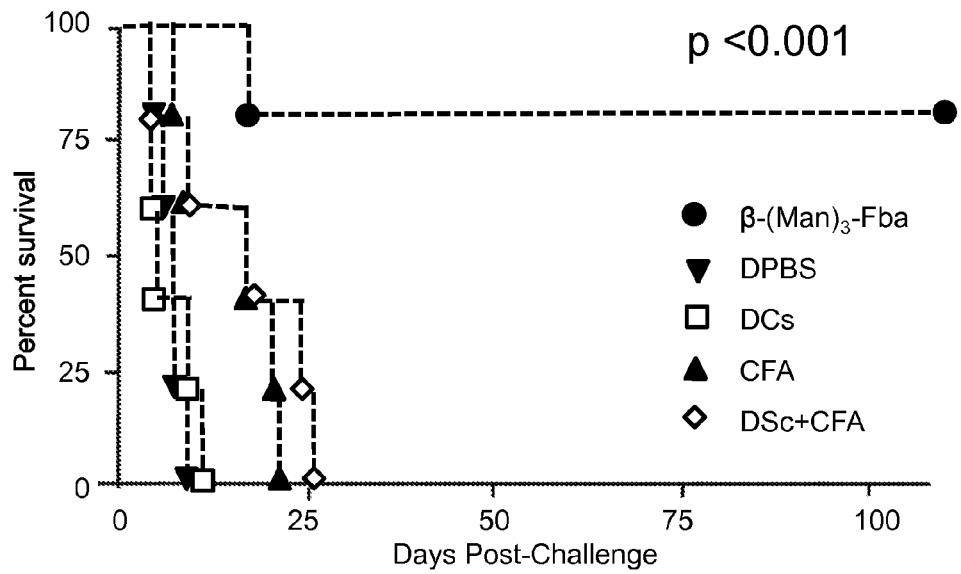
Figure 21B:
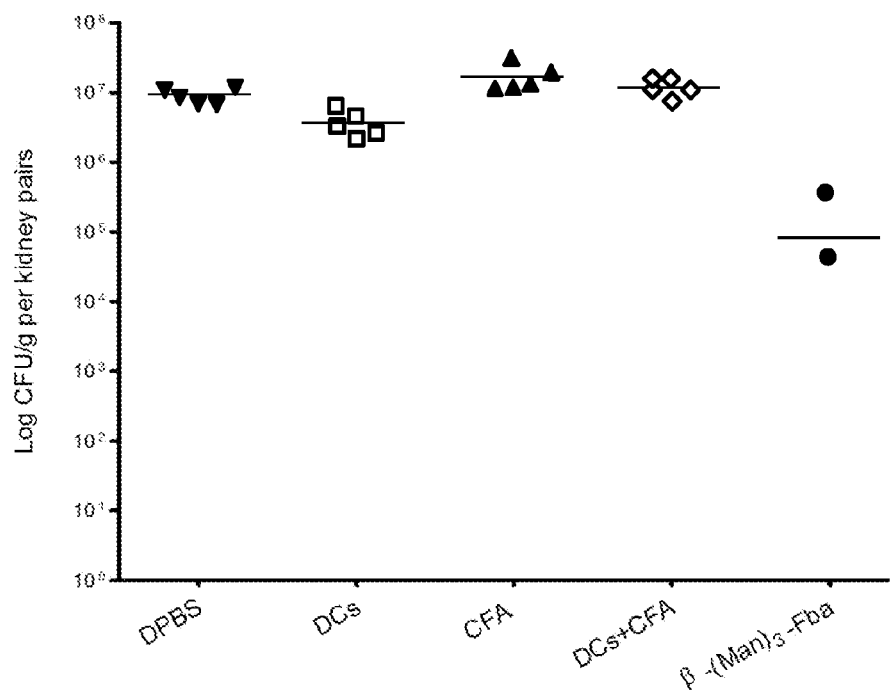

FIGS. 21A-B show protective responses in C57BL/6 mice against experimental disseminated candidiasis in mice immunized against either the β-(Man)$_3$-Fba-pulsed DCs as compared to DPBS, DCs, CFA and DCs+CFA control mice and then challenged with a lethal dose of a prototypical strain of *C. albicans* strain 3153A. FIG. 21A shows the percent survival in the five groups. FIG. 21B shows the CFUs in kidneys tissue of the mice. The bar of each panel in FIG. 21B indicates mean of CFUs for each group, and each point represents an individual mouse.

Figure 21C:
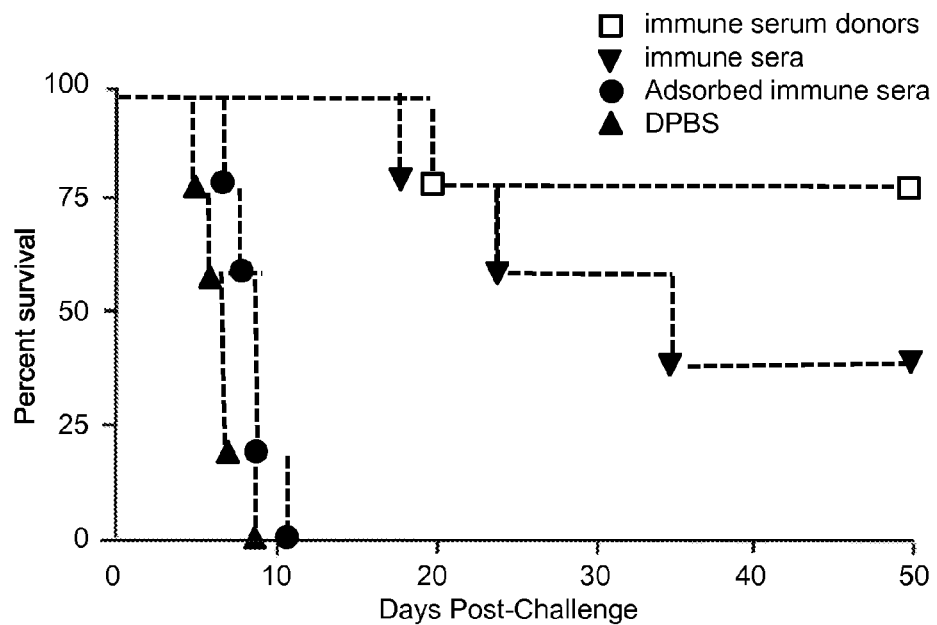
Figure 21D:
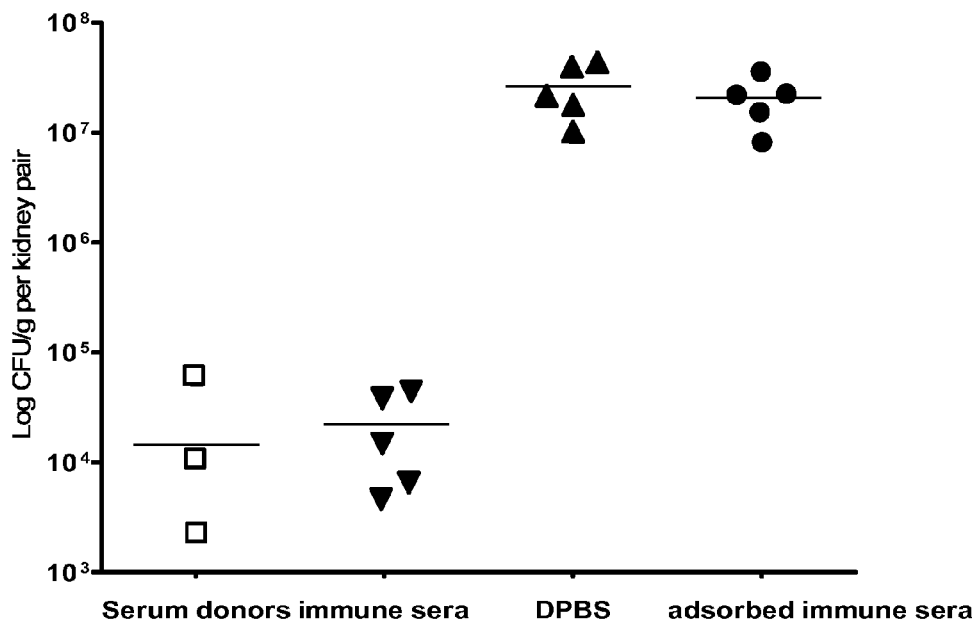

FIGS. 21C and 21D show the responses of naïve C57BL/6 mice given sera from C57BL/6 mice immunized with β-(Man)$_3$-Fba by the DC/CFA method and the sera given i.v. prior to a challenge with a lethal dose of *C. albicans* strain 3153A, as compared to control groups were given either immune sera pre-absorbed with live *C. albicans* yeast cells or DPBS buffer prior to the challenge or the immunized mice. FIG. 21C shows the percent survival in the groups. FIG. 21D shows the fungal counts (CFU) in their kidneys.

Figure 21E:
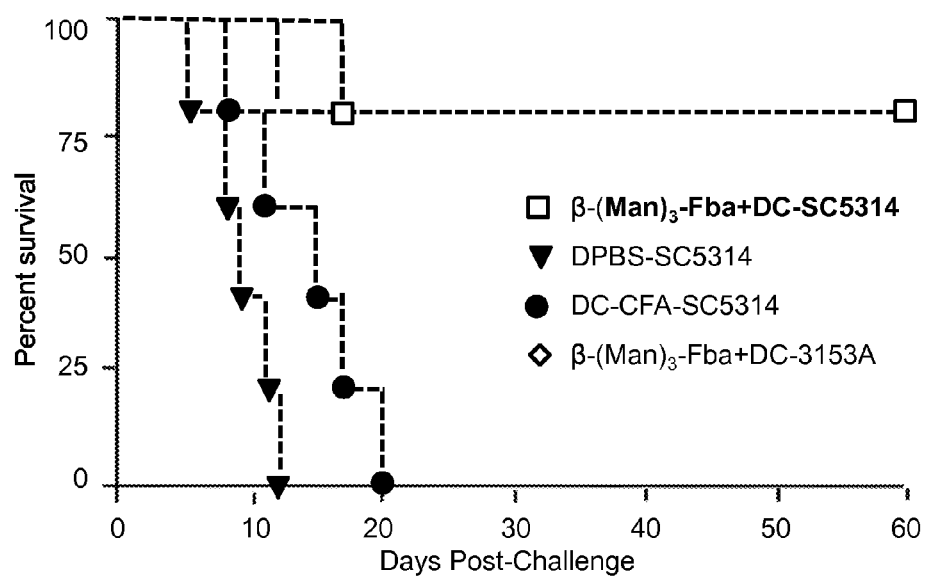

FIG. 21E shows the percent survival in C57BL/6 mice vaccinated using DC/CFA vaccination with the β-(Man)$_3$-Fba and challenged with *C. albicans* strain SC5314, a clinical isolate commonly used in research. Controls were mice given either DPBS or DC-CFA before the challenge, and as a positive control, a group challenged with strain 3153A.

Figure 22A:
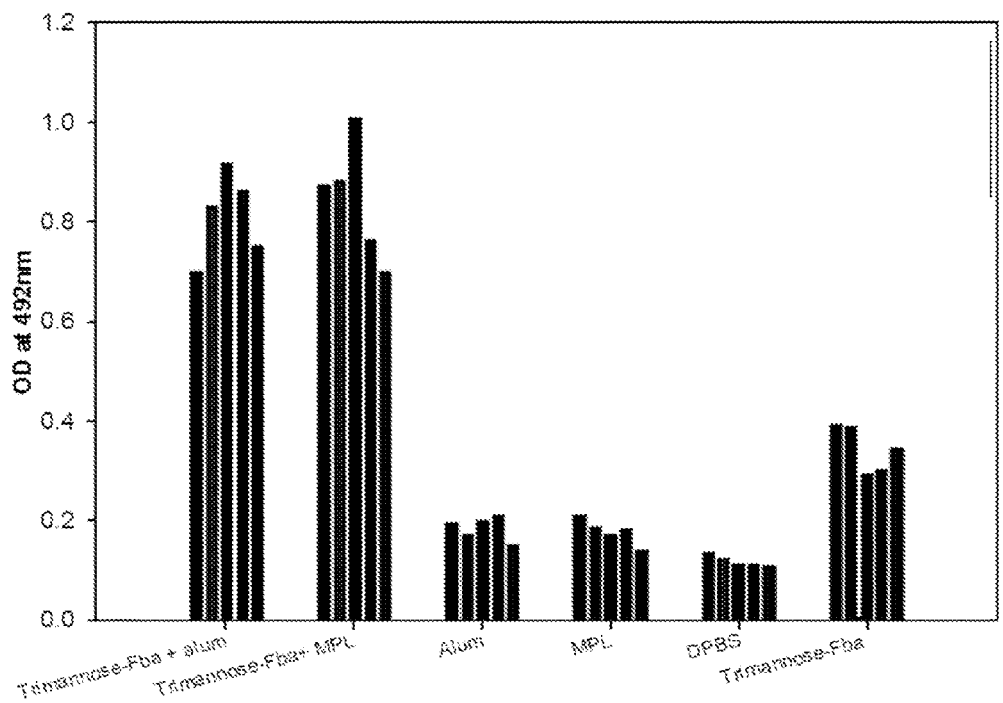
Figure 22B:
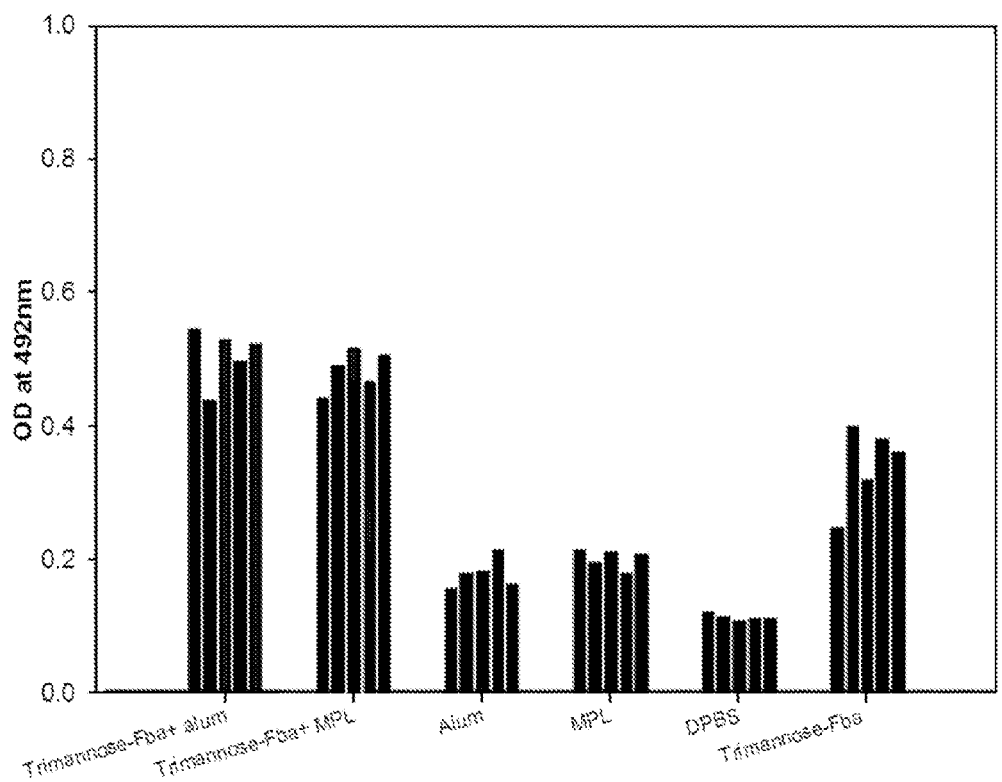
Figure 22C:
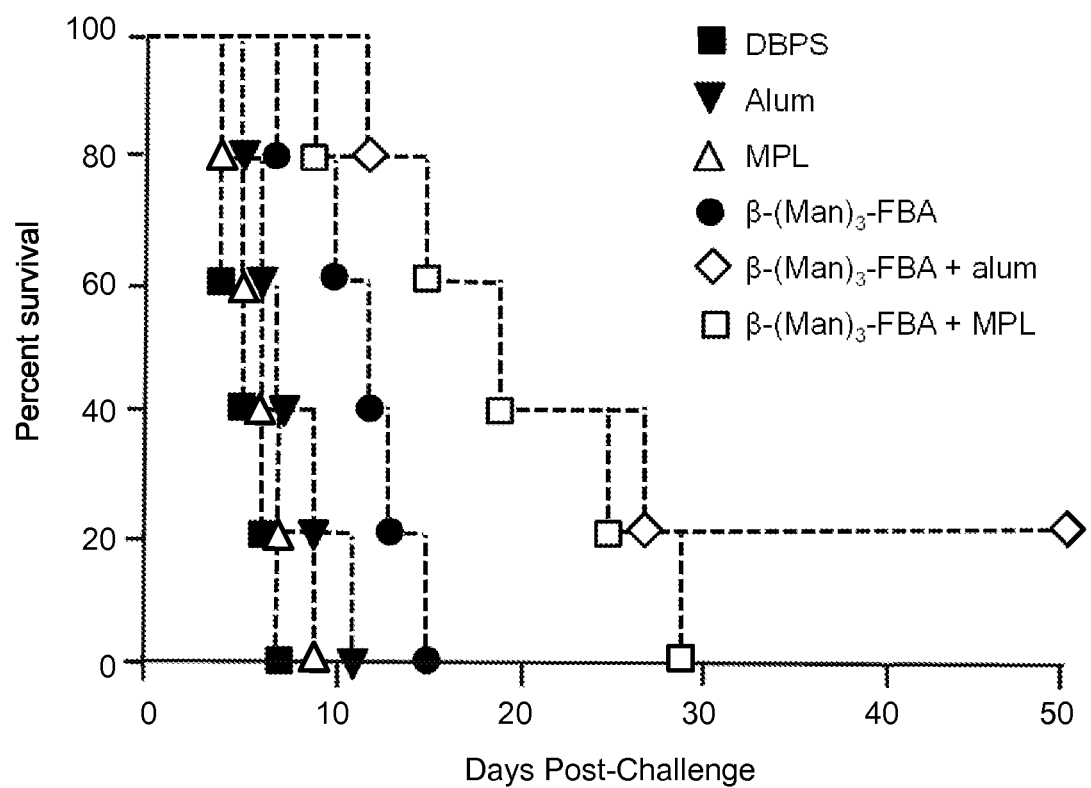

FIGS. 22A-C show the responses of BALB/c mice immunized with 2.5 µg β-(Man)$_3$-Fba administered alone or with either alum or MPL adjuvants. FIGS. 22A and 22B are ELISA results from plates coated with synthetic β-(Man)$_3$ (FIG. 22B) or Fba peptide (FIG. 22A). FIG. 22C shows the percent survival in the same mice.

Figure 23A:
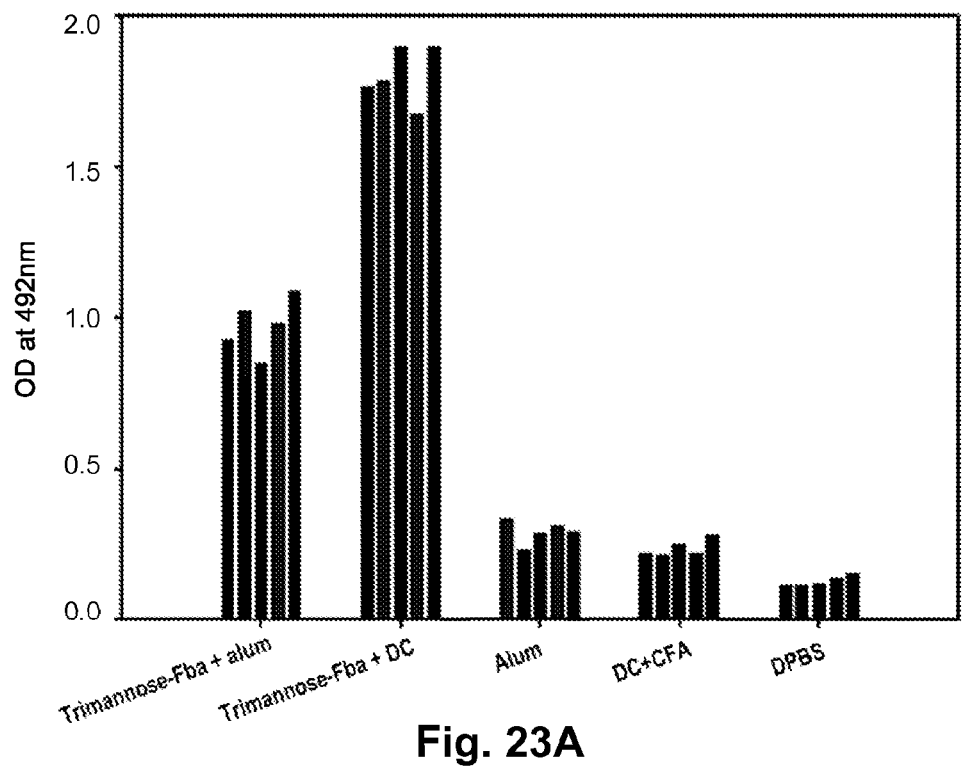
Figure 23B:
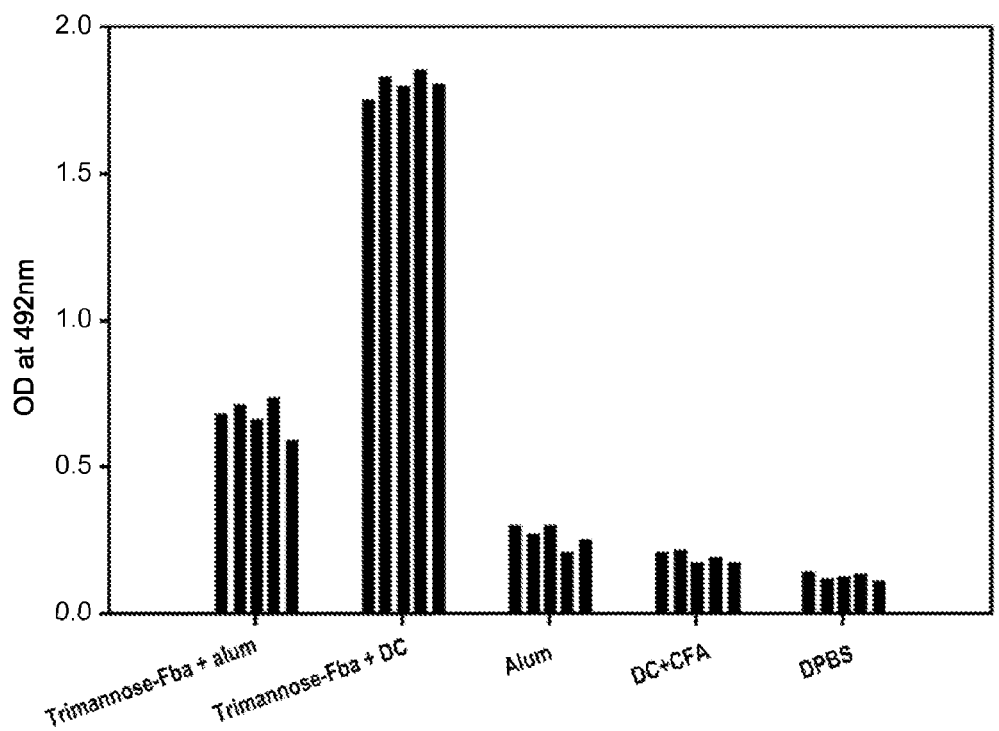
Figure 23C:
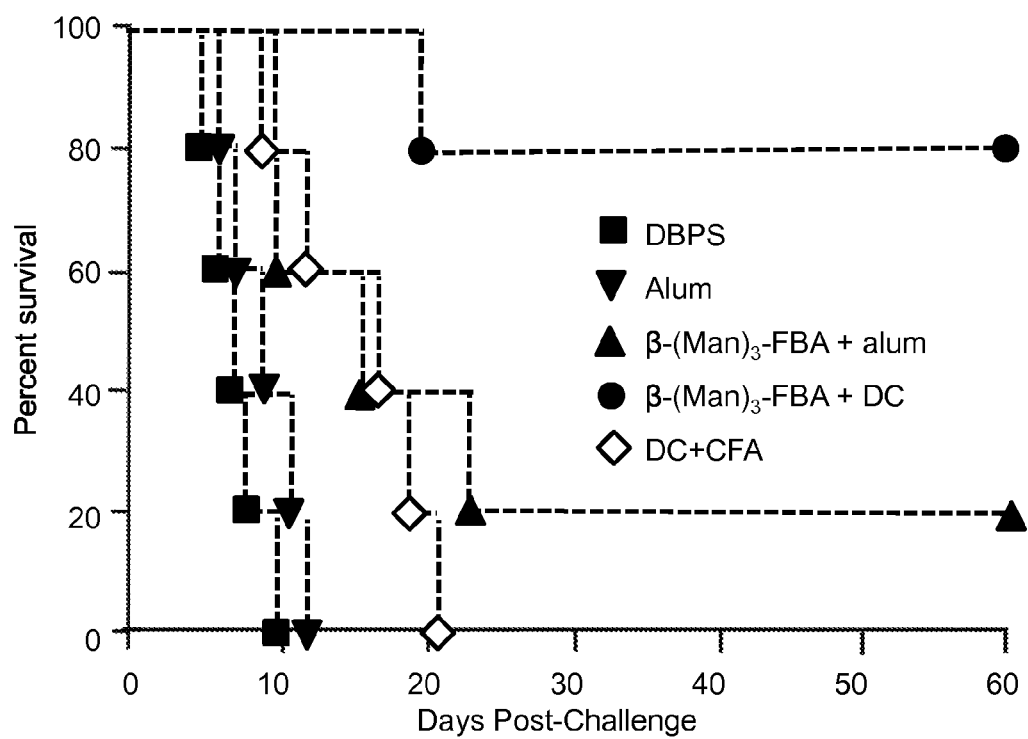

FIGS. 23A-C show the responses of BALB/c mice immunized with 10 µg β-(Man)$_3$-Fba administered either by DC/CFA or with alum adjuvant. FIGS. 23A and 23B are ELISA results from plates coated with synthetic β-(Man)$_3$ (FIG. 23B) or Fba peptide (FIG. 23A). FIG. 23C shows the percent survival in the same mice.

Figure 24A:
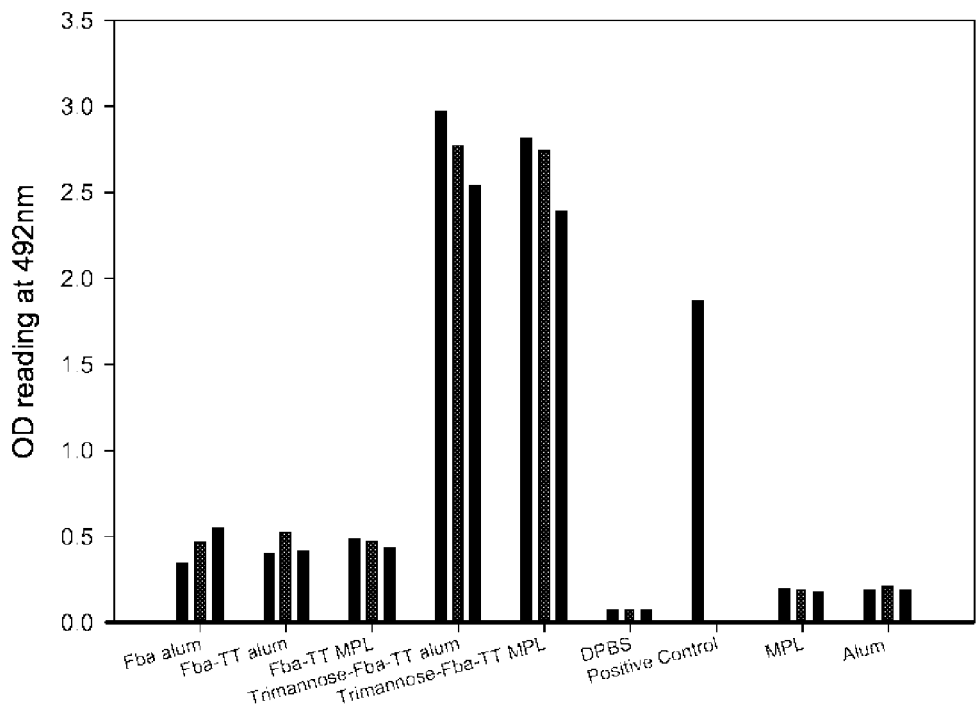
Figure 24B:
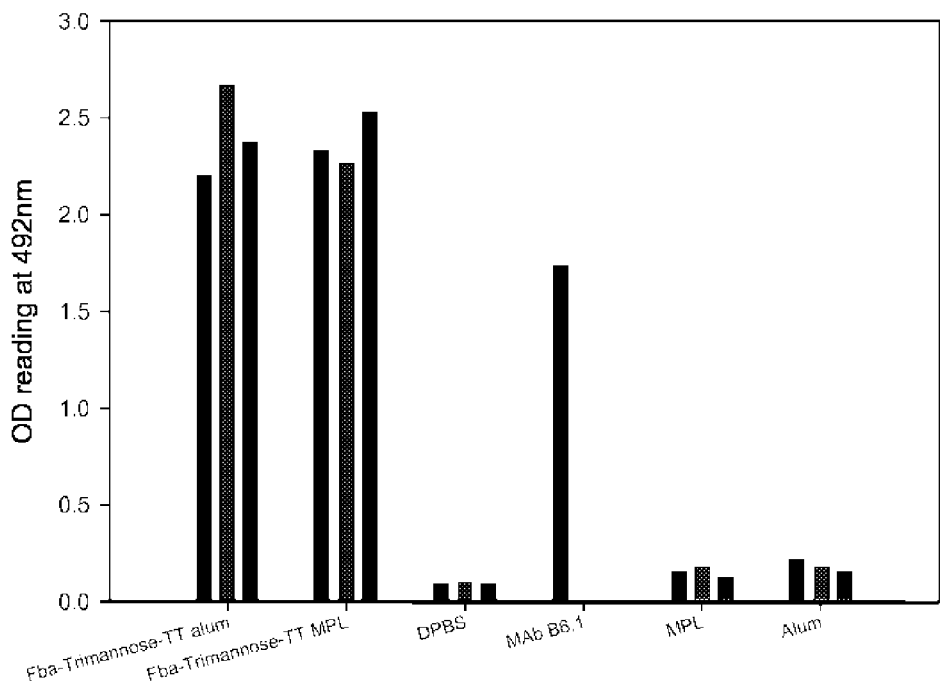

FIGS. 24A and B show ELISA results from mice vaccinated with β-(Man)$_3$-Fba-TT in either alum or MPL as compared to Fba-TT alone or with alum or MPL and controls. The ELISA plates were coated with Fba peptide (FIG. 24A) or the β-(Man)$_3$ (FIG. 24B).

Figure 25A:
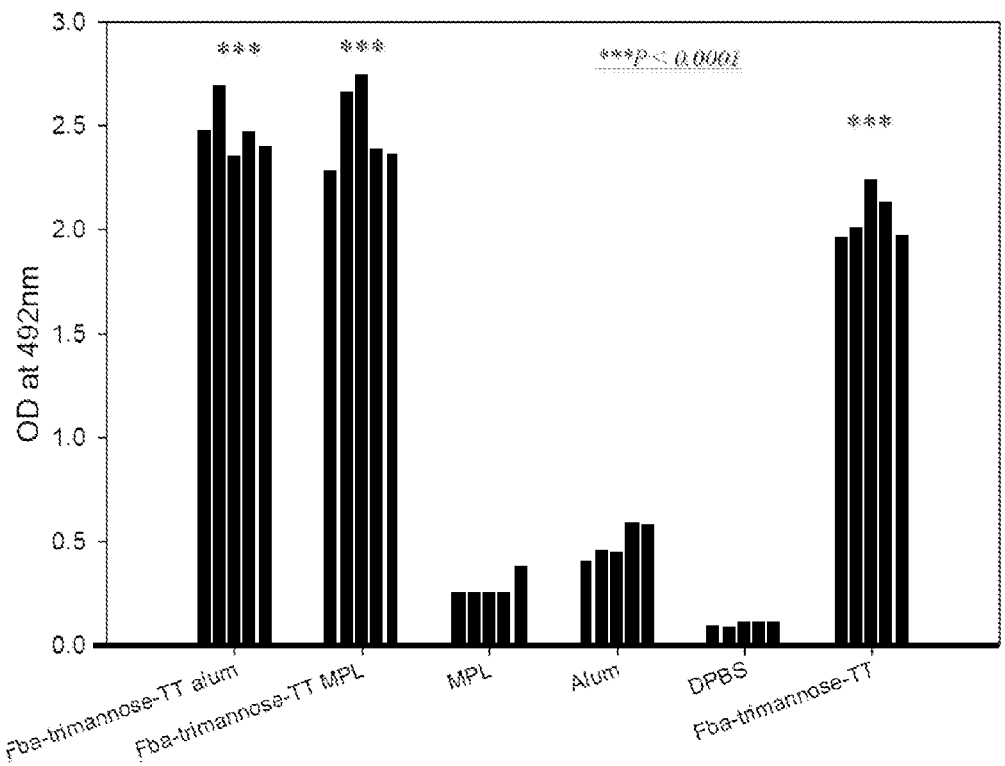
Figure 25B:
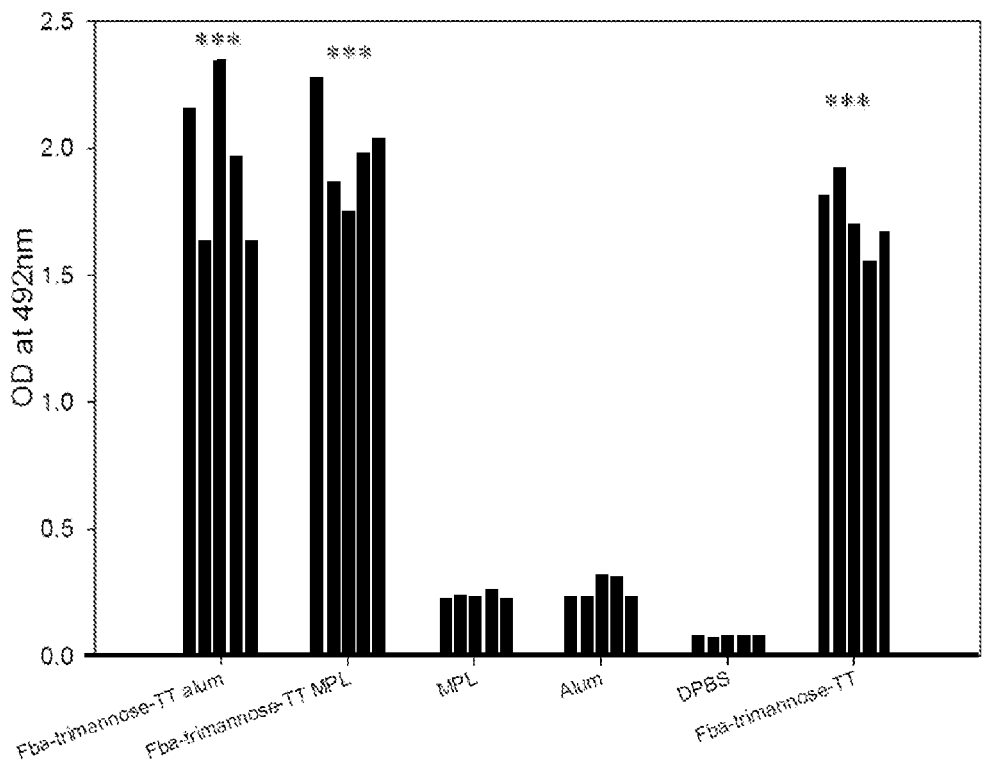
Figure 25C:
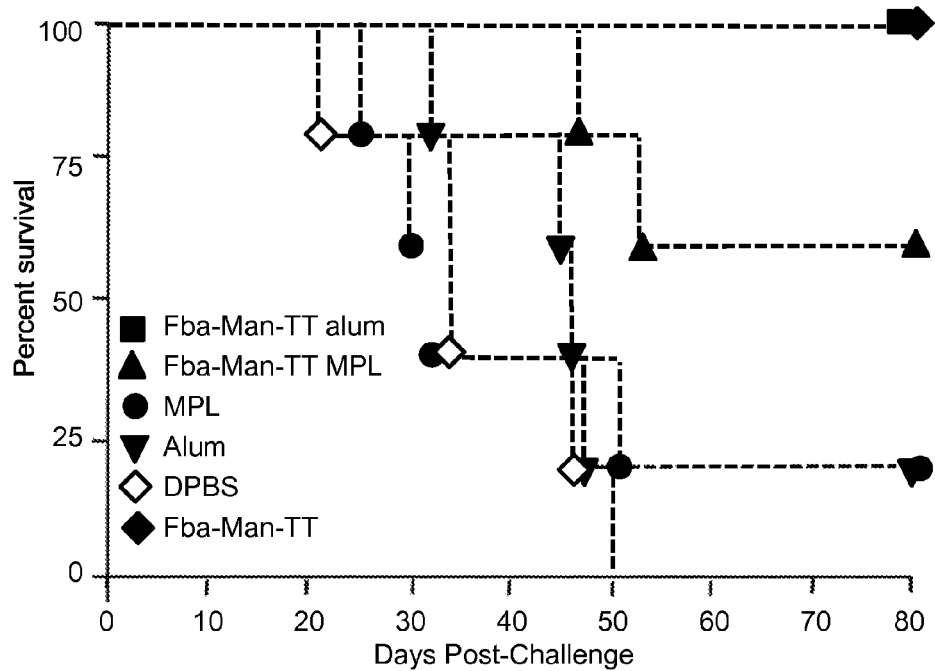
Figure 25D:
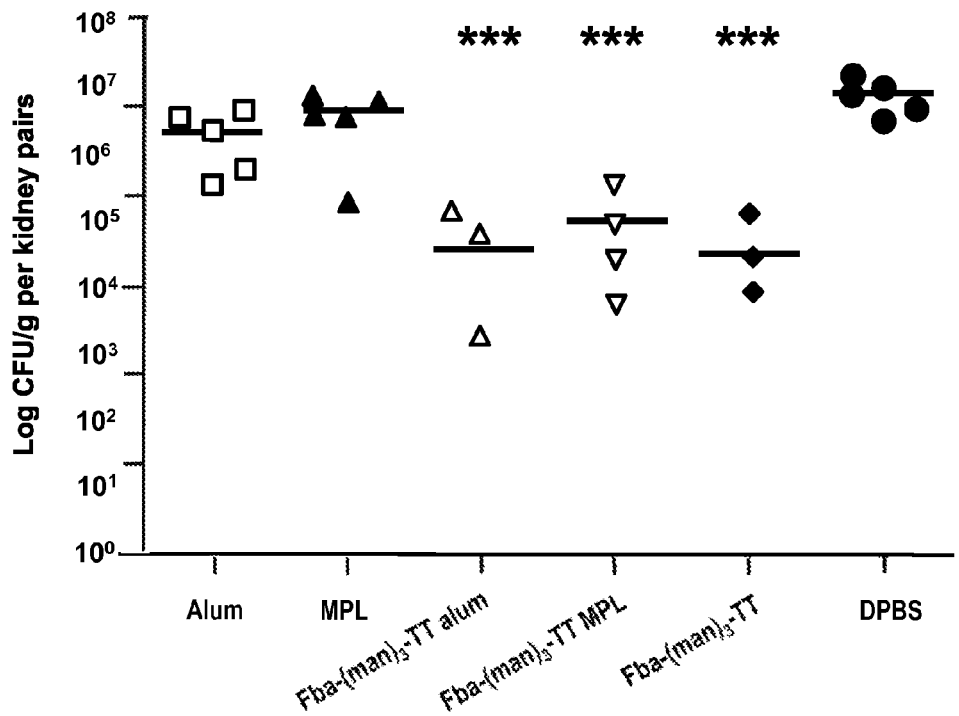

FIGS. 25A-D show responses of mice immunized with β-(Man)$_3$-Fba-TT prepared in either alum or MPL, or without adjuvant, as compared to controls. FIGS. 25A and 25B are antibody responses as seen in ELISA plates coated with Fba peptide (FIG. 24A) or the β-(Man)$_3$ (FIG. 24B). FIG. 25C shows the percent survival of the mice, and FIG. 25D shows the CFUs per kidney pairs.

Figure 26A:
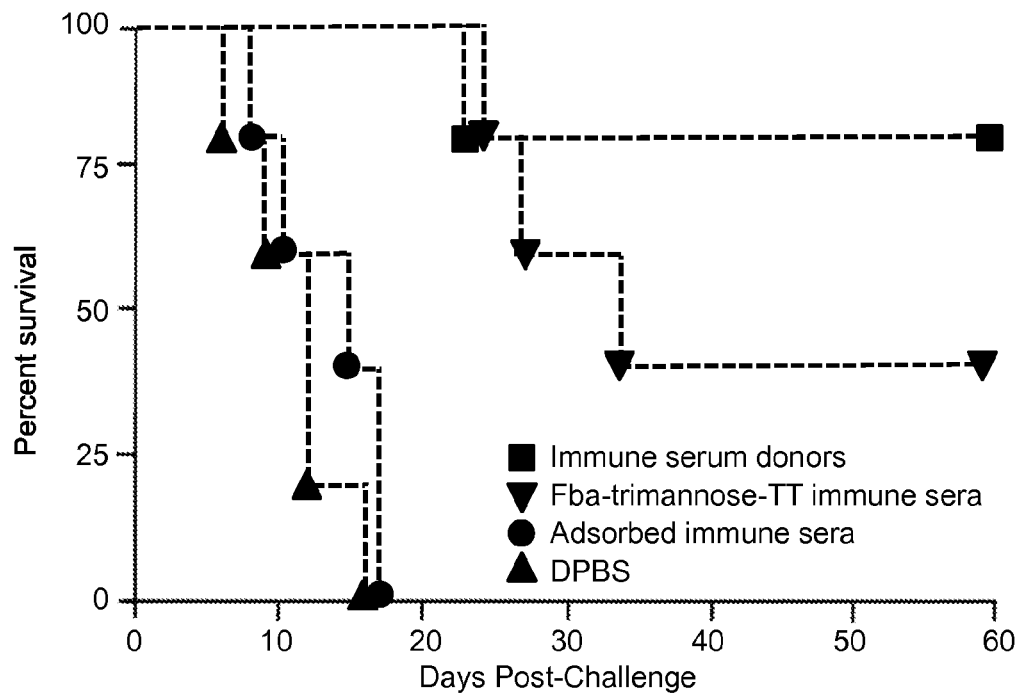
Figure 26B:
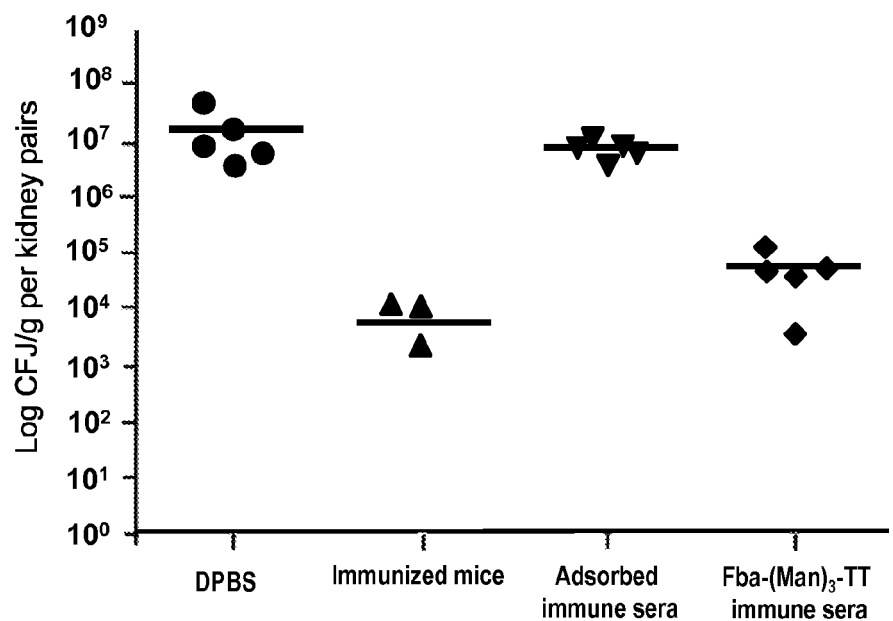

FIGS. 26A and 26B show the responses of naïve mice given sera from mice immunized with β-(Man)$_3$-Fba-TT by the DC/CFA method and the sera given i.v. prior to a challenge with a lethal dose of *C. albicans* strain 3153A, as compared to control groups were given either immune sera pre-absorbed with live *C. albicans* yeast cells or DPBS buffer prior to the challenge or the immunized mice. FIG. 26A shows the percent survival in the groups. FIG. 26B shows the fungal counts (CFU) in their kidneys.

Figure 27A:
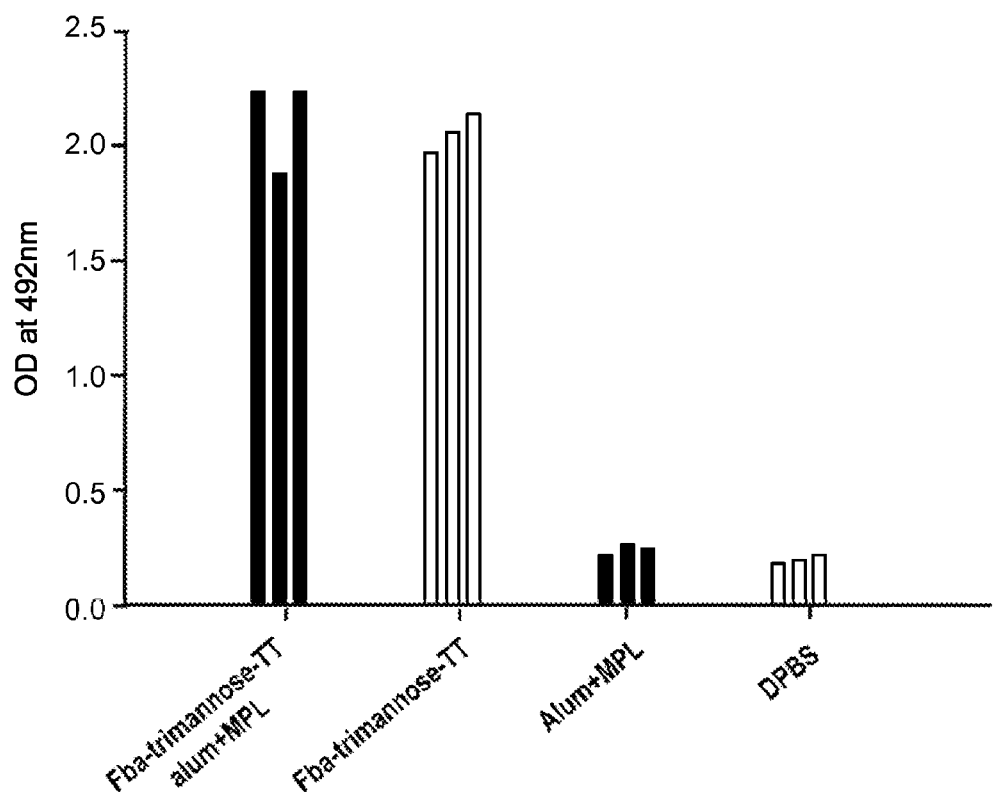
Figure 27B:
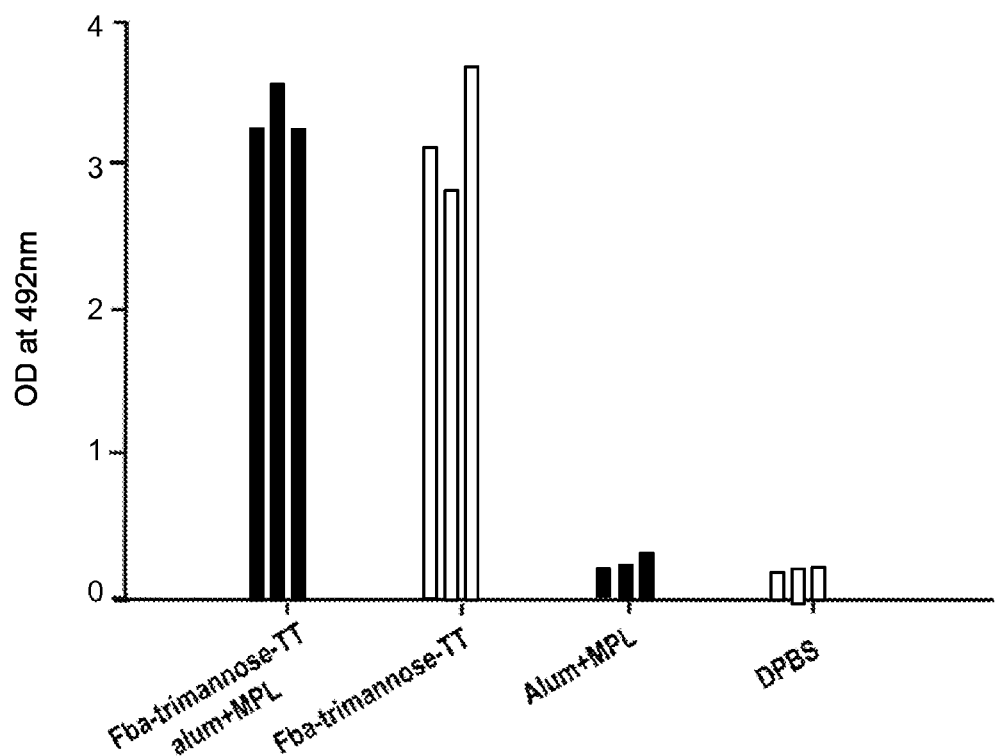
Figure 27C:
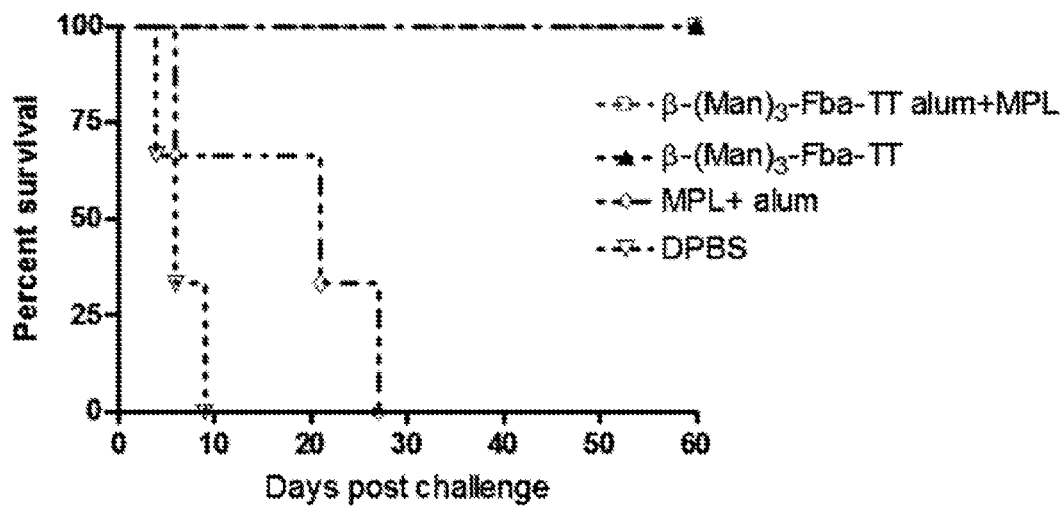
Figure 27D:
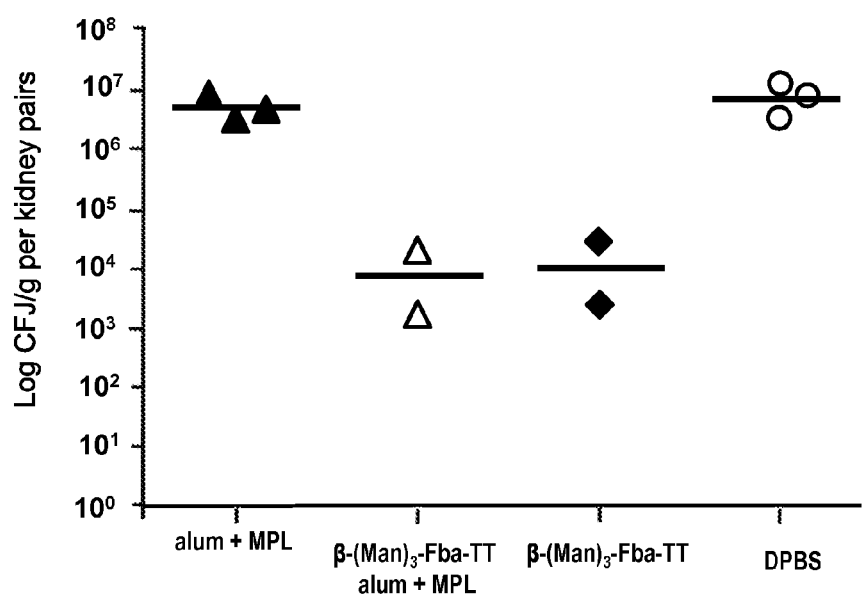

FIGS. 27A-D show responses of Swiss Webster mice immunized with β-(Man)$_3$-Fba-TT prepared in either alum or MPL, or without adjuvant, as compared to controls. FIGS. 27A and 27B are antibody responses as seen in ELISA plates coated with Fba peptide (FIG. 27A) or the β-(Man)$_3$ (FIG. 27B). FIG. 27C shows the percent survival of the mice, and FIG. 27D shows the CFUs per kidney pairs.

Figure 28A:
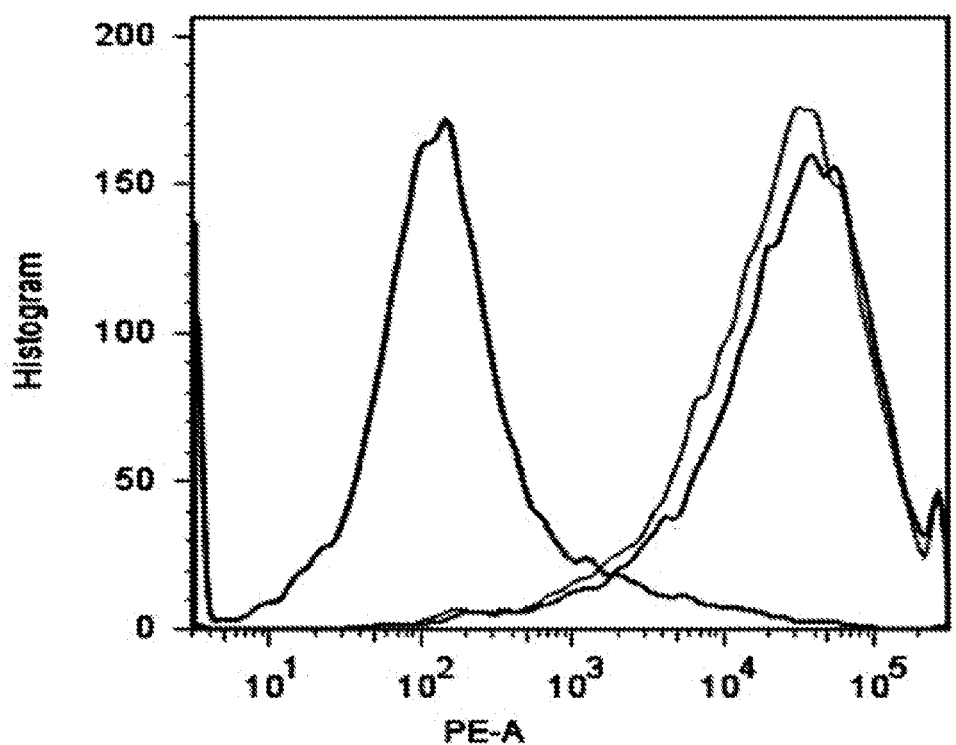
Figure 28B:
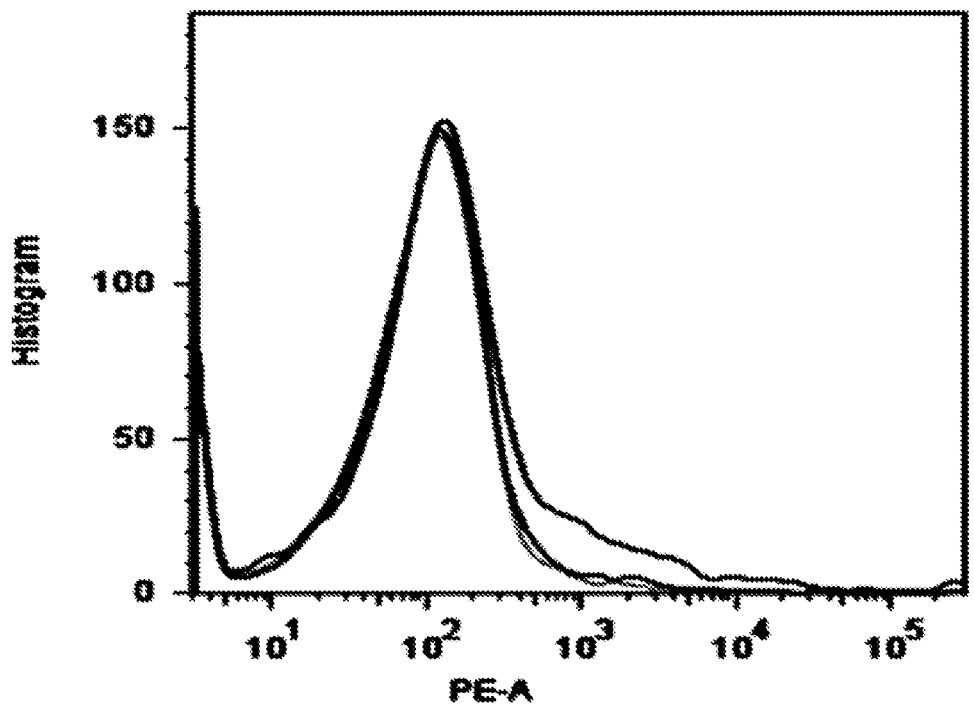
Figure 28C:
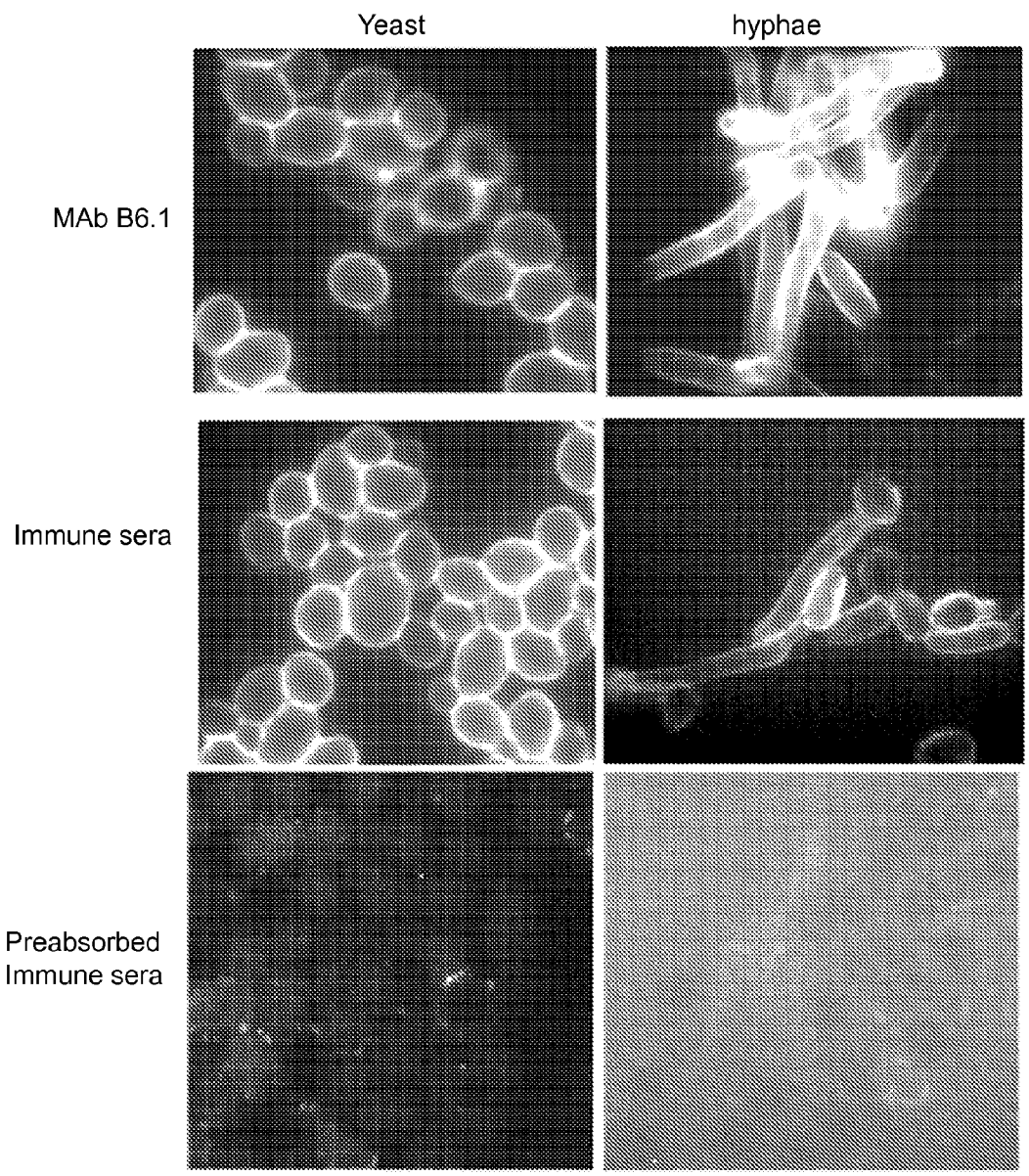

FIGS. 28A-C show results from immune serum from β-(Man)$_3$-Fba-TT vaccinated mice analyzed to detect the presence of the vaccine epitopes on the surface of C. albicans. FIG. 28A show results of flow cytometry using control serum and MAb-B6.1. FIG. 28B shows results using pre-absorbed MAb B6.1 and pre-absorbed immune sera. FIG. 28C are micrographs from confocal microscopic analyses to detect the vaccine epitopes on the surface of yeast forms and on the surface of hyphal forms of C. albicans. MAb B6.1, which is specific for β-(Man)$_3$, was used as a positive immunofluorescence control, and as a negative control, immune serum preabsorbed with C. albicans 3153A yeast cells was used.

Figure 29:
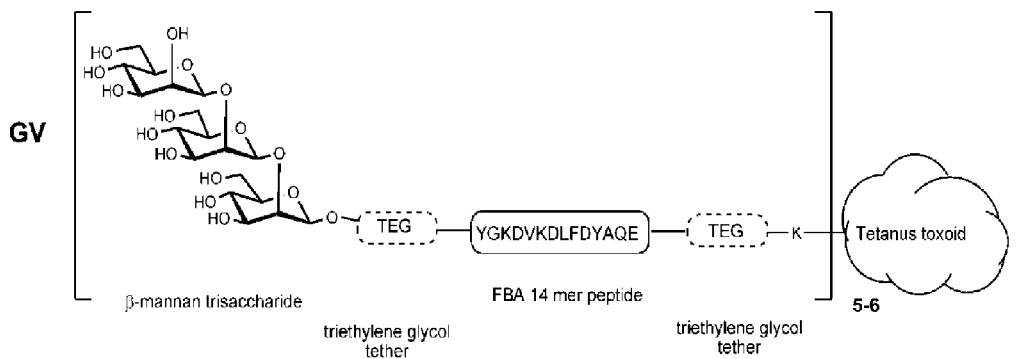
Figure 29:
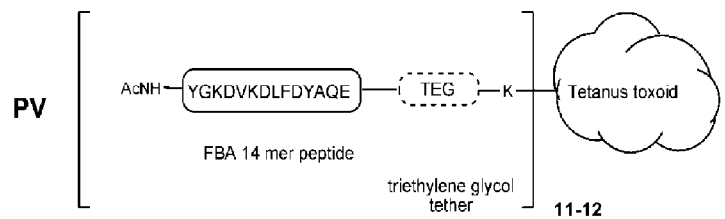
Figure 29:
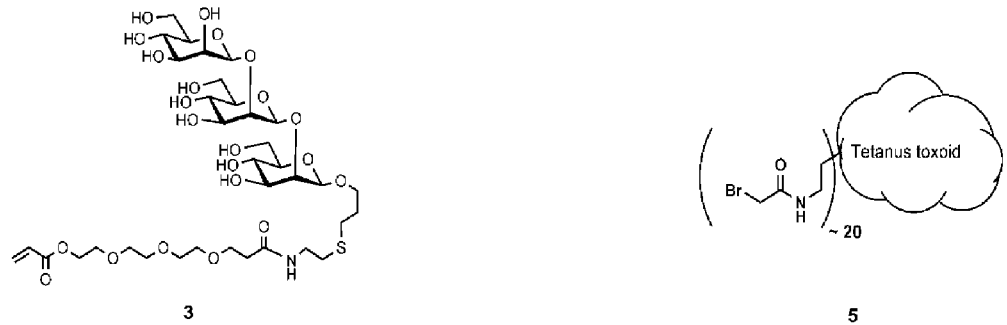
Figure 29:
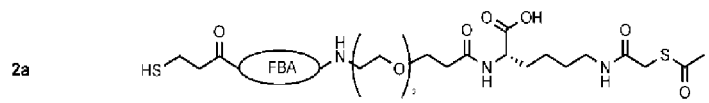
Figure 29:
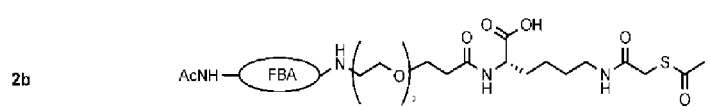
Figure 30A:
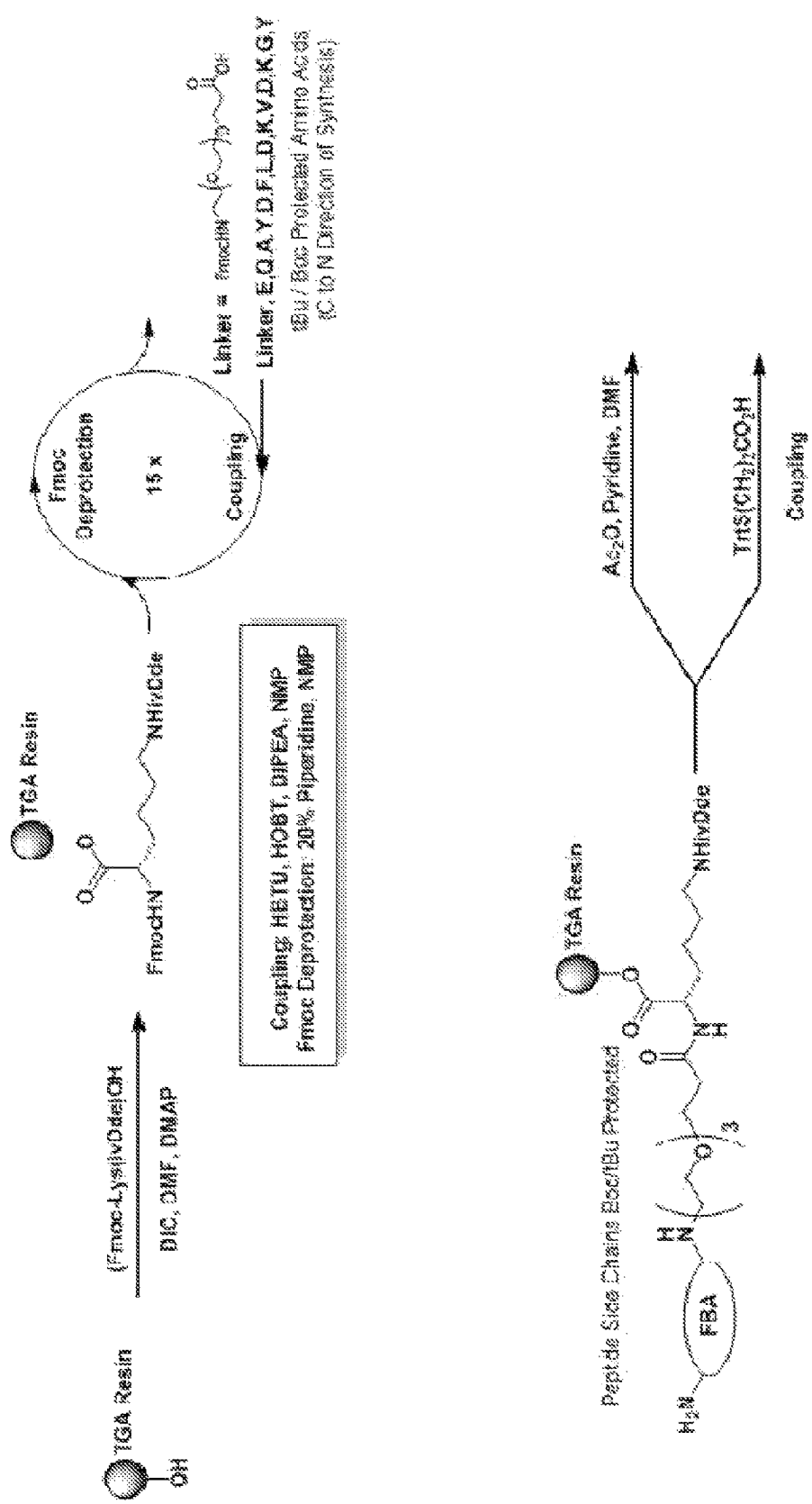
Figure 30B:
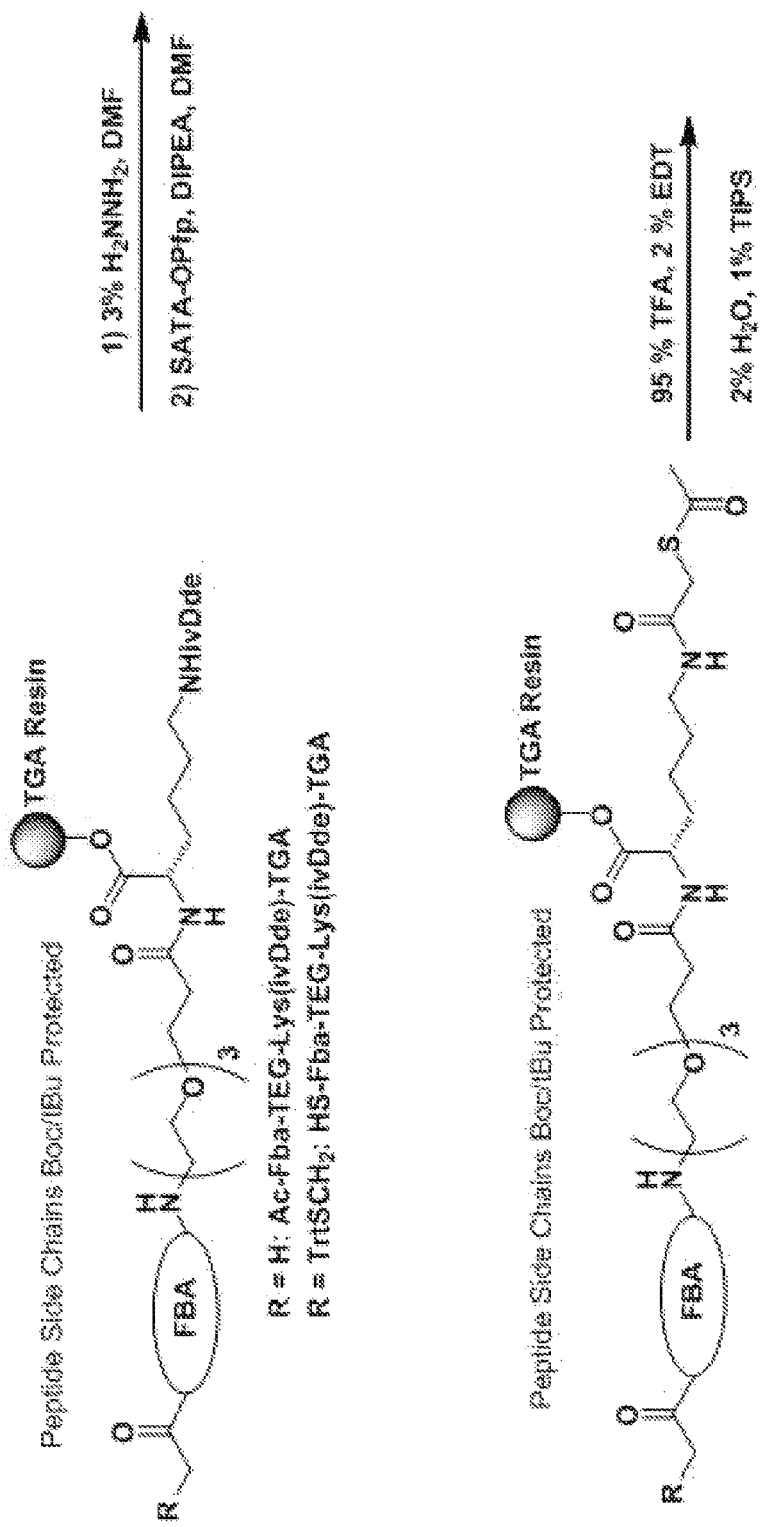
Figure 30C:
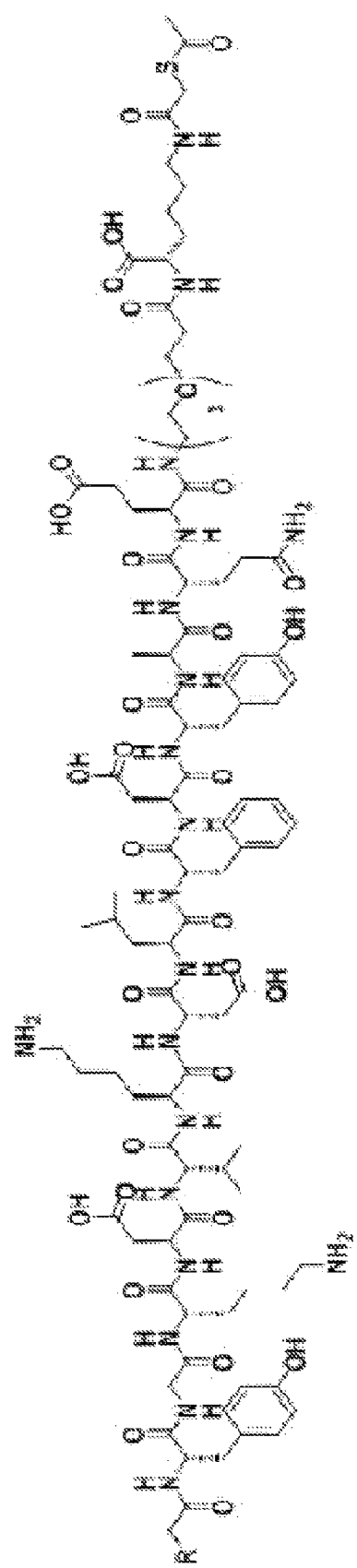
Figure 30D:
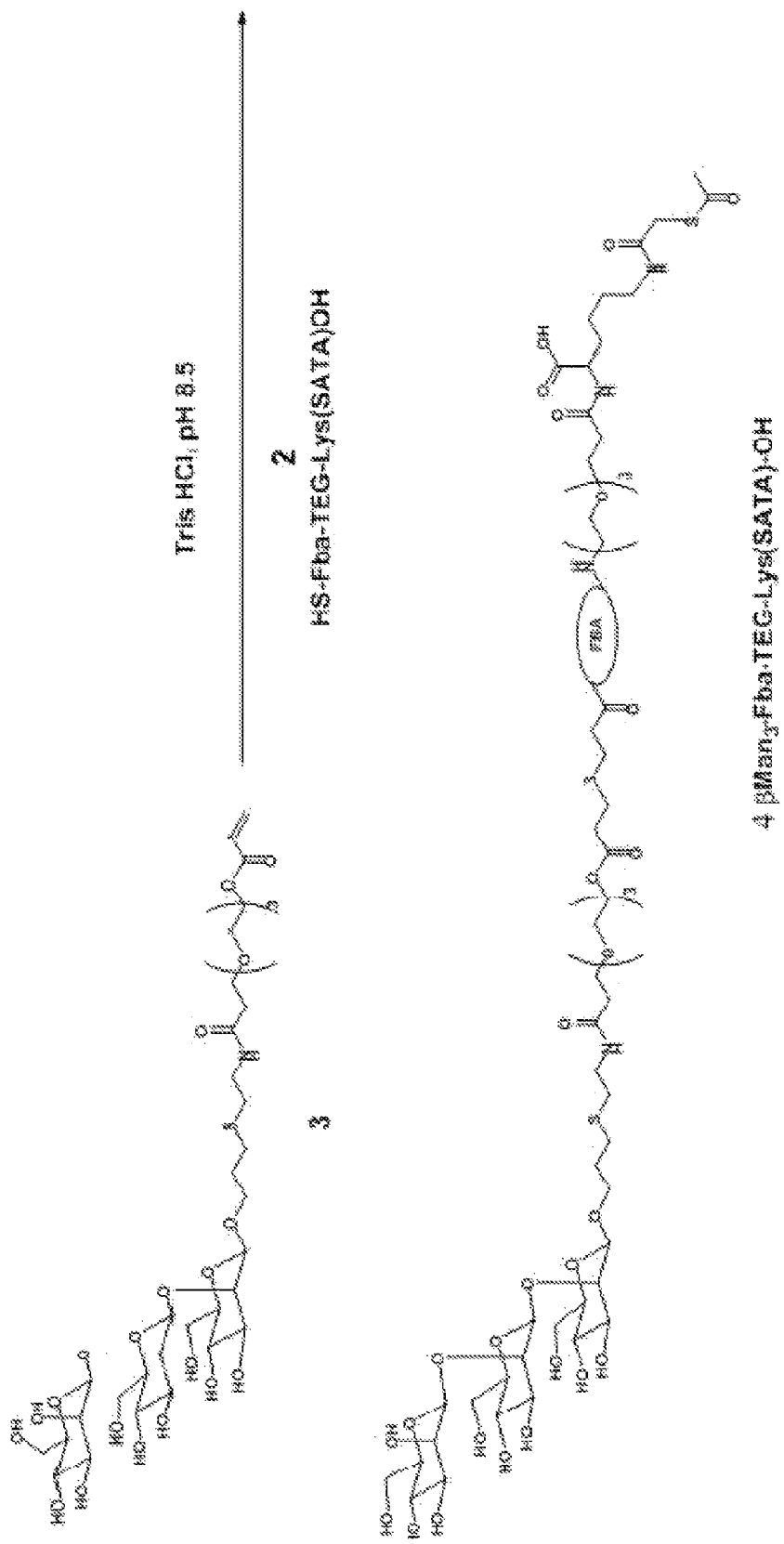
Figure 30E:
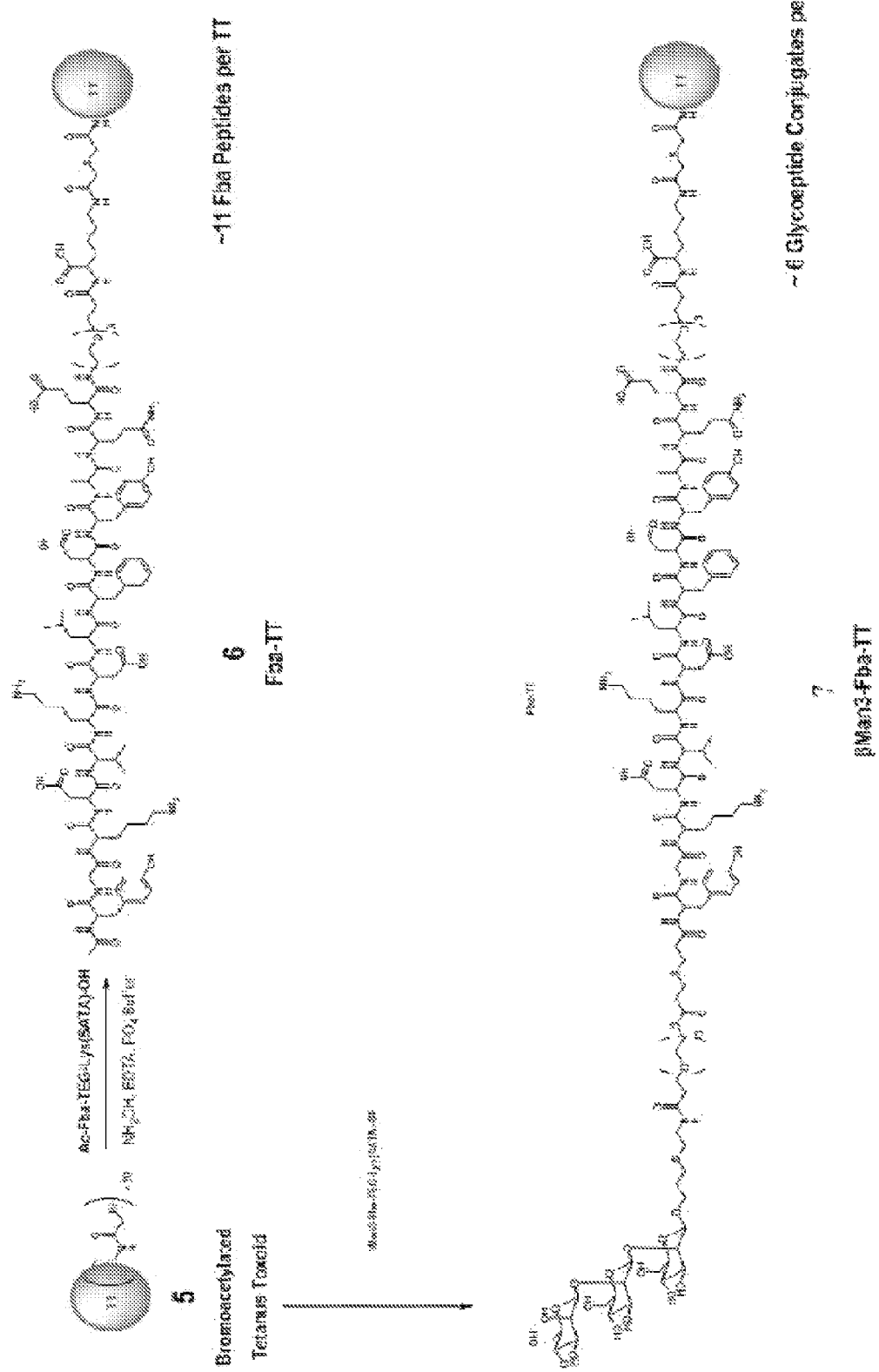

FIG. 29 shows the building blocks for the synthesis of either the glycoconjugate vaccine (GV) or the peptide vaccine lacking the mannotriose component (PV).

FIGS. 30A-30E further illustrate the synthesis of the glycoconjugate vaccine (GV) or the peptide vaccine lacking the mannotriose component (PV).

MODES FOR CARRYING OUT THE INVENTION

Previously we showed antibodies specific for the glycan β-1,2-mannotriose [β-(Man)$_3$] on the cell surface of Candida albicans protect mice against disseminated candidiasis. Furthermore, six 14 mer peptides that are within the N-terminal portion of C. albicans wall proteins were conjugated to the glycan in an attempt to create immunogenic glycopeptide conjugates. By a dendritic cell (DC)-based immunization approach, all were immunogenic and three of the six conjugates induced a high degree of protection in mice. Interestingly, whereas all six peptides induced antibody responses when used alone to pulse DCs for subsequent immunizations, three peptides induced protection and one in particular, peptide Fba (derived from fructose-bisphosphate aldolase), induced robust protective responses and was the focus of the current work. We have now shown as described below that the Fba peptide is not MHC II-restricted as it induced anti-Fba antibodies in mice of different H-2 haplotypes and in rabbits. Furthermore, the peptide induced protection against disease caused by different C. albicans strains. Partial protection was achieved when alum was used in place of DCs for Fba immunizations. Passive transfer of immune sera from Fba vaccinated mice, but not immune serum preabsorbed with fungal cells, conferred protection in naïve mice. We also show that a monoclonal antibody specific for the Fba peptide, E2-9 (IgM), protected mice against candidiasis, and could provide short term protection from candidiasis infection. This monoclonal antibody, or monoclonal antibodies isolated from the other new peptides, could be used with other antifungal compounds to protect against a Candida infection.

We have also designed vaccines for use against additional fungal diseases based on Fba and Met6, and have named these peptides Fba2 (SEQ ID NO:7), Fba3 (SEQ ID NO:8), Fba4 (SEQ ID NO:9), and Met6-2 (SEQ ID NO:10). These all had some efficiency as vaccines, although Fba2 was somewhat less efficacious. We then modified the sequence of Fba by methylating amino acids at various positions (SEQ ID NOS: 11-19) or by adding two cysteine residues (SEQ ID NO:20), as shown in Table 1 below. These modified Fba peptides also showed effectiveness as vaccines. These peptides can also be administered with a protein carrier, e.g., tetanus toxoid, or with adjuvants to increase the effectiveness as vaccines. Several peptide vaccines, including peptides from Streptococcus and Cholera, have been covalently linked to tetanus toxin (63, 64, 65) or to tetanus T$_H$ epitopes (e.g., U.S. Patent Application Publication No. 2004/0101534).

We have also modified the β-(Man)$_3$-Fba conjugate previously reported (53) by coupling it to tetanus toxoid (TT) in order to improve immunogenicity and allow for use of an adjuvant suitable for human use. By new immunization procedures entirely compatible with human use, the modified β-(Man)$_3$-Fba-TT was administered either alone or as a mixture made with alum or monophosphoryl lipid A (MPL) adjuvants and given to mice by a subcutaneous (s.c.) route. Mice vaccinated with or, surprisingly, without adjuvant responded well by making robust antibody responses. As shown below, the immunized groups showed a high degree of protection against a lethal challenge with C. albicans as evidenced by increased survival times and reduced kidney fungal burden as compared to control groups that received only adjuvant or DPBS buffer prior to challenge. To confirm that induced antibodies were protective, sera from mice immunized against the β-(Man)$_3$-Fba-TT conjugate transferred protection against disseminated candidiasis to naïve mice, whereas C. albicans-absorbed immune sera did not. Similar antibody responses and protection induced by the β-(Man)$_3$-Fba-TT vaccine was observed in inbred BALB/c and outbred Swiss Webster mice. The addition of TT to the glycopeptide conjugate resulted in a self-adjuvanting vaccine that promotes robust antibody responses without the need for additional adjuvant, which is novel and represents a major step forward in vaccine design against disseminated candidiasis. We believe that conjugates based on the addition of β-(Man)$_3$ and TT to the other peptides discussed above will make self-adjuvanting vaccines that will promote antibody responses and protection against fungal infections or diseases.

Miscellaneous:

The term "vaccine" refers to a composition or compound (an antigen) used to stimulate an immune response in a mammal and so confer resistance to the disease or infection in that mammal, including an ability of the immune system to remember the previously encountered antigen. Antibodies are produced as a result of the first exposure to an antigen and stored in the event of subsequent exposure.

The term "adjuvant" refers to non-antigenic substance (such as aluminum hydroxide and monophosphoryl lipid A) that, in combination with an antigen, enhances antibody production by inducing an inflammatory or other non-defined response, which leads to a local influx of antibody-forming cells. Adjuvants are used therapeutically in the preparation of vaccines, since they increase the production of antibodies against small quantities of antigen, lengthen the period of antibody production, and tend to induce memory cell responses.

The term "immune response" refers to the reaction of the body to foreign or potentially dangerous substances (antigens), particularly disease-producing microorganisms. The response involves the production by specialized white blood cells (lymphocytes) of proteins known as antibodies, which react with the antigens to render them harmless. The antibody-antigen reaction is highly specific. Vaccines also stimulate immune responses.

The term "immunologically effective amount" refers to the quantity of an immune response inducing substance required to induce the necessary immunological memory required for an effective vaccine.

The pharmaceutical compositions of the present invention are advantageously administered in the form of injectable compositions. A typical composition for such purpose comprises a pharmaceutically acceptable carrier. For instance, the composition may contain human serum albumin in a phosphate buffer containing NaCl. Other pharmaceutically acceptable carriers include aqueous solutions, non-toxic excipients, including salts, preservatives, buffers and the like (REMINGTON'S PHARMACEUTICAL SCIENCES, 15th Ed., Easton ed., Mack Publishing Co., pp 1405-1412 and 1461-1487 (1975) and THE NATIONAL FORMULARY XIV, 14th Ed., American Pharmaceutical Association, Washington, D.C. (1975), both hereby incorporated by reference). Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. The pH and exact concentration of the various components the pharmaceutical composition are adjusted according to routine skills in the art. Goodman and Gilman, THE PHARMACOLOGICAL BASIS FOR THERAPEUTICS (7th ed.).

Typically, such vaccines are prepared as injectables, either as liquid solutions or suspensions; solid forms suitable for solution in, or suspension in, liquid prior to injection may also be prepared. The preparation also may be emulsified. The active immunogenic ingredient is often mixed with an excipient that is pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH-buffering agents, adjuvants or immunopotentiators that enhance the effectiveness of the vaccine.

Adjuvants may increase immunoprotective antibody titers or cell mediated immunity responses. Such adjuvants could include, but are not limited to, Freund complete adjuvant, Freund incomplete adjuvant, aluminium hydroxide, dimethyldioctadecylammonium bromide, Adjuvax (Alpha-Beta Technology), Imject Alum (Pierce), Monophosphoryl Lipid A (Ribi Immunochem Research), MPL+TDM (Ribi Immunochem Research), Titermax (CytRx), toxins, toxoids, glycoproteins, lipids, glycolipids, bacterial cell walls, subunits (bacterial or viral), carbohydrate moieties (mono-, di-, tri-tetra-, oligo- and polysaccharide) various liposome formulations or saponins. Alum is the adjuvant currently in use for human patients. Combinations of various adjuvants may be used with the conjugate to prepare the immunogen formulation.

The vaccines are conventionally administered intraperitoneally, intramuscularly, intradermally, subcutaneously, orally, nasally, parenterally or administered directly to the urogenital tract, preferably topically, to stimulate mucosal immunity. Additional formulations are suitable for other modes of administration and include oral formulations. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders and contain 10%-95% of active ingredient, preferably 25-70%.

The dose to be administered depends on a predetermined quantity of active material calculated to produce the desired therapeutic effect in association with the required diluent, i.e., carrier or vehicle, and a particular treatment regimen. The quantity to be administered, both according to number of treatments and amount, depends on the subject to be treated, capacity of the subject's immune system to synthesize antibodies, and degree of protection desired. The precise amounts of active ingredient required to be administered depend on the judgment of the practitioner and are peculiar to each individual. However, suitable dosage ranges are on the order of one to several hundred micrograms of active ingredient per individual subject. Suitable regimes for initial administration and booster shots also vary but are typified by an initial administration followed in one or two week intervals by one or more subsequent injections or other administration. Annual boosters may be used for continued protection.

Antifungal compounds are well known in the art, and can be organized into several groups: polyene antifungals, azoles, allylamines, echinocandins, and other antifungal compounds. Examples of polyene antifungals (compounds with multiple conjugated double bonds) include amphotericin B, candicidin, nystatin, natamycin, and rimocidin. Examples of commonly used azoles (compounds with five-membered organic rings) include fluconazole, itraconazole, ketoconazole, miconazole, and clotrimazole. Examples of allyamines (compounds that inhibit ergosterol synthesis by inhibiting squalene synthesis) include naftifine, terbinafine and amorolfine. Echinocandins (compounds that inhibit the synthesis of glucan in the cell wall) include anidulafungin, caspofungin, and micafungin. Other commonly used antifungal compounds include griseofulvin and 5-fluorocytosine.

Section A: Peptide Vaccines

Example 1

Materials and Methods
*Candida* Strains and Culture Conditions.
*C. albicans* 3153A and SC5314, *C. krusei* (ATCC 6258), *C. glabrata* (ATCC 2001) and *Saccharomyces cerevisiae* (ATCC 9463) were obtained from the American Type Culture Collection (ATCC; Manassas, Va.) and were grown as stationary-phase yeast cells in glucose-yeast extract-peptone broth at 37° C., washed and suspended to the appropriate cell concentration ($5 \times 10^6$/ml) in Dulbecco's PBS (DPBS; Sigma-Aldrich, St. Louis, Mo.), and used to infect mice intravenously (i.v.) as previously described (25, 29). *C. albicans* strain 3153A was also used for serum antibody absorption, immunofluorescence staining and flow cytometric analysis. Unless otherwise indicated, *C. albicans* strain 3153A was used to challenge the mice in the examples below.

Mice.
BALB/c and C57BL/6 female mice (National Cancer Institute Animal Production Program, Frederick Md.) aged from 5 to 7 weeks old were used throughout. Mice were maintained in an animal facility and all animal experiments were done in accordance with protocols approved by the Institutional Animal Care and Use committee (IACUC) at Children's Hospital Research Institute in New Orleans. Unless indicated otherwise below, BALB/c mice were used in the experiments.

Isolation and Culture of Dendritic Cells (DCs) from Mouse Bone Marrow.
Dendritic cells (DCs) were generated from mouse bone marrow by a previously described method (49, 53). Briefly, donor mice were euthanized by $CO_2$ asphyxiation, their long bones and tibias were aseptically removed, bone marrow was flushed from the bones by forcibly injecting several ml of RPMI-1640, and clumps were removed or dispersed by gentle pipetting through a sterile 70-mm cell strainer. Red blood cells were lysed (ACK lysing buffer, 0.15 M $NH_4Cl$, 1.0 mM $KHCO_3$, 0.1 mM EDTA) for 4 min, and the remaining bone marrow cells were suspended in complete medium

[CM, RPMI-1640 supplemented with 10% FBS (FBS), 2 mM L-glutamine, 1% of nonessential amino acids, and 100 units/ml penicillin and 100 µg/ml streptomycin], adjusted to $2 \times 10^5$ cells per ml plated in 6-well plates at 5 ml per well and cultured for up to 9 days in the presence of 40 ng/ml of rmGM-CSF and rmIL-4 (R&D Systems) at 37° C., 5% $CO_2$. On days 4 and 7 of culture, the same amount of fresh GM-CSF and IL-4 was added to the wells. Unless stated otherwise, all reagents were purchased commercially from Sigma-Aldrich.

Immunizations with Peptide Pulsed Dendritic Cells.

The murine dendritic cells (DCs) were pulsed in vitro with peptide candidate vaccine antigens as previously described (53). Briefly, DCs in culture were pulsed with the peptide antigen (1 µM) on day 6. On day 7, PGE2 (10-7M) was added along with LPS (2 µg/ml, Sigma-Aldrich) for 24 h. On day 9, antigen-pulsed DCs were washed extensively and $5 \times 10^5$ in 200 µl DPBS were given intraperitoneally (i.p.) as the priming dose to mice. The mice were boosted i.p. at day 14 with fresh antigen-pulsed DCs and boosted a second time at day 28 with antigen (10 µg) emulsified in complete Freund adjuvant (CFA) given subcutaneously (s.c.).

Immunizations with Peptide Fba in Human Approved Adjuvants.

Fba peptides were administered as either a mixture made with alum (aluminum hydroxide gel, Sigma-Aldrich) or MPL (Lipid A, monophosphoryl, Sigma-Aldrich) as adjuvants. Mice were immunized by s.c. injection 100 ml of 2.5 µg of the Fba peptide with either 50 µg alum or 10 µg MPL on days 1, 21 and 42. Sera from groups of mice given DPBS buffer or adjuvant only were used as negative controls.

Serological Assays.

Sera were ELISA analyzed for antibody titers. For DC-based immunization, control groups consisted of mice given DCs alone at the time of priming and first booster followed by CFA alone at the time of the second booster, or DPBS alone for all three injections. For Fba peptides administered with alum or MPL, control groups were mice given adjuvant alone or DPBS buffer. Fba peptide was conjugated to a multiple antigenic peptide (MAP), of which the lysine core displayed approximately eight copies of the Fba peptide epitope. Synthetic Fba-MAP (GenScript) was dissolved at 5 µg/ml in PBS (pH 7.4) and used to coat 96-well ELISA plates for testing duplicate serial 2-fold dilutions of samples of each immune serum and control sera. Color development for each well was achieved by use of secondary antibody (goat anti-mouse polyvalent Ig-HRP) and substrate (O-phenylenediamine and $H_2O_2$) and OD determined at 492 nm.

Monoclonal Antibodies (MAbs).

Hybridoma clones producing MAbs E2-9 (IgM) were generated from mice vaccinated with a Fba-DCs preparation as described previously (53). Briefly, BALB/c mice were immunized by injection of synthetic Fba peptide pulsed DCs to stimulate the production of antibodies against Fba peptide as described above. Ten days after the second booster, serum was taken from each animal to determine animals with the highest anti-Fba titers for subsequent sacrificing, removal of spleens, and preparation of single cell suspensions. Hybridoma clones were established by polyethylene glycol facilitation of fusion of spleen cells to an SP2/0-AG14 myeloma cell line by standard protocols. Hybridoma clones were screened by ELISA for production of specific anti-Fba antibody; only the highest titers and most rapidly growing clones were selected for subsequent cloning×3 or more by limiting dilution. Clone E2-9 produced MAb designated as MAb E2-9 that was reactive with the Fba peptide, as determined by ELISA inhibition with synthetic Fba peptide by methods described below.

The hybridoma cell lines were initially grown in antibiotic-free RPMI 1640 medium (Sigma) supplemented with 10% fetal bovine serum (Invitrogen) and 2 mM L-glutamine (Sigma) at 37° C. in the presence of 5% $CO_2$. For antibody production, the hybridoma clones were grown in antibiotic-free, BD cell MAb serum-free medium (but containing 1.1 mg bovine serum albumin/ml) in a CELLine device (BD, Bedford, Mass.) and concentrated by using centrifugal filter devices (Centricon Plus-80; Millipore Corporation, Bedford, Mass.). MAb concentration was determined by measuring the absorbance at 280 nm ($A_{280}$) of the sample, and purity was estimated by analysis on a 10-12.5% SDS-PAGE gel.

Inhibition ELISA.

The specificity of MAb E2-9 for Fba peptide was determined by an inhibition ELISA as described previously (52, 53). Briefly, Fba-MAP was dissolved in DPBS (5 µg/ml), and the solution was used to coat 96-well ELISA plates (100 µl, overnight at 4° C.). The wells were washed five times with PBST (PBS containing Tween 20, 0.05% [vol/vol] and blocked with 1% bovine serum albumin-PBST. MAb E2-9 produced as described above, was serially diluted up to 10,000 for ELISA measurements. Unless otherwise stated, the serum was diluted 1:100 dilution in DPBS to determine the content of antibody by ELISA. MAb E2-9 was mixed with Fba peptide (inhibitor) (dissolved in PBST at a concentration between 0.1 µM and 1 mM), and the resulting solution of each concentration was added to the Fba-MAP coated microtiter wells (solid phase) in triplicate and incubated at 21 to 23° C. for 2 h. Unless otherwise stated, the concentration of test antigens used to coat the wells was about 5-10 µg/ml. The wells were washed three times with PBST, and goat anti-mouse heavy chain specific for IgM was HRP-conjugated (diluted 1:10,000 in PBST) (Sigma) and 100 µl was added to the corresponding wells and incubated for 1 h at 21 to 23° C. The wells were washed five times with PBST, followed by addition of 100 µl of substrate solution (25 ml of 0.05 M phosphate-citrate buffer [pH 5.0], 200 µl of an aqueous solution of O-phenylenediamine 50 mg/ml [Sigma], and 10 µl of 30% H2O2). Color was allowed to develop for 10 min, stopped by addition of 100 µA of 2 M H2SO4, and read at 492 nm (microtiter plate reader, model 450; Bio-Rad, Richmond, Calif.). The percent inhibition was calculated relative to wells containing antibody without inhibitor.

SDS-PAGE.

MAb E2-9 was evaluated by sodium dodecyl sulfate-polyacrylamide gel electrophoresis (SDS-PAGE) (12.5% polyacrylamide) analysis under reducing (β-mercaptoethanol) conditions to determine sizes of heavy and light chains of the antibody. The IgM pentamer of E2-9 was shown by western blot of an SDS-PAGE gel under non-reducing SDS-PAGE (2.5% acrylamide/bis & 0.5% agarose) conditions. Following separation by SDS-PAGE, the proteins were transferred to a PVDF membrane (Bio-Rad). The membrane was blocked for 2 h with 5% non-fat milk dissolved in PBST (pH 7.4). The membrane was washed in PBST (pH7.4) and probed with horseradish-peroxidase-conjugated secondary Abs. A positive signal was visualized using the ECL system (Perkin Elmer).

Immunofluorescence and Flow Cytometric Analysis.

Distribution of the Fba peptide epitope on yeast cells was determined by indirect immunofluorescence. Two hundred microliters of MAb E2-9 (at 16 µg Ab protein/ml of DPBS) was added to a pellet of *C. albicans* yeast cells ($5 \times 10^6$) that was prewashed with DPBS three times. The yeast cells were suspended in the antibody preparation and incubated while shaking by rotation at room temperature (RT, 22-24° C.) for 1-2 h. After incubation, the yeast cells were washed with DPBS three times, suspended in 200 μl of fluorescein-labeled goat anti-mouse IgM (u-chain specific; Sigma) (stock solution, 1 mg/ml; working solution, 20 μg/ml of DPBS) and incubated at RT as described above for 0.5 h. The yeast cells were washed with DPBS three times and suspended in 200 μl of DPBS. The cells were observed by confocal microscopy (LSM 510, Zeiss). The distribution of the Fba peptide epitope on the yeast cell surface was compared to that obtained with yeast cells fluorescently stained for detection of the MAb B6.1 epitope. Negative controls included testing of an irrelevant isotype control IgM MAb S-9 (45) and use of fluorescein-labeled goat anti-mouse secondary antibody only. For flow cytometric analysis, following the last incubation, cells were washed as described above and suspended in the 500 μl DPBS buffer. Flow cytometry was performed using a BD Biosciences FACSVantage SE equipped with an argon laser excitation at 488 nm. 10,000 cells in each sample were analyzed (CellQuest Pro software).

Fungal Challenge and Assessment of Protection.

Two weeks after the second boost, immune and control mice were infected intravenously (i.v.) with a lethal dose of live C. albicans yeast cells ($5\times10^5$ in 0.1 ml of DPBS) prepared as described above and as before (53). Passively immunized mice (below) also received the same challenge dose. Protection was evaluated by monitoring animal survival for 80-100 days. The mice were monitored 2-3 times daily for the development of a moribund state, defined as being listless, disinterested in food or water, and nonreactive to finger probing. At the time that a mouse was deemed moribund, it was sacrificed and their kidneys (for some experiments, brains) were homogenized in DPBS and plated onto a nutrient agar to determine colony forming units (CFUs). After 80-100 days, the experiments were terminated and all the survivors at that time were sacrificed and their kidneys were assessed for CFU as before. The lowest limit of detection for the CFU assay was 50 CFU per kidney pair.

Passive Transfer of Polyclonal Antibodies (PAbs).

To determine if antibodies in the sera from vaccinated mice were responsible at least in part for the protection induced by active immunization, polyclonal antisera (PAbs) were obtained from vaccinated mice and pooled. Pooled immune sera from Fba pulsed DCs immunized mice were ELISA titered as described above. The pooled PAb were stored at −20° C. or absorbed with C. albicans yeast cells and stored. For the transfer of rabbit anti-Fba sera, one mouse group received pre-immune rabbit serum was used as an additional control. For testing, mice received 0.5 ml i.p. full-strength immune serum or control serum. Four hours later, all mice were challenged i.v. with C. albicans ($5\times10^5$ yeast cells). All animals received a second dose (100-200l) of serum or buffer i.p. 24 h after the first dose.

Passive Transfer of MAbs by Intraperitoneal (i.p.) Route.

The preventive effect of MAbs E2-9 was examined by the same injection schedules as above for experiments on PAbs. Control mice received equivalent volumes of the DPBS diluent. The concentrated MAb E2-9 preparation was diluted in DPBS to give an ELISA titer of 10,000 against Fba-MAP-coated microtiter plates, which is approximately equal to 16 μg/ml antibody. Prior to mouse injections, antibody solutions were spun at 15,000×g for 15 min to remove possible antibody aggregates. The negative control materials tested in mice were MAbs absorbed with C. albicans yeast cells and DPBS. For each condition, 6- to 8-week-old female BALB/c mice (Jackson Laboratories) were given 0.5 ml of test MAb, or control materials intraperitoneally, followed 4 h later by 0.1 ml intravenously of a suspension containing $5\times10^6$ yeast cells per milliliter of DPBS.

Statistical Analysis.

Median survival times were statistically evaluated by Kaplan-Meier (GraphPad Prism, version 4). In all analyses, there were five mice per group (n=5) and a two-tailed t test was used, and most all experiments were repeated at least twice.

Example 2

Vaccination with Three Synthetic Peptides Induced Antibody Production and Protection Against Disseminated Candidiasis in Mice C. albicans carrier peptides were selected from cell wall proteins that are expressed during pathogenesis of human disseminated candidiasis (11, 46, 53). We selected six candidate carriers, each of which was comprised of 14 amino acids located near the N-terminus of their respective complete protein presumed to be located in the cell wall of the fungus (46, 53). The six candidate carrier peptides, in parentheses, were derived from the proteins fructose-bisphosphate aldolase (Fba); methyltetrahydropteroyltriglutamate (Met6); hyphal wall protein-1 (Hwp1); enolase (Enol); glyceraldehyde-3-phosphate dehydrogenase (Gap1); and phosphoglycerate kinase (Pgk1). Each synthetic peptide was chemically conjugated to the synthetic glycan β-(Man)$_3$ to produce the six glycopeptides vaccine constructs for immunogenic testing. Three of the glycopeptide conjugates, β-(Man)$_3$-Fba, β-(Man)$_3$-Met6 and β-(Man)$_3$-Hwp1, induced a high degree of protection as evidenced by survival and low kidney fungal burden following challenge with a lethal dose of C. albicans (53). These prior results led us to consider whether protection was also contributed by responses to the carrier peptides. By an antigen-pulsed dendritic cell (DC)-based vaccine strategy favoring production of antibodies as described before (49, 53) and described above, all six peptides were tested and results shown in FIG. 1A.

Figure 1A:
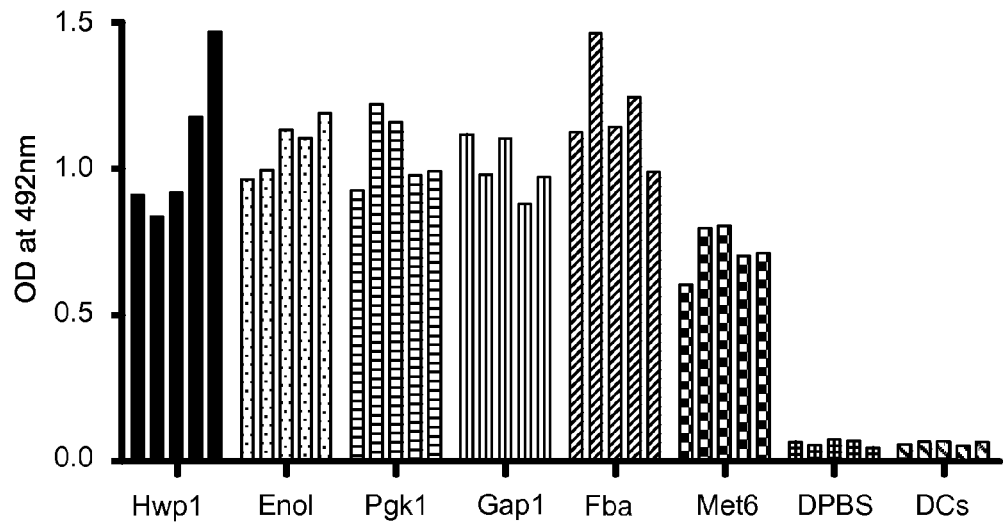
FIG. 1A shows the antibody responses as tested by ELISA in BALB/c mice 14 days after a second booster immunization using peptide-pulsed DC vaccines based on six synthetic peptide carriers. Control groups consisted of mice given the same regimen for priming and boosters except that the peptides were omitted (DCs+CFA; DCs for first and second doses and CFA for the last dose) or DPBS only at each injection time.
Figure 1B:
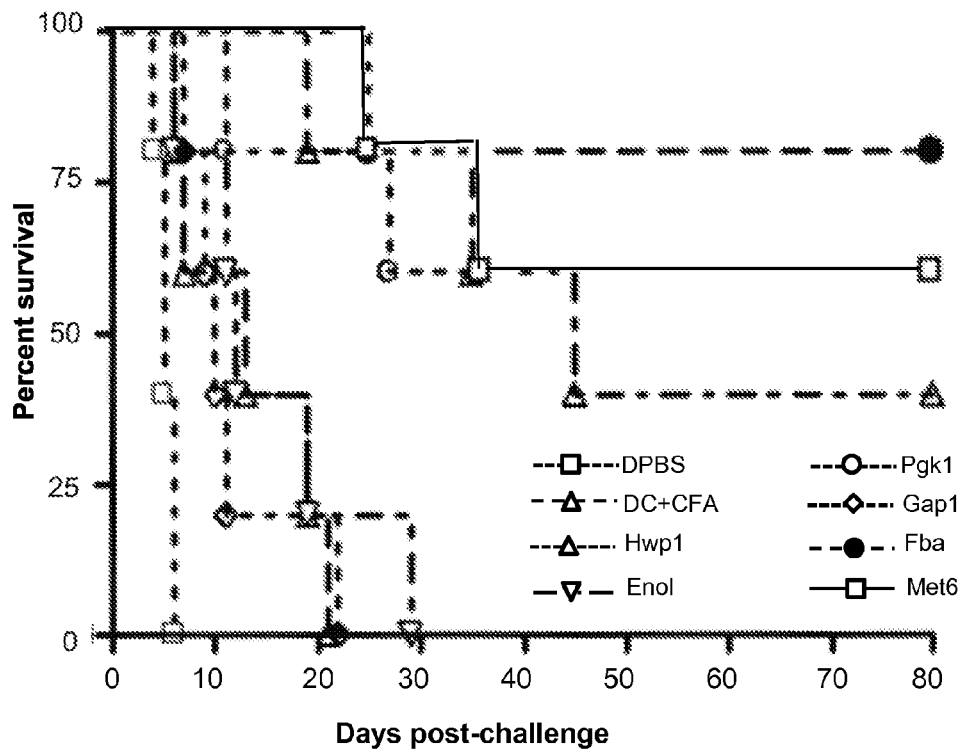
FIG. 1B shows percent survival in BALB/c mice immunization using peptide-pulsed DC vaccines based on six synthetic peptide carriers, and challenged with a lethal dose of live C. albicans.
Figure 1C:
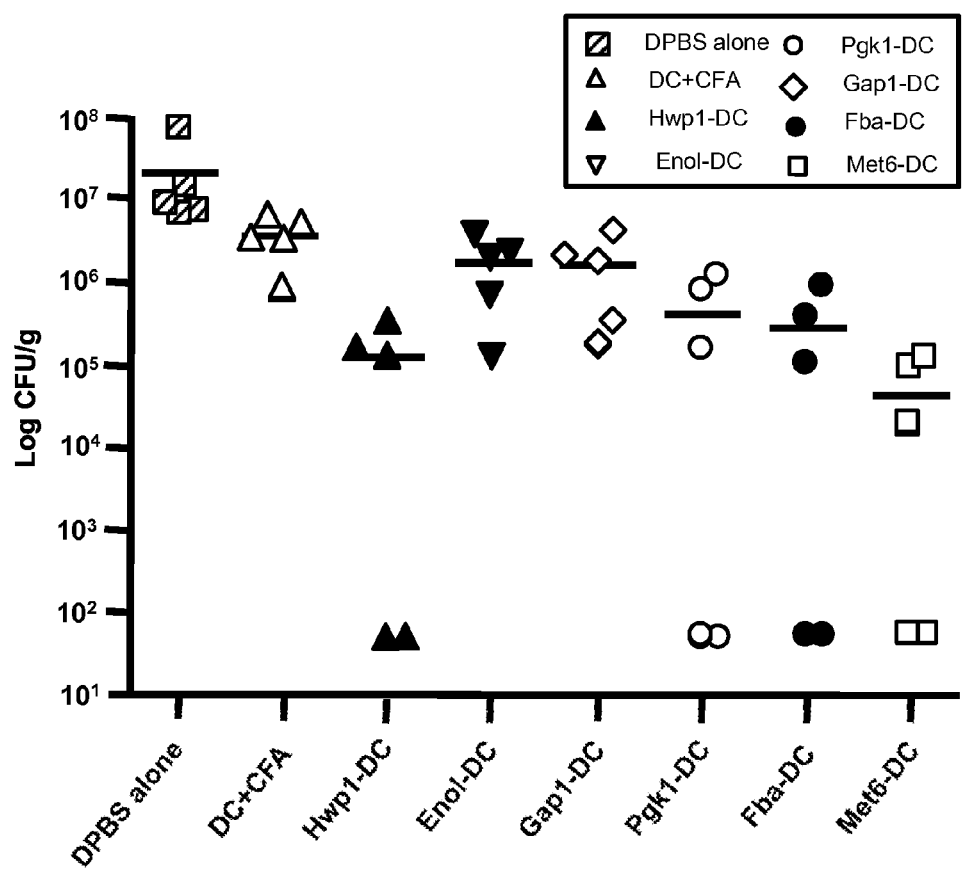
FIG. 1C shows the number of viable fungal colony forming units (CFUs) per kidney pairs from mice immunized with the six peptides as compared to either of the control groups ($p<0.001$). The bars of each panel indicate mean CFUs per kidney pair for each group. The lowest limit of detection for the CFU assay is 50 CFU per kidney pair.

FIGS. 1A-1C show the antibody responses in BALB/c mice against peptide-pulsed DC vaccines. Sera from mice immunized with the six synthetic peptide carriers presented on dendritic cells (DCs) for the priming and first booster immunizations and emulsified in complete Freund adjuvant (CFA) for the second booster were tested by ELISA for antibody responses against the peptides. Control groups consisted of mice given the same regimen for priming and boosters except that the peptides were omitted (DCs+CFA) or DPBS only was used at each injection time. FIG. 1A shows results of serum samples collected from each of the five mice per group of vaccinated animals and each of the five mice in the two control groups fourteen days after the second booster immunization, diluted 1:100 and tested by ELISA. All the peptides were able to induce antibody responses in mice. FIG. 1B shows that three peptide vaccines induced protective responses in mice against disseminated candidiasis. Following challenge with a lethal dose of live C. albicans, mice vaccinated with peptides Fba, Hwp1, and Met6 survived significantly longer than either of the control groups (P<0.05). FIG. 1C shows that mice immunized with Fba, Hwp1 and Met6 had greatly reduced or non-detectable (ND) viable fungal colony forming units (CFUs) per kidney pairs as compared to either of the control groups (p<0.001). Mice immunized with Pgk1 also had reduced or non-detectable CFUs in their kidneys as compared to controls. The bars of each panel indicate means of CFUs per kidney pair for each group. The lowest limit of detection for the CFU assay is 50 CFU per kidney pair.

All six peptides were immunogenic by themselves as shown by high titers of specific antibody to each (FIG. 1A). Peptide controls of random sequences were used and they never induced detectable specific antibody responses (data not shown). In addition, tests were negative for cross-reactivity between each of the various immune-sera and the respective unrelated peptides (data not shown). Also, each of the six antisera, but not negative control sera, reacted directly with yeast and hyphal forms of the fungus as evidenced by indirect immunofluorescence microscopy (data not shown).

Interestingly, the three carrier peptides Fba (SEQ ID NO:1), Met6 (SEQ ID NO:2) and Hwp1 (SEQ ID NO:3) induced a high degree of protection as evidenced by survival and low kidney fungal burden in mice challenged with the fungus (FIGS. 1B and 1C). The immunized groups that received the Fba, Met6 or Hwp1 peptide vaccines showed 40-80% survival throughout the 80-day post-challenge observation period and survived significantly longer as compared to DPBS or adjuvant only controls following the i.v. challenge with a lethal dose of live fungal cells. This conclusion was further strengthened by an extended observation in which neither of two other peptides Gap1, or Eno1 induced protection against disseminated candidiasis (FIG. 1B). Importantly, the survivors in groups immunized against Fba, Met6 and Hwp1 had low or even non-detectable viable fungal units (colony forming units, CFUs) in kidneys (FIG. 1C)—a target organ in disseminated candidiasis, as compared to animals that succumbed (p<0.001). Mice immunized with Gap1 or Eno1 alone resulted in a slightly less fungal burden in the kidneys as compared to non-immune mice, but the differences were not significant. Surprisingly, Pgk1 alone also induced some protection, and the immunized mice also had low or non-detectable CFUs in their kidneys as compared to controls. This was unexpected since β-(Man)$_3$-Pgk1 immunization actually enhanced disease (53).

Example 3

Fba Peptide is not an MHC II Restricted Epitope

The Fba peptide was tested in C57BL/6 mice, which is another common inbred mouse strain, but with an MHC haplotype and immunophenotype distinct from BALB/c mice (35). These two strains differ in their resistance or susceptibility to experimental disseminated candidiaisis (2-4). In addition to mouse strain differences with respect to a Th1 (C57BL/6) or Th2 (BALB/c) bias, the strains differ in the ability of macrophages to be activated (6). By the same DC-based immunization approach used for the BALB/c mice as described above, C57BL/6 mice was tested with the Fba peptide was given alone or as a glycoconjugate compared to the control groups of mice injected with DPBS buffer, or DCs+CFA. The results are shown in FIG. 2.

Figure 2:
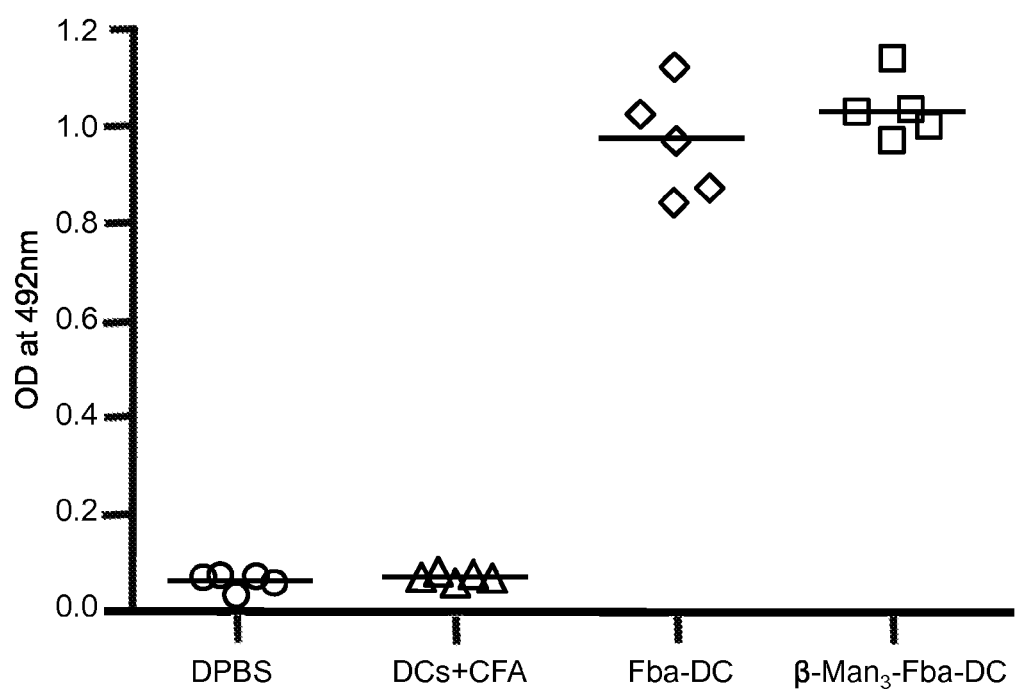
FIG. 2 shows the antibody responses as measured by ELISA in C57BL/6 mice against the Fba peptide vaccines after 14 days after the second booster.

FIG. 2 shows the antibody responses in C57BL/6 mice against the Fba peptide vaccines or controls. Fourteen days after the second booster, immune sera were tested by ELISA for antibody responses against the Fba peptide. ELISA titers, done on plates coated with synthetic peptide Fba-MAP showed relatively strong specific antibody responses against the peptide as compared to two control groups. Following the first booster immunization, an isotype switch from IgM to IgG of Fba specific antibodies was observed in the sera from immunized mice (data not shown).

To obtain enough antisera for passive transfer experiments, and to determine whether the Fba peptide is immunologically restricted in other animal species, we obtained rabbit antisera against the peptide from a commercial source (Genscript). Fba was conjugated to keyhole limpet hemocyanin (KLH) prior to the rabbit immunizations. Titers of 512,000 of anti-Fba peptide immune sera from each of two rabbits was obtained (data not shown), which offers additional evidence that the Fba peptide is not an MHC-restricted epitope, and can be immunogenic in other mammals, including humans.

Example 4

Fba-DC Vaccination Protects Mice Challenged with Different *C. albicans* Strains To test if vaccination with the Fba peptide pulsed DCs protects mice challenged with a different *C. albicans* strain, we challenged immunized mice with *C. albicans* strain SC5314 (ATCC), which is the most commonly used clinical isolate of *C. albicans* for research purposes. As a positive control, a second group of mice immunized at the same time were challenged with *C. albicans* strain 3153A. The results are shown in FIGS. 3A-3D.

Figure 3A:
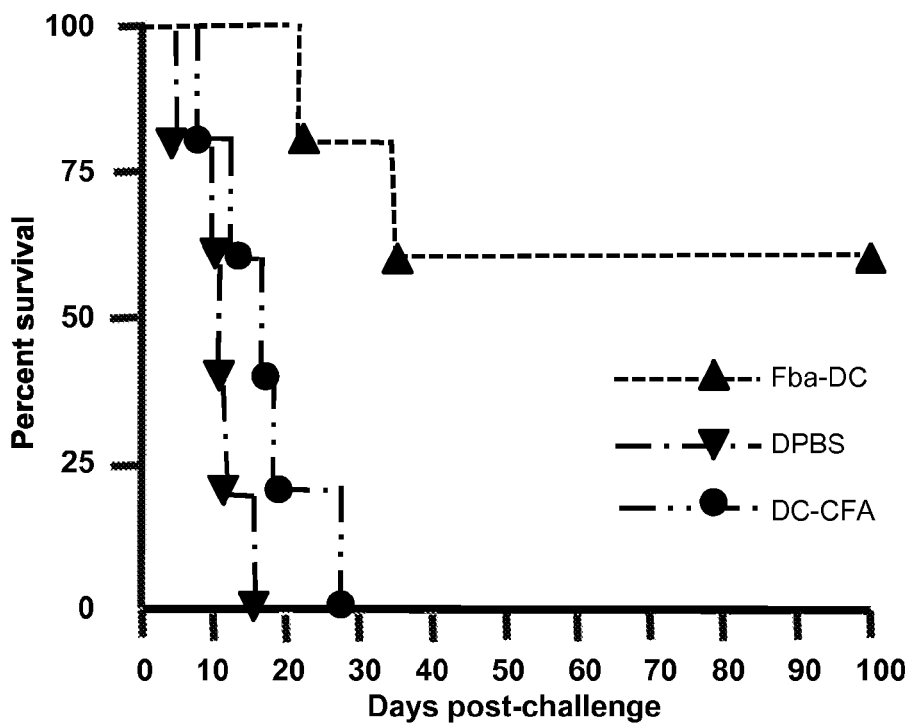
FIGS. 3A and 3B show a survival curve (FIG. 3A) and CFUs per kidney (FIG. 3B) from BALB/c mice vaccinated with Fba peptide vaccines by the dendritic cell approach and then challenged with a lethal dose of a prototypical strain of C. albicans (SC5314).
Figure 3B:
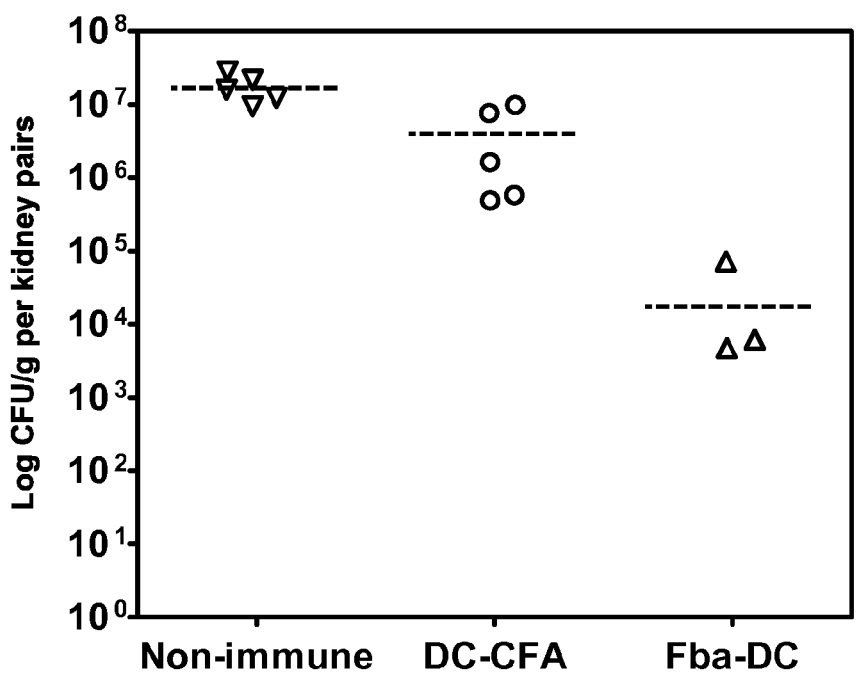
Figure 3C:
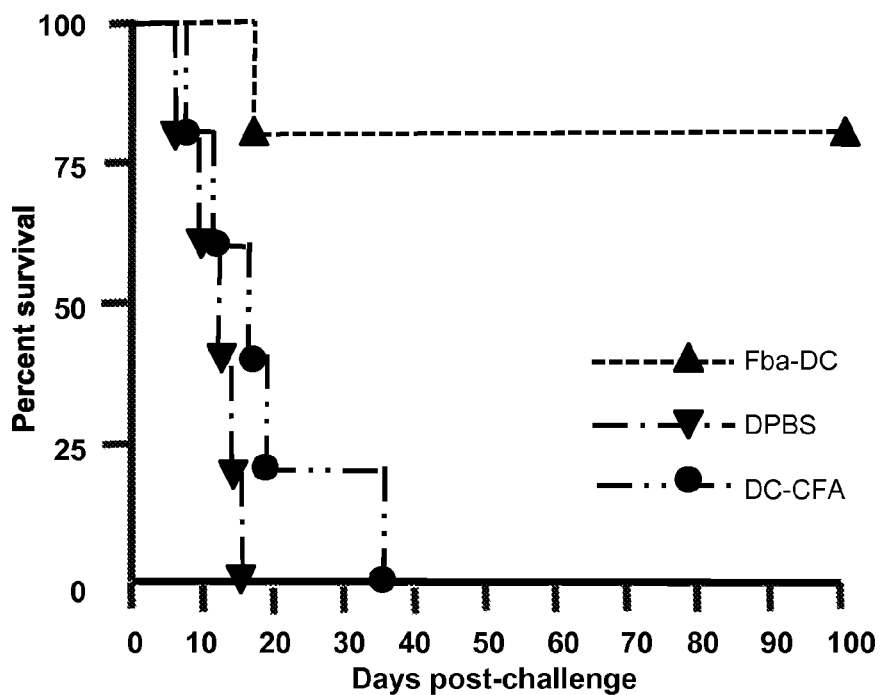
FIGS. 3C-3D show a survival curve (FIG. 3C) and CFUs per kidney (FIG. 3D) from mice vaccinated with Fba peptide vaccines by the dendritic cell approach and then challenged with a lethal dose of a prototypical strain of C. albicans strain 3153A.
Figure 3D:
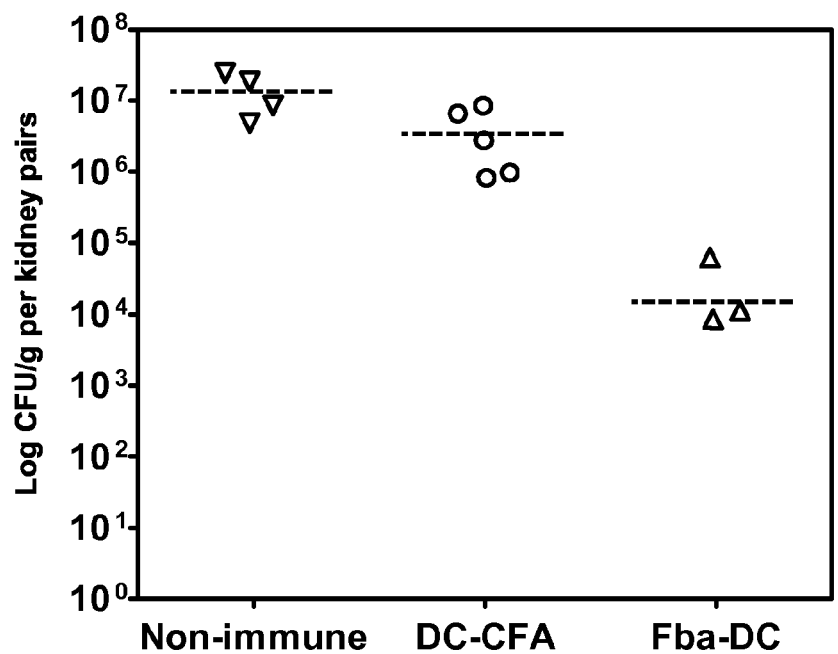

FIGS. 3A-3D show that Fba peptide vaccines induced protective responses in BALB/c mice against disseminated candidiasis caused by different *C. albicans* strains. Vaccination with Fba peptide by the dendritic cell approach induced significant protection against experimental disseminated candidiasis in mice, regardless of the fungal strain, as compared to control groups. In FIG. 3A, vaccinated mice challenged with a lethal dose of a prototypical strain of *C. albicans* (SC5314) had a significant prolonged survival time as compared to control mice that received DCs+CFA or DPBS (P<0.01). Consistent with survival data, immunized mice had greatly reduced or non-detectable CFUs in their kidneys (P<0.01) as compared to control mice (FIG. 3B). Similar results were obtained when immunized mice were challenged with *C. albicans* strain 3153A (FIG. 3C, survival curve; and FIG. 3D, CFUs from kidneys).

Example 5

Vaccine Efficacy in BALB/c and C57BL/6 Mice: Antibody Titers and Survival Studies As indicated above (FIG. 2), the Fba peptide also induced strong antibody responses in C57BL/6 mice. C57BL/6 mice are more prone to Th1 responses and supposedly more resistant to disseminated candidiasis than are BALB/c mice that are more prone to Th2 and, hence, antibody responses. Thus, in an effort to determine the general efficacy of the Fba vaccine, whether immunized C57BL/6 mice are protected against disseminated candidiasis was tested. The results are shown in FIGS. 4A-4C.

Figure 4A:
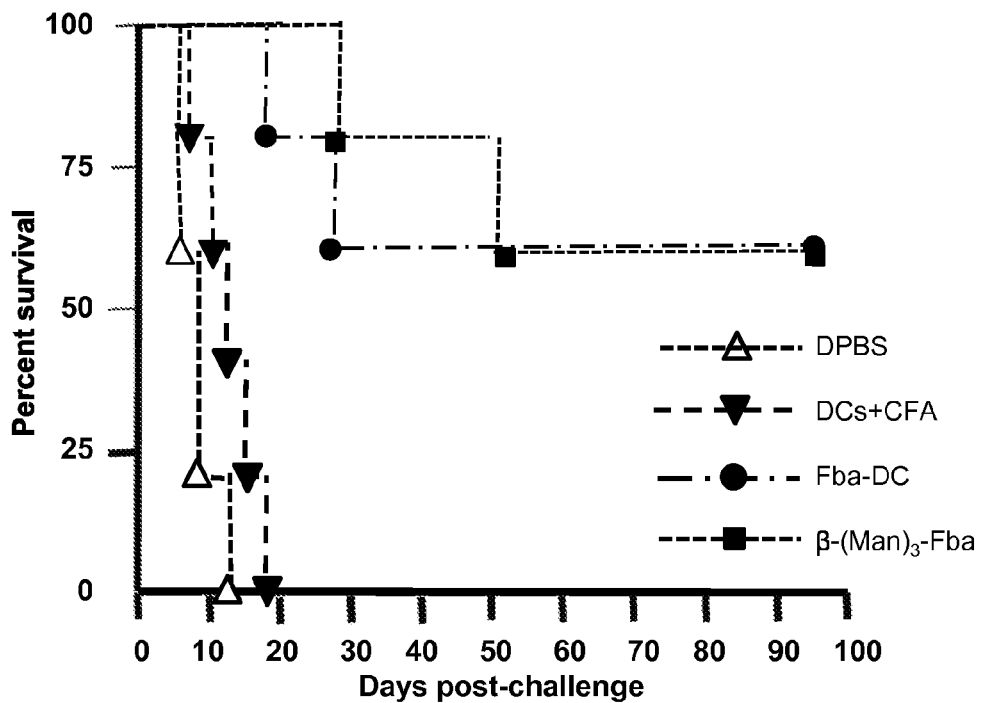
FIGS. 4A-4C show protective responses in C57BL/6 mice against experimental disseminated candidiasis in mice immunized against either the Fba peptide-DC vaccine or β-(Man)$_3$-Fba-pulsed DCs as compared to DPBS and DCs+CFA control mice and then challenged with a lethal dose of a prototypical strain of C. albicans strain 3153A.
Figure 4B:
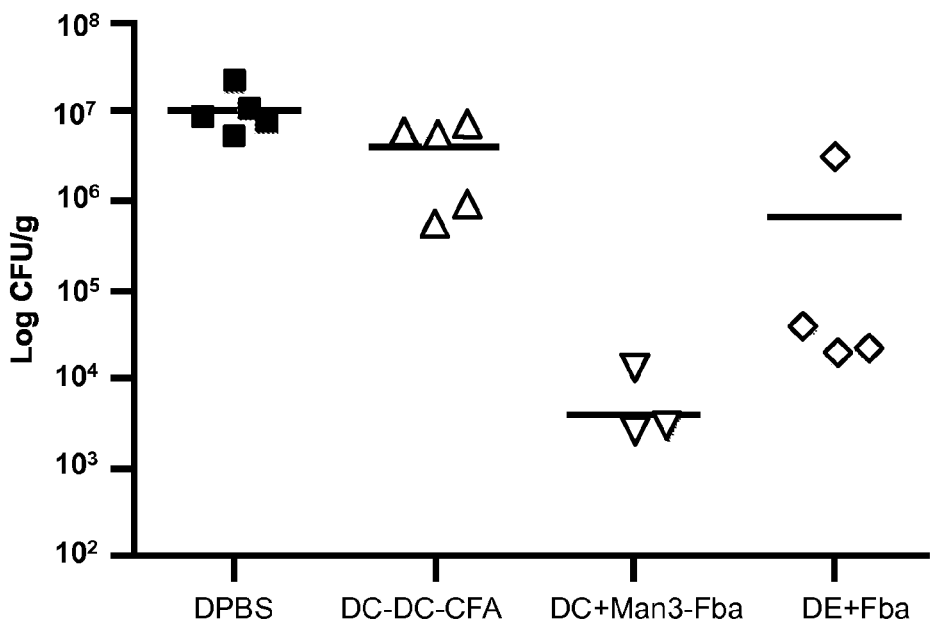
Figure 4C:
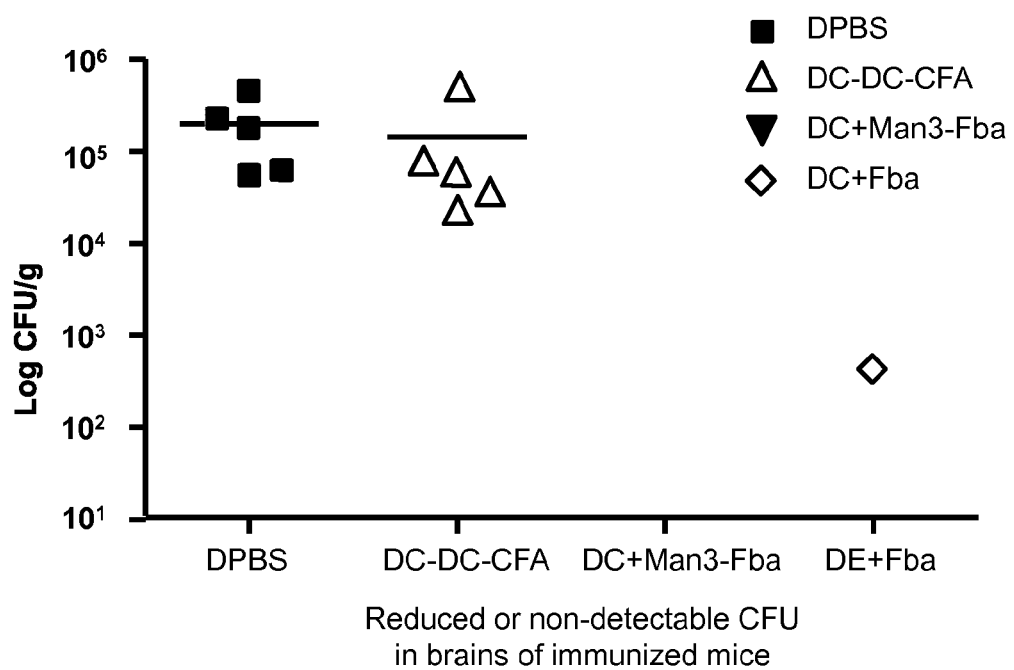

FIGS. 4A-4C show protective responses in C57BL/6 mice against experimental disseminated candidiasis when Mice immunized against either the Fba peptide-DC vaccine or β-(Man)$_3$-Fba-pulsed DCs. FIG. 4A indicates the peptide immunized mice survived significantly longer (P<0.01) than DPBS and DCs+CFA control mice. FIGS. 4B and 4C show that the immunized mice that survived the experiment were found to have greatly reduced or non-detectable live CFUs above 50 CFUs/g in their kidneys (P<0.01) (FIG. 4B) and brains (P<0.001) (FIG. 4C) as compared to controls. The bar of each panel in FIGS. 4B and 4C indicates mean of CFUs for each group. Each value of CFU represents each individual mouse. There are no data points for β-(Man)$_3$-Fba-pulsed DCs (the 3rd column) because the CFU numbers of these vaccinated mice were less than 50 CFUs/g. For Fba-DC, there was a single mouse with a brain CFU above 50 CFU/g, and thus a single datum point is shown; the remaining four mice had less than 50 CFU/g tissue.

Vaccination with Fba peptide-pulsed DCs induced protection against experimental disseminated candidiasis in this mouse strain (FIG. 4A) as was observed for the BALB/c mouse (53). Specifically, Fba peptide vaccination resulted in a prolongation of survival of both BALB/c (53) and C57BL/6 mice compared to that of DPBS controls or adjuvant only vaccination. Consistent with survival data, immune mice that survived the observation period had greatly reduced or non-detectable live fungal units CFUs in their kidneys and brains as compared to controls that were sacrificed when they became moribund following i.v. challenge with the fungus (FIGS. 4B and 4C).

Example 6

Anti-Fba Peptide Immune Sera Provide Passive Protection for Naïve Mice

To answer whether induced anti-Fba antibody responses are responsible, at least in part, for the protection, antisera were collected from immunized mice and transferred i.p. to naïve mice 4 h before i.v. challenge with a lethal dose of C. albicans. Control groups were given either immune sera absorbed with live C. albicans yeast cells or DPBS buffer prior to the challenge. Immune serum donors, which were immunized with Fba peptide pulsed DCs, were used as a positive control for protection.

Figure 5A:
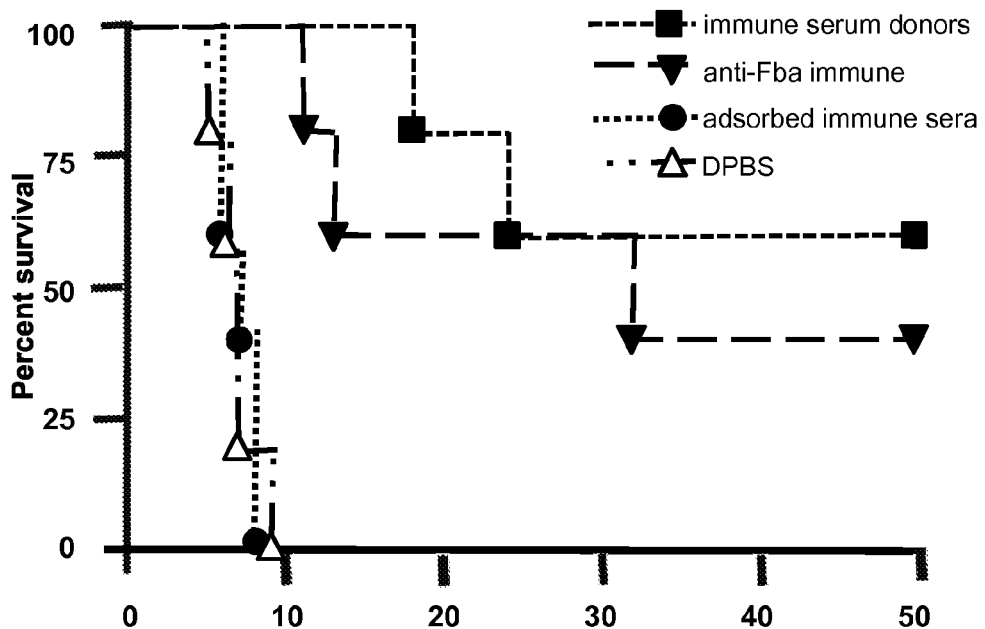
FIGS. 5A and 5B show the percent survival and the CFUs in kidneys, respectively, of mice who received serum from other mice immunized by the dendritic cell approach against Fba peptide 14 days post-immunization, as compared to the initial mice serum donors, mice receiving serum after absorption with C. albicans, and mice receiving control DPBS.
Figure 5B:
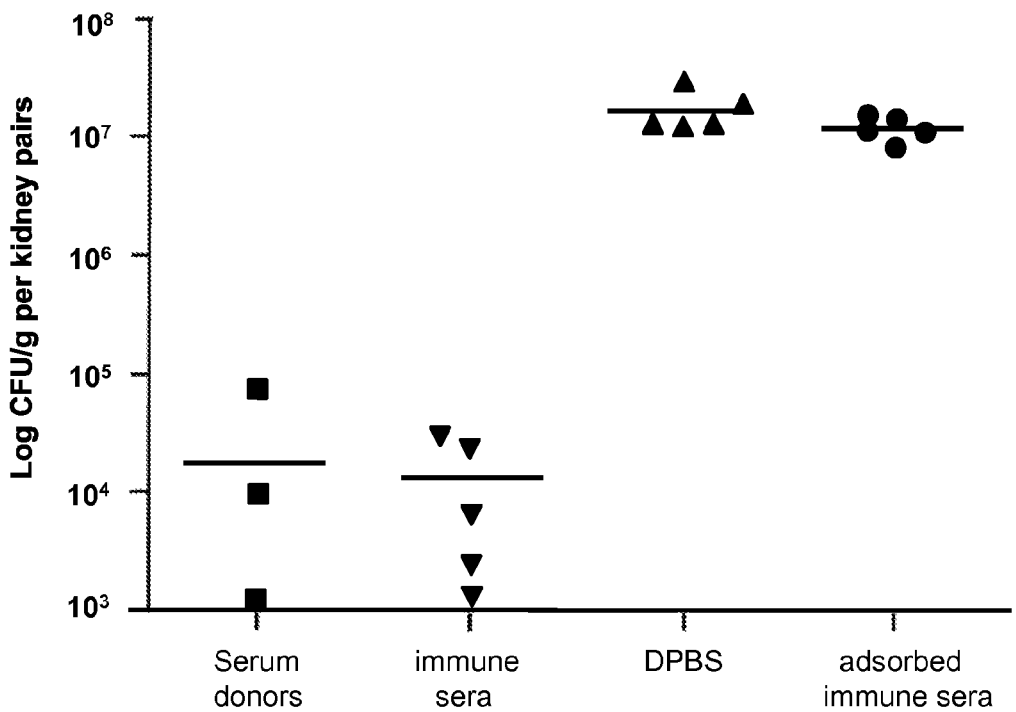
Figure 5C:
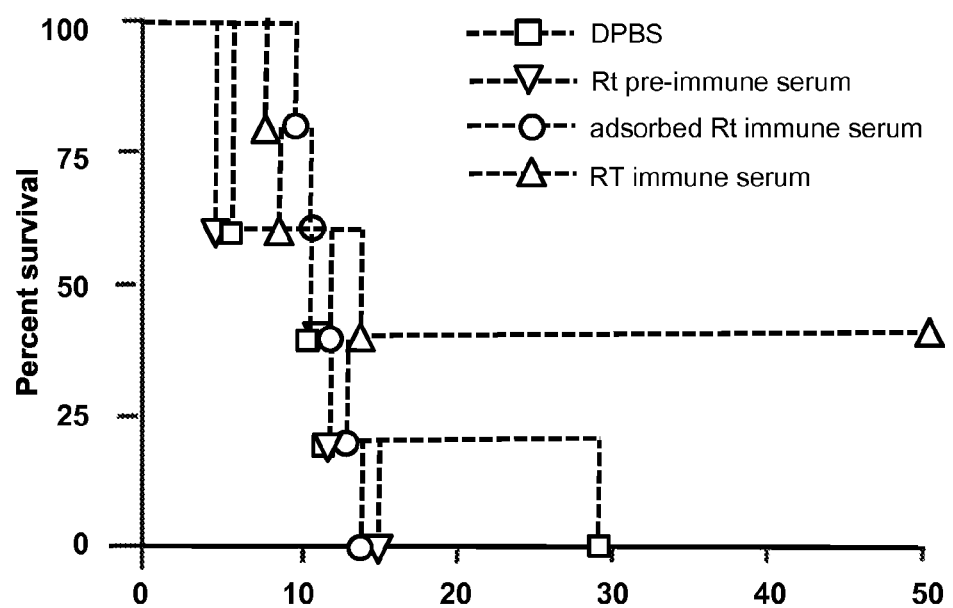
FIG. 5C shows the percent survival of mice who received rabbit immune sera containing specific anti-Fba polyclonal antibodies (PAbs), as compared to control mice (DPBS), mice who received the rabbit immune sera after absorption with C. albicans, and mice who received rabbit sera taken prior to antibody production.

As shown in FIGS. 5A-5C, sera from immunized mice was responsible for protection against disseminated candidiasis. Serum was collected from mice immunized by the dendritic cell approach against Fba peptide 14 days post-immunization. Immune sera were pooled and tested for passive protection of naive mice against experimental disseminated candidiasis as described in Example 1 above. FIG. 5A shows survival curves and indicates that enhanced protection against disseminated C. albicans infection was observed in mice that received serum from mice immunized with the Fba peptide as compared to animals that received control materials. Note that the donor mice used as positive controls for protection had similar survival curve as the naïve mice that received the immune serum. Importantly, absorption with C. albicans before transfer also removed the protective value of immune serum. FIG. 5B indicates that the immunized mice and mice that received antiserum had significantly fewer (P<0.0001) fungal counts or non-detectable CFUs in kidneys as compared to the control groups that received DPBS buffer or the same sera that had been preadsorbed with C. albicans yeast cells. FIG. 5C shows that rabbit immune sera containing specific anti-Fba polyclonal antibodies (PAbs) also provided some protection to mice against disseminated candidiasis. The rabbit immune sera treated group had prolonged survival time as compared to the control groups that received adsorbed rabbit sera, or rabbit pre-immune serum or DPBS buffer.

After challenge, immunized mice and mice treated with the antiserum had prolonged survival times as compared to the two control groups (FIG. 5A), and consistently, mice that received the antiserum had significantly reduced fungal counts in their kidneys (FIG. 5B). The data provide strong support that anti-Fba peptide antibodies are at least partially, if not entirely, responsible for the protection against a lethal challenge with the fungus.

For the commercial rabbit anti-Fba sera, both the anti-Fba immune serum and pre-immune serum were absorbed by mouse splenocytes to remove possible rabbit natural anti-mouse cytotoxic antibodies. As a negative control, after the splenocyte absorption, rabbit anti-Fba immune serum was absorbed again, but this time with live C. albicans yeast cells to remove Fba-specific antibodies. Anti-Fba antibody titers were tested by ELISA before and after adsorption with the fungal cells. The Fba antibodies were no longer detectable following the adsorption (data not shown). The mice treated with rabbit antiserum had 40% survival at the end of the experiment and overall prolonged survival times as compared to the control groups (FIG. 5C), which again supports a protective role for anti-Fba antibodies against candidiasis. The reason for the relatively weak protection by rabbit immune sera, as compared to mouse anti-Fba sera, is not known but may well be due to lower efficiency of FcR effector function of rabbit antibodies within the mouse system (1).

Example 7

Fba Peptide Administered Along with Alum Induces Modest Protection Against Candidiasis To make a vaccine more appropriate for human use, Fba peptide was administered as a mixture with one of two adjuvants: alum (aluminum hydroxide gel, Sigma) or MPL (Lipid A, monophosphoryl, Sigma). Mice were immunized by sub-cutaneous (s.c.) injection of 0.2 ml containing 2.5 μg of Fba peptide mixed with either 50 μg alum or 10 μg MPL on days 1, 21 and 42. Negative control groups of mice were given a similar volume of DPBS buffer or adjuvant only. Serum samples were collected 14 days after immunization, diluted 1:100 and tested by ELISA on plates coated with synthetic Fba-MAP peptide. The results are shown in FIGS. 6A-6C.

Figure 6A:
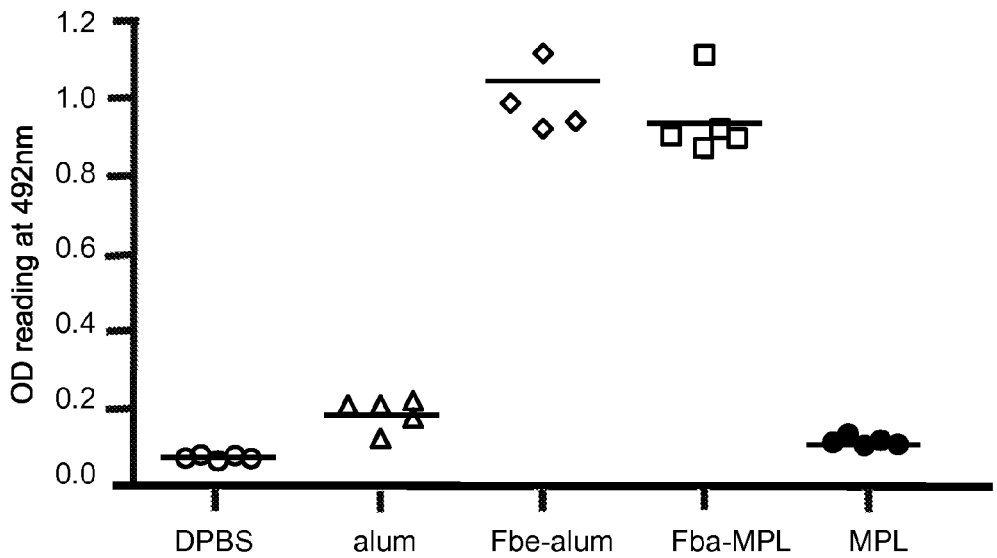
FIGS. 6A-6C show responses in mice immunized using Fba peptide vaccines administered along with human approved adjuvants (both Fba-alum and Fba-MPL) as compared to adjuvant only or control.
Figure 6B:
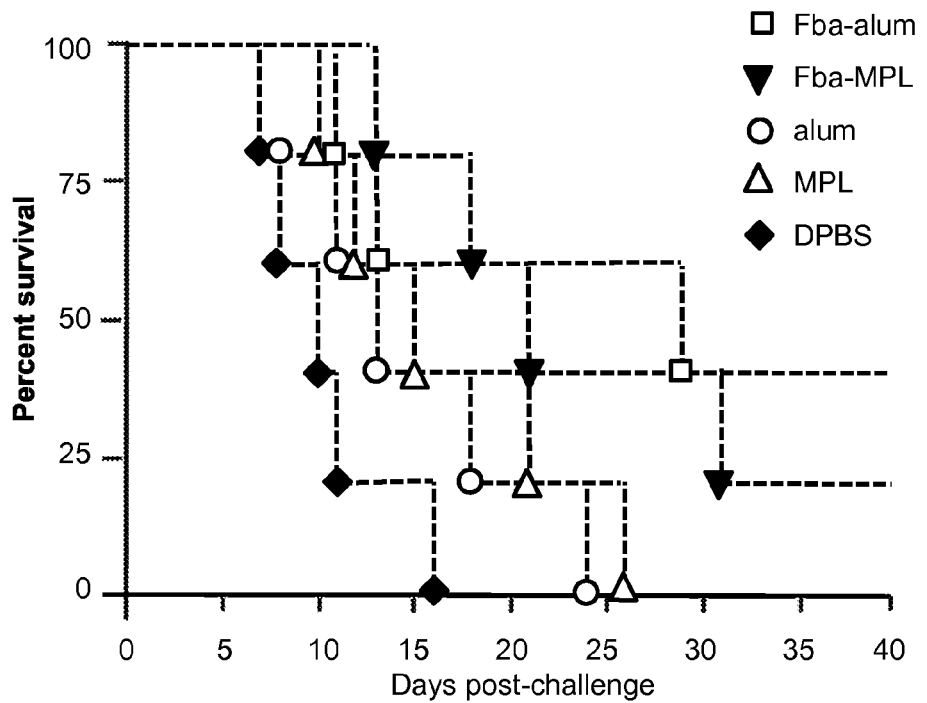
Figure 6C:
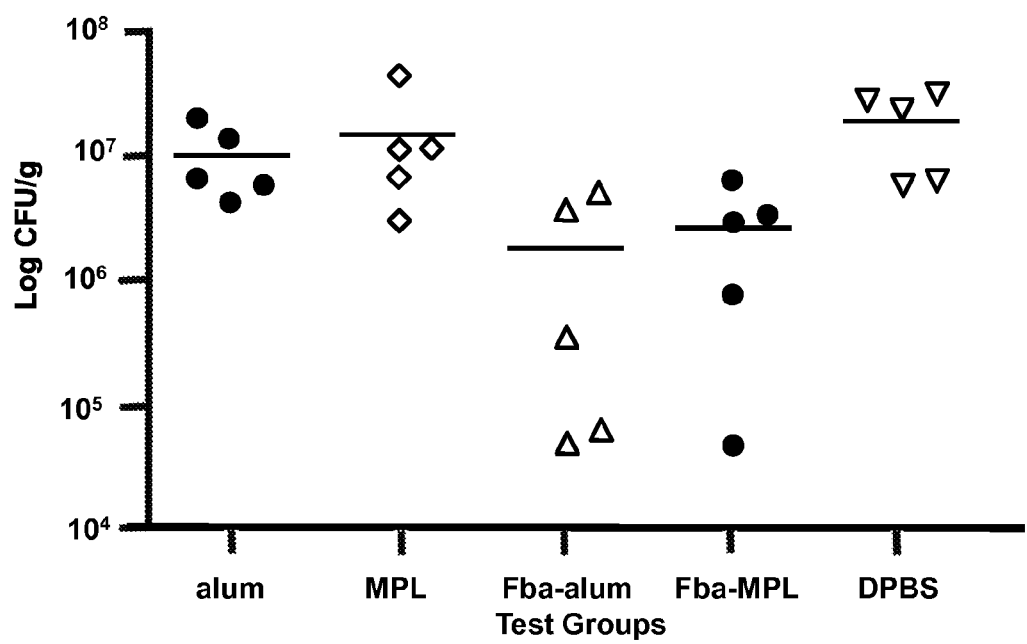

FIGS. 6A-6C show responses in mice from immunization with Fba peptide vaccines administered along with the human approved adjuvant alum against disseminated candidiasis. FIG. 6A show the amount of Fba antibody as tested by ELISA using serum samples collected 14 days after immunization, diluted 1:100 and tested by ELISA on plates coated with synthetic Fba-MAP. After the first booster, immune serum from mice immunized with Fba peptide prepared in either alum or MPL showed that antibody responses to the Fba peptide were more than 5-8 fold greater than that of sera from groups that received DPBS or adjuvant only. FIG. 6B shows the percent survival of the mice and indicated that moderate protective immunity was induced by Fba peptide when alum was used as the adjuvant, and slight protection was observed when MPL was used as the adjuvant as compared to DPBS or adjuvant unimmunized controls. The survival was also slightly extended in mice that received only alum or MPL as compared to DPBS but the differences were not statistically significant. FIG. 6C indicates that the immunized mice with either Fba-alum or Fba-MPL had significantly reduced viable fungal units (CFUs) per kidney pairs compared to DPBS control group or adjuvant only groups (P<0.01).

After the first booster, immune sera from mice immunized with Fba peptide prepared in either alum or MPL showed that antibody responses to either preparation were more than 5-8 fold greater over background sera obtained from mice that received DPBS or adjuvant only (FIG. 6A). Following the second booster immunization, an isotype switch from IgM to IgG of Fba specific antibodies was observed in the sera from immunized mice (data not shown), which suggested induction of an immune memory response. In addition, the vaccinated groups had prolonged survival times as compared to two control groups after challenge with a lethal dose of C. albicans cells (FIG. 6B); although the protection was not as strong as that which was induced by the DCs+CFA approach. Mice immunized with Fba peptide administered along with alum had 40% survival; however, Fba with MPL only induced slight protection as compared to control groups. Along with prolonged survival times, immunized mice had reduced live fungal cells in their kidneys as expected (FIG. 6C).

Example 8

Fba Monoclonal Antibody (MAb) Binds to the Fungal Cell Surface

MAbs specific for Fba peptide were obtained by use of standard hybridoma techniques. After cell fusion, specific antibody producing hybridomas were cloned four times by limiting dilution, of which 48 anti-Fba IgM clones and 12 anti-Fba IgG clones were selected. Clones that produced monoclonal antibodies (MAbs) E2-9, B7-18 and B7-22, isotyped as immunoglobulin M (IgM), were selected and expanded in BD serum-free culture medium.

Figure 7A:
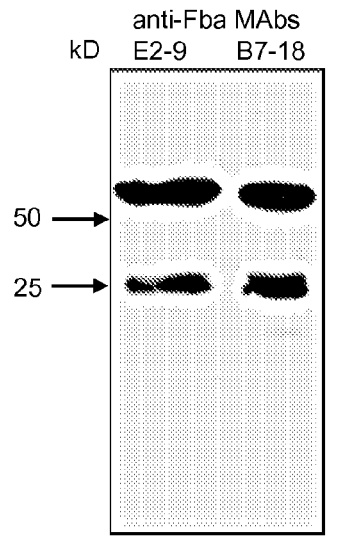
FIG. 7A-7B indicates the molecular size of MAbs E2-9 and B7-18 as compared to IgM.
Figure 7B:
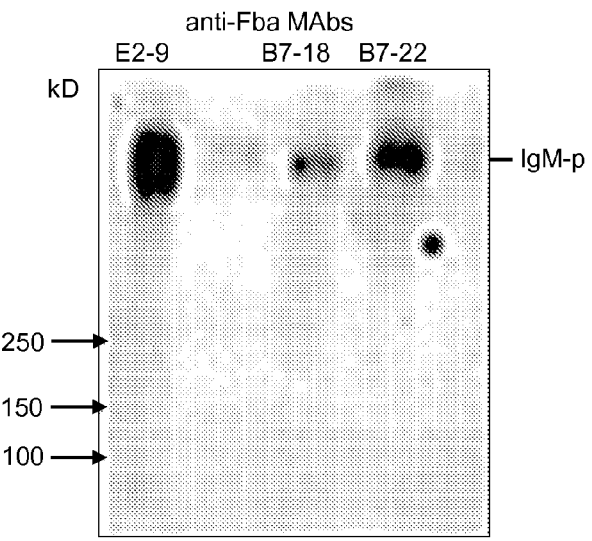
Figure 7C:
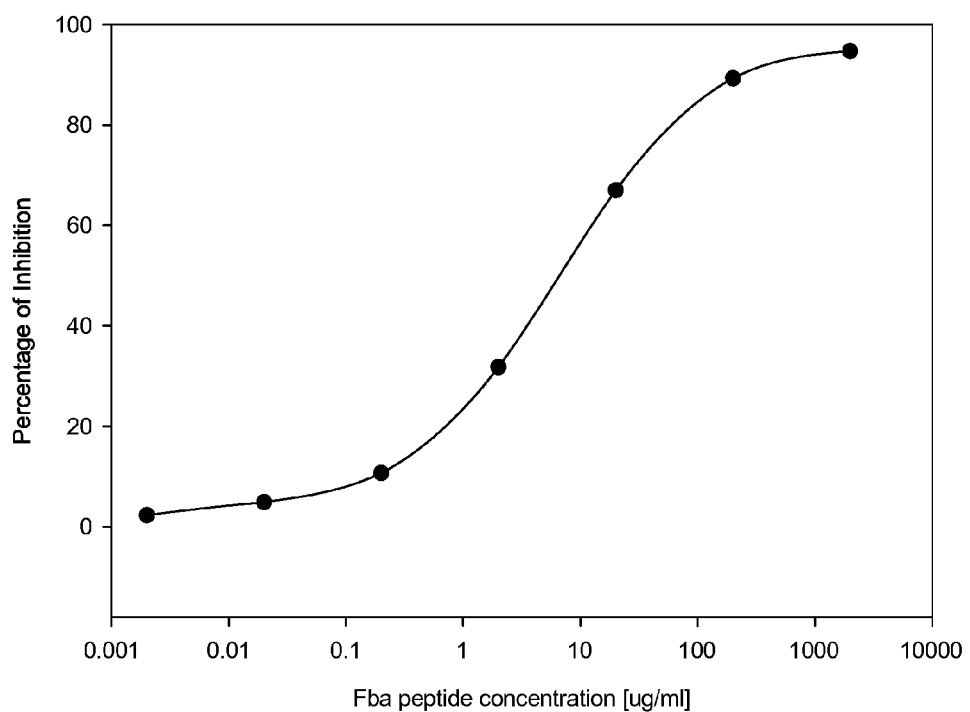
FIG. 7C shows ELISA inhibition data for the anti-Fba peptide MAb E2-9, using synthetic Fba peptide as an inhibitor to determine the reaction and binding affinity of MAb E2-9 with Fba peptide. Each point is the mean of three determinations, and the data shown are from a typical experiment of four independent experiments.

FIGS. 7A-7C show that MAbs were detected by SDS-PAGE and the specificity of Fba reaction with MAb E2-9 was determined by inhibition ELISA. In FIG. 7A, clones producing IgM MAbs (E2-9, B7-18 and B7-22) were selected and expanded in BD serum-free culture. Heavy and light chains of E2-9 and B7-18 with corresponding sizes were shown on 12.5% SDS page gel under reducing condition. FIG. 7B confirms that the isotype of E2-9, B7-18 and B7-22 is IgM as indicated by SDS-PAGE indicating a whole molecular size consistent with IgM molecule. FIG. 7B shows the putative IgM pentamer as observed by western blots of 10% SDS-PAGE gel run under non-reducing conditions and the molecular mass of the purified anti-Fba IgM MAb (E2-9) was estimated at 900 kD. FIG. 7C shows the ELISA inhibition data for the anti-Fba peptide MAb E2-9. Synthetic Fba peptide was used as an inhibitor to determine the reaction and binding affinity of MAb E2-9 with Fba peptide. Each point is the mean of three determinations, and the data shown are from a typical experiment of four independent experiments, all producing similar results. The concentration of inhibitor (Fba peptide) required to achieve 50% inhibitory concentration was about 10 µg/ml. Under reducing conditions and polypeptide chain confirmation by western blots developed with goat anti-mouse IgGAM (H+L)-HRP antibody, heavy and light chains of E2-9 and B7-18 showed the correct corresponding sizes of 50 KDa and 25 KDa, respectively (FIG. 7A). The IgM pentamers (~900 KDa) of MAbs were detected by western blot analysis developed with goat anti-mouse IgGMA HRP antibody from non-reducing SDS gels (FIG. 7B). Clone E2-9 grew well and proliferated faster as compared to Clones B7-18 and B7-22, and was a consistently high producer of high titer anti-Fba antibodies. Therefore E2-9 was used for further study. The reaction of E2-9 for the Fba peptide was determined by an ELISA inhibition assay (FIG. 7C), in which soluble synthetic peptide Fba effectively inhibited the reactivity of MAb E2-9 with solid phase Fba.

MAb E2-9 was also detected by an indirect immunofluorescence antibody test to confirm its specific reactivity with Fba peptide on the cell surface of C. albicans. FIG. 8A indicates Fba peptide in both fresh and formaldehyde-fixed C. albicans yeast cells and hyphae as detected using MAb E2-9 in confocal microscopic analyses. As shown in FIG. 8A, the peptide Fba was expressed on the fungal surface and E2-9 was bound to both yeast and hyphal forms of the fungus. MAb B6.1, which is specific to β-(Man)$_3$, was used as a positive control. In FIG. 8B, MAb E2-9 binding to the Fba peptide expressed on the C. albicans cell surface was further confirmed by use of flow cytometric analysis. Compared to MAb B6.1, which is specific for the C. albicans cell surface epitope β-trimannose, the reactivity of MAb E2-9 with live C. albicans cells was relatively slight. In FIG. 8C, an important additional negative control tested whether the binding of MAbs E2-9 and B6.1 occurs on live Saccharomyces cerevisiae, which should not express either Fba or the β-trimannose epitope. Neither MAb bound to the cell surface of S. cerevisiae.

MAb B6.1, which binds to an abundantly expressed cell surface epitope, β-1,2-mannotriose and protects mice against disseminated candidiasis (25, 28), was used as a positive control for an IgM antibody binding to the fungal cell surface. No cross-reactivity was detected when MAb E2-9 was tested against other Candida species (data not shown), which was expected because the Fba 14 mer amino acid peptide should be unique to C. albicans as previously reported (53). Reactivity of MAb E2-9 with the cell surface of C. albicans was also demonstrated by flow cytometric analysis (FIG. 8B). MAb B6.1 was also used as a positive control for antibody binding to C. albicans yeast cell surface. Although MAb E2-9 reacted with wild type C. albicans 3153A, as expected the antibody did not label isolates of other Candida species (C. glabrata & C. krusei, data not shown) or S. cerevesiae (FIG. 8C).

Example 9

IgM MAb (E2-9) Conferred Enhanced Protection Against Systemic Candidiasis in Passive Transfer Experiments In the examples above, the protective potential of anti-Fba antibodies induced by either the Fba-DCs vaccine approach or by immunization with the peptide suspended in alum adjuvant was shown. Development of monoclonal antibodies specific for Fba peptide provides the possibility of producing an unlimited supply of protective antibody for in vivo applications. MAb E2-9 was selected for study and was tested as described above in passive transfer experiments showing protection by polyclonal antiserum. The results are shown in FIGS. 9A-9B.

FIGS. 9A and 9B indicated that anti-Fba IgM MAb (E2-9) protected mice against disseminated candidiasis. To confirm that MAb E2-9 produced by cell culture was able to protect mice against experimental disseminated candidiasis, MAb E2-9 (16 µg/ml, 0.5 ml) was given to naïve mice 4 h before i.v. C. albicans challenge, another 0.2 ml of MAb E2-9 was given 24 h after the first dose. Mice that were immunized with the β-(Man)$_3$-Fba conjugate were used as a positive control for survival and DPBS and MAb E2-9 absorbed by C. albicans yeast cells was given to naïve mice as a negative control. As shown in FIG. 9A, the mice that received MAb E2-9 had a prolonged survival time that was similar to the positive control group that was actively immunized with the β-(Man)$_3$-Fba as compared to the DPBS or absorbed MAb E-9 negative control group (P<0.001). In addition, passive transfer of MAb E2-9 to naïve mice reduced the kidney fungal burden to a level similar to survivors that were actively immunized as compared to the fungal burden in mice that were given DPBS or absorbed MAb E2-9 (P<0.001) (FIG. 9B). Thus the mice given an i.p dose of MAb E2-9 had prolonged survival as compared to control animals, and reduced fungal burden in their kidneys. Importantly, passive protection was prevented by removal of the MAbs by absorption with Candida cells before transfer, which provided strong additional evidence for the protection being due to the MAb E2-9.

Thus to summarize the above examples, all six derived peptides (SEQ ID NOS:1-6) induced antibody responses when used alone to pulse DCs for subsequent immunizations, and three peptides Fba (SEQ ID NO:1), Hwp1 (SEQ ID NO:3), and Met6 (SEQ ID NO:2) induced a high degree of protection as evidenced by survival and low kidney fungal burden in mice challenged with the fungus. Vaccinated mice had obviously less fungal burden in kidneys as compared to non-surviving controls; in fact, CFU burden was not detectable in the kidneys of some of the vaccinated mice against the three peptides, whereas this never happened in control groups. Combination of prolonged survival with significantly reduction or clearance of kidney CFU provided strong evidences to show protection induced by vaccines. One particular peptide Fba, which induced robust antibody responses and best protection among three protective peptides, was further characterized as a novel vaccine candidate. The Fba peptide epitope alone is not MHC II restricted as it is immunogenic as demonstrated by specific antibody production in different strains of mice and rabbits. The hyper-immunized animals produced both IgM and IgG classes of antibodies, suggesting production of memory cells and possible long-term immunologic responsiveness.

We have also shown an effective vaccine composition that provides protection against disseminated candidiasis with a more acceptable formulation for human use, using alum as the adjuvant. Mice immunized with a combination of the Fba peptide and alum showed protection against disseminated candidiasis that was statistically significant in terms of lower kidney CFU's and increased survival as compared to non-immune controls. Antibody activity specific for the Fba peptide appears to be responsible at least in part for the anti-Candida protection, as was demonstrated by experiments involving passive transfer of whole immune serum, which conferred protection to naïve mice. Such protection was not conferred by control pre-bled normal mouse serum and the protection was abrogated when immune serum was pre-absorbed by fungal cells prior to the passive transfer protection test. The protective ability against disseminated candidiasis of MAb E2-9, which is specific for the Fba epitope, was also demonstrated in vivo. We also showed that the Fba peptide epitope is expressed on the fungal cell surface and is accessible by antibodies, thus blockage of adhesion is a reasonable mechanism to investigate.

Fba1p is a key enzyme required for growth on both fermentative and nonfermentative carbon sources, and this enzyme is essential for viability of C. albicans and other Candida spp. (48). However, Fba1p must be depleted to below 5% of wild-type levels before growth is blocked (48). Fba1p depletion appears to exert static rather than cidal effects upon C. albicans. Therefore, even though the role of Fba1p on the cell surface is unknown, it is possible that antibodies against Fba1p may prevent the growth of C. albicans infecting a patient. Thus, peptide specific MAb E2-9 may have the potential for use as an immunotherapy against disseminated candidiasis either alone or combined with other antifungal drugs. A possible limitation to the use of vaccines in immunosuppressed patients is that these patients may not necessarily mount protective responses, but passive immunization with protective antibodies may be a rapid and effective preventive or even therapeutic measure. The efficacy of this immunoprophylaxis can be augmented when used in combination with conventional antifungal therapy, as it has been shown with Mycograb and amphotericin B (Amp B) in patients with invasive candidiasis (44). MAb B6.1 was also demonstrated to enhance therapeutic efficacy of Amp B, which may lead to a reduction of the amount of the antifungal agent needed for treatment to non-toxic levels (24). E2-9 was shown to bind to the hyphal cell surface, indicating that functional Fba epitope is accessible to antibodies on hyphal cell surfaces; our recent data, however, have shown neither the immune serum nor MAb E2-9 exert a marked inhibition of Candida yeast or hyphal growth in vitro (Data not shown). We believe that a combination of MAb B6-1 and E2-9 could synergistically induce protective immunity in mice. MAb B6.1 antibody had protective activity when given before infection and slight therapeutic activity when given after infection (25). MAb B6.1 is specific to a β-1,2-linked mannotriose, which is an acid-labile component of the phosphomannan complex of C. albicans. This epitope appears to be a major surface marker, as indicated by confluent distribution patterns revealed by immunofluorescence. The preventive or prophylactic activity of MAb E2-9 against disseminated candidiasis was not compared to that of MAb B6.1. Based on median survival times, both antibodies showed similar protective activities. We believe, that due to the possible different mechanism for protection by those two different MAbs, they will exert a synergistic effect to fulfill solid protection by working together.

Example 10

Development and Testing of More General Fungal Vaccines

Peptide Design.

As described above, six cell wall proteins were selected as possible carriers on the basis of their known expression during pathogenesis of human candidiasis a cell wall location, and included: hyphal wall protein-1 (Hwp-1); enolase (Enol); phosphoglycerate kinase (Pgk1); glyceraldehyde-3-phosphate dehydrogenase (Gap-1); fructose-bisphosphate aldolase (Fba); and methyltetrahydropteroyltriglutamate (Met6). By application of an epitope-finding algorithm (http://www-.genscript.com/cgibin/tools/antigenic_prediction.pl), the following 14-mer peptides were selected for synthesis, all of which are located near the N-terminus of each protein group: Hwp1, QGETEEALIQKRSY (SEQ ID NO:3); Enol, DSRGNPTVEVDFTT (SEQ ID NO:4); Pgk1, VPLDGK-TITNNQRI (SEQ ID NO:6); Gap1, NRSPSTGEQKSSGI (SEQ ID NO:5); Fba, YGKDVKDLFDYAQE (SEQ ID NO:1); and, Met6, PRIGGQRELKKITE (SEQ ID NO:2). Synthetic peptides were produced commercially (GenScript) or synthesized by use of an automated peptide synthesizer, conjugated to the (3-mannan trisaccharide epitope, and the efficacy of vaccines based on these conjugates were reported (53).

New peptides have been designed to make the vaccine effective against broader fungal species, including C. albicans, C. glabrata, Aspergillus fumigatus, A. niger, A. nidulans, Pichia stipitis, P. guilliermondii, and S. cerevisiae. Looking for a possible universal epitope, additional searching in the N-terminus region of Fba protein was performed. A peptide of 14 amino acids based on Fba was identified that was expressed in multiple fungal species. One of these peptides was named "Fba2", FAIPAINVTSSSTV (SEQ ID NO:7), and was found to be expressed by multiple fungal species.

As shown below, initial work with Fba2 was somewhat disappointing in providing protection. So to make a better epitope, a flanking sequence was added to Fba2 to make Fba3, a 19 amino acid peptide which includes 5 additional amino acids at the end of Fba2. The sequence for Fba3 is FAIPAIN-VTSSSTVVAALE (SEQ ID NO:8). In addition, Fba4, a shorter 9 amino acid peptide, was made. The sequence of Fba4 is SSSTVVAAL (SEQ ID NO:9). In addition, a new peptide based on Met6 was designed, named Met6-2, based on the expression in many fungal species. The sequence of Met6-2 is YDQVLDLSLLFNAIP (SEQ ID NO:10). These four new peptides, Fba2, Fba3, Fba4, and Met6-2, were tested for effectiveness as vaccines by methods described above in Example 1.

Efficacy of Fba2, Fba3, Fba4 and Met-6-2 as Vaccines:

The above peptides were tested for their ability to induce antibodies in BALB/c mice and to provide protection against disseminated candidiasis by methods described in Example 1. DCs were generated from bone marrow as described above with some modifications. Briefly, bone marrow flushed with RPMI-1640 from the long bones of euthanized mice was gently pipetted and filtered through a 70-mm cell strainer to dissociate cell clusters. Red blood cells were lysed (ACK lysing buffer, 0.15 M $NH_4Cl$, 1.0 mM $KHCO_3$, 0.1 mM EDTA) and remaining bone marrow cells were suspended in complete medium ["CM", RPMI-1640 supplemented with 10% fetal bovine serum (FBS), 2 mM L-glutamine, 1% of nonessential amino acids and 100 U/ml penicillin and 100 mg/ml streptomycin], adjusted to $2 \times 10^5$ cells/ml, plated in 6-well plates at 5 ml/well, and cultured for up to 9 days in the presence of 40 ng/ml of rmGM-CSF and rmIL-4 (R&D Systems) at 37° C., 5% $CO_2$. On days 4 and 7 of culture, the same amount of fresh GM-CSF and IL-4 was added to the wells.

To isolate the DC population, the cells were suspended in 2-4 ml of warm CM, overlaid onto the same volume of 14.5% (w/v) Nycodenz (Sigma) in CM and centrifuged at 1200×g for 20 min at 22° C. After centrifugation, cells in the interface were collected, washed with CM three times and subjected to phenotypic and functional analyses. Flow cytometric analysis and the use of MAbs specific for CD11c, CD11b, CD19 and CD3e (eBioscience) showed that over 80% of the cells were DCs.

Immunogens and Immunizations.

DCs were pulsed in vitro with vaccines as described above. Briefly, DCs in culture were pulsed with the antigen of choice (1 μM) on day 6. On day 7, $PGE_2$ ($10^{-7}$-$10^{-9}$M) was added along with LPS (2 μg/ml, Sigma) for 24 h. On day 9, antigen-pulsed DCs were washed extensively, and $5 \times 10^5$ in 200 μl DPBS were given intraperitoneally (i.p.). The mice were boosted at day 14 with fresh antigen-pulsed DCs and boosted a second time at day 28 with antigen (10 μg) emulsified in complete Freund adjuvant (CFA).

Serological Assays for Anti-General Peptide Antibody Titers in Immune Sera from Immunized Mice:

Sera were ELISA analyzed for antibody titers. Control groups consisted of mice given DCs alone at the time of priming and first booster followed by DPBS at the time of the second booster, DPBS for the priming and first booster and CFA alone at the time of the second booster, DPBS alone for all three injections, or DCs alone for priming and first booster followed by CFA alone at the time of the second booster. Briefly, synthetic peptides were dissolved at 10 μg/ml in PBS (pH 7.4). Each was used to coat 96-well ELISA plates for testing duplicate serial 2-fold dilutions of samples of each immune serum and control sera. Color development for each well was achieved by secondary antibody (goat anti-mouse polyvalent immunoglobulin-HRP, Sigma) and substrate (O-phenylenediamine and $H_2O_2$) and Optical Density (OD) determined at 492 nm.

Fungal Challenge and Assessment of Protection.

Two weeks after the second boost, immune and control mice were infected i.v. with a lethal dose of live *C. albicans* yeast cells ($5 \times 10^5$ in 0.1 ml of DPBS). Passively immunized mice also received the same challenge dose. Protection was evaluated by monitoring animal survival for up to 120 days and by quantifying the number of CFU (mean±SE) per kidney pairs. Median survival times (MST) were statistically evaluated by Kaplan-Meier (GraphPad Prism, version 4). In all analyses, there were five mice per group (n=5), and a two-tailed t test was used.

Fba2 as Vaccine:

Fba2 was used to pulse DC in vitro as described above, and Fba-DC was used as positive control. Serum samples were tested after each injection. As a positive control, anti-Fba responses were also tested. As shown in FIG. 10A, Fba2 was able to induce good and specific antibody responses in BALB/c mice. As a positive control, anti-Fba responses were also tested, with results shown in FIG. 10B.

However, when tested for ability to provide protection in mice, Fba2 peptide failed to induce good protection as shown in FIG. 11. The mice immunized with Fba2 had no significant difference in survival time as compared to the control group injected with DC+CFA only.

Other Synthetic Peptides.

The other general peptides were also tested for ability to induce antibody responses. As shown in FIG. 12, Fba3, Fba4, and Met6-2 were able to induce antibody responses in BALB/c mice as tested by ELISA. But compared to anti-Fba responses, antibody responses to these three peptides were not as impressive. However, this lower result may reflect that the test for anti-Fba responses by ELISA used microtiter plates coated with Fba peptide that was conjugated to a multiple antigenic peptide (MAP), of which the lysine core bears eight copies of the Fba peptide epitope. There may be lower sensitivity for antibody detection when peptides alone are used for coating the plates, as was done with the general peptides.

To specifically test the binding of antibody in the immune serum to the general peptides expressed on *C. albicans* cell surface, the method of flow cytometric analysis was used. Live fungal cells were reacted with immune serum, and then with gost anti-mouse FITC conjugated 2nd antibodies. The negative control consisted of cells reacted with normal mouse serum. The positive control was the monoclonal antibody, MAb B6.1, which is specific for a cell surface epitope, β-mannotriose, which is abundantly and uniformly expressed. These data indicate that the peptides Fba, Fba3, Fba4, and Met6-2 are expressed on the fungal surface and are accessible to antibodies in immune sera. Thus antibodies to Fba3, Fba4, Fba, and Met6-2 can bind directly to the fungal cell surface peptides.

The ability of the general peptides to induce protection against disseminated candidiasis in mice was also tested as described above. The mice immunized with Fba3 and Met6-2 showed impressive survival rates as compared to the control group injected with DC+CFA only (FIG. 14). The experiment was terminated at time point of 80 days post challenge. Fba3 and Met6-2 peptide induced a high degree of protection with a survival rate 80%, while Fba4 induced moderate protection with survival rate of 60%. All the general peptides, except Fba2, (i.e., Fba3, Fba4, and Met6-2) immunized animals had significantly prolonged survival times as compared to controls. The positive control was Fba-DC which induced the highest degree of protection against the disseminated candidiasis.

The immunized mice were sacrificed and the kidneys collected to measure fungal infection as described above. As shown in FIG. 15, the mice immunized with peptides had reduced viable fungal units (colony forming units, CFU) per kidney pairs compared to DPBS control group and DC+CFA control group (P<0.05).

Thus at least three of the peptides that are expressed by more fungal species were shown to be effective vaccines in mice against a *C. albicans* challenge. It is expected that they would similarly be effective against the other fungal species that express the same peptide. These peptides can also be linked to the β-(Man)₃ glycan and/or to tetanus toxoid by the methods described below to increase the vaccine effectiveness.

Example 11

Design and Use of Methylated Fba Peptides

In an attempt to move the original Fba vaccine to a more acceptable formulation for human use, changes were made to the Fba peptide. First, the Fba peptide was conjugated to a multiple antigenic peptide (MAP), of which the lysine core bears eight copies of the Fba peptide epitope. Second, partial N-methyl scanning of the Fba amino acids and insertion of cysteine residues were applied. Without wishing to be bound by this theory, we believe that these modifications would increase in vivo half-life and immunogenicity of the Fba peptide. The MAP experiments were disappointing (data not shown). For the Fba derivatives, the results using either alum and/or MPL as an adjuvant were more encouraging. All the synthetic peptides were commercially made by GenScript Company.

Using N-methyl scanning, sites were selected for the introduction of cysteine residues in the Fba 14 amino acid peptide to hopefully increase in vivo half-life and immunogenicity. Eleven peptides were synthesized commercially as shown in FIG. 16, and in Table 1 below. Peptide 1 is the original Fba peptide (SEQ ID NO:1). Peptides 2-9 (SEQ ID NOS:11-18) each had one of the original amino acids methylated but at different positions as described in Table 1. Peptide 10 had two amino acids methylated (SEQ ID NO:19). Peptide 11 (SEQ ID NO:20) had two extra cysteines inserted, one at position 5 and one at position 8.

TABLE 1

Modified Fba Peptides

| Peptide No. | Sequences | SEQ ID NO: |
|---|---|---|
| Pep1 (Fba) | YGKDVKDLFDYAQE | SEQ ID NO: 1 |
| Pep2 | YGKDVKDLFDYAQE (methylated at position 1) | SEQ ID NO: 11 |
| Pep3 | YGKDVKDLFDYAQE (methylated at position 2) | SEQ ID NO: 12 |
| Pep4 | YGKDVKDLFDYAQE (methylated at position 3) | SEQ ID NO: 13 |
| Pep5 | YGKDVKDLFDYAQE (methylated at position 5) | SEQ ID NO: 14 |
| Pep6 | YGKDVKDLFDYAQE (methylated at position 6) | SEQ ID NO: 15 |
| Pep7 | YGKDVKDLFDYAQE (methylated at position 8) | SEQ ID NO: 16 |
| Pep8 | YGKDVKDLFDYAQE (methylated at position 9) | SEQ ID NO: 17 |
| Pep9 | YGKDVKDLFDYAQE (methylated at position 11) | SEQ ID NO: 18 |
| Pep10 | YGKDVKDLFDYAQE (methylated at positions 1 and 8) | SEQ ID NO: 19 |
| Pep 11 | YGKDCVKCDLFDYAQE (cysteine added at positions 5 and 8) | SEQ ID NO: 20 |

These modified Fba peptides were used to test reactivity with anti-Fba immune sera. A microtiter plate was coated with 11 peptides, and anti-Fba serum was tested for its reactivity with these Fba derivatives as described above. The same ELISA was used to test the reaction of anti-Fba antibodies in immune sera with all the 11 peptides, but the plate was coated with peptides 1-11, instead of the original Fba peptide. As shown in FIG. 16, all the modified Fba peptides were recognized by antibody specific for the original Fba. This indicates all of them retained immunoreactivity and may be useful as antigens for vaccines.

Figure 18A:
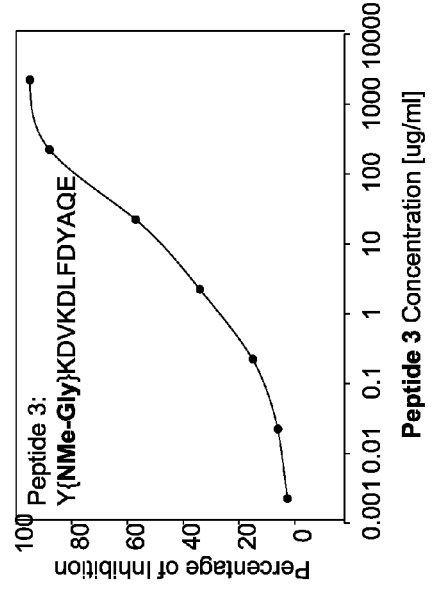
Figure 18B:
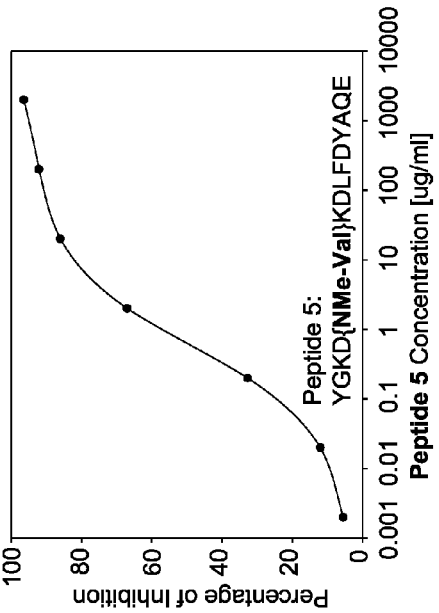
Figure 18C:
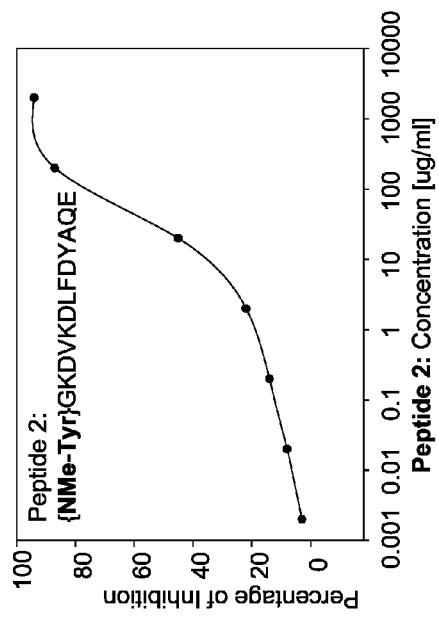
Figure 18D:
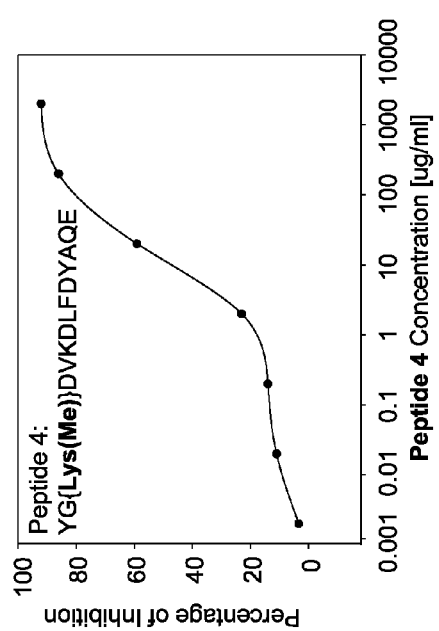
Figure 18E:
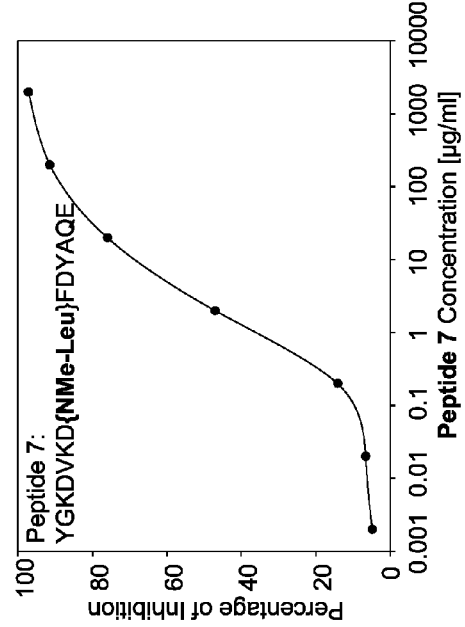
Figure 18F:
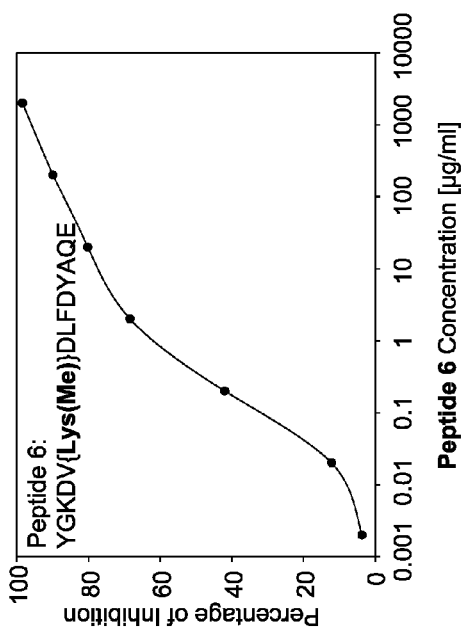
Figure 18G:
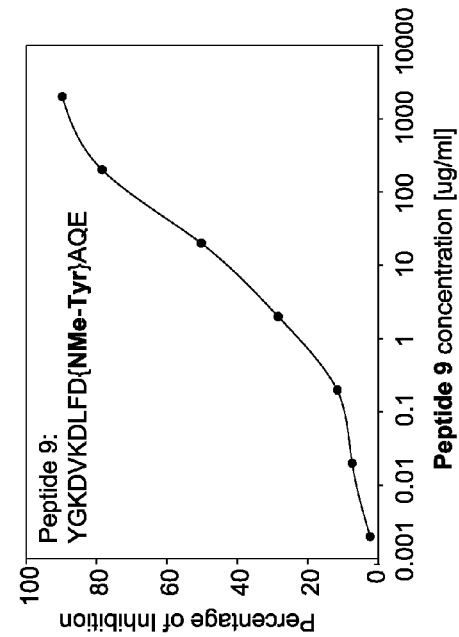
Figure 18H:
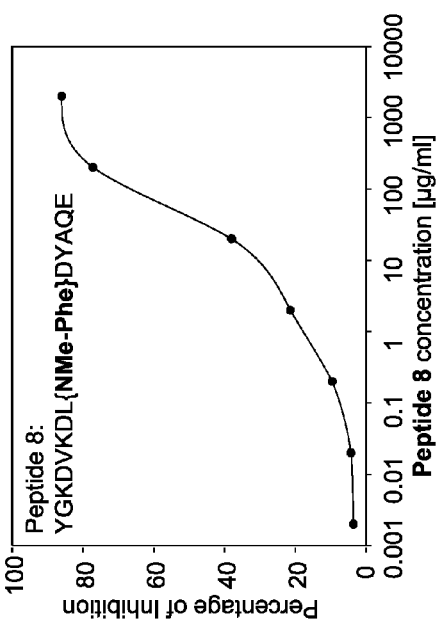
Figure 18J:
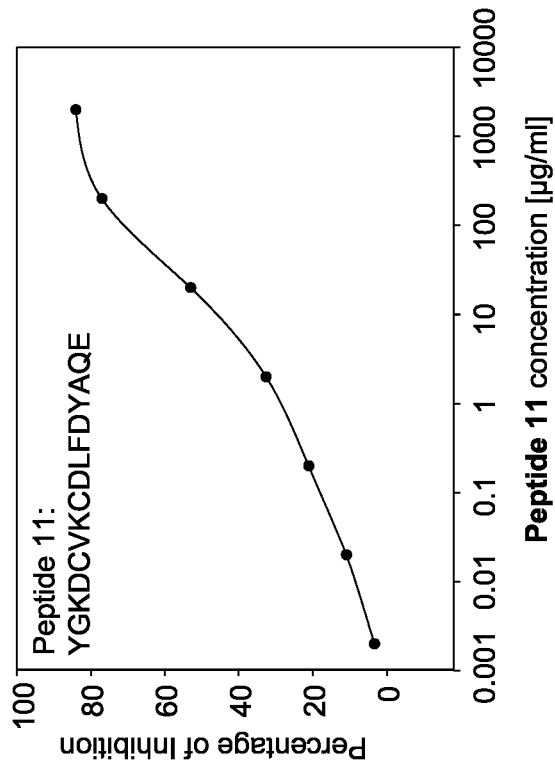
Figure 18I:
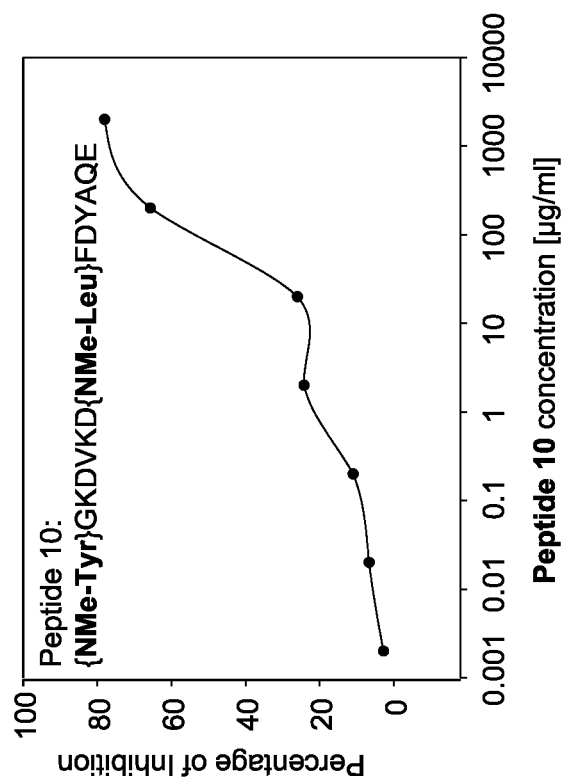

The specificity of anti-Fba antibodies in immune sera was tested for the modified Fba peptides as determined by ELISA inhibition assay. The results for the same test with Fba peptide is shown in FIG. 17. Peptide 1, original Fba, which was used as an inhibitor, was included as a positive control. The inhibition curve of FIG. 17 serves to compare the curves with the other modified peptides 2-11. FIGS. 18A, 18B, 18C, and 18D show the results of ELISA inhibition assays for peptide 2, peptide 3, peptide 4 and peptide 5, respectively. Each methylated peptide was used as an inhibitor in the designated assay. As shown in FIGS. 18A-18D as compared to FIG. 17, methylation at position 1, 2, 3, or 5 seems to have little effect on peptide-antibody binding. The reaction is dose-dependent for each group, indicating anti-Fba antibodies in immune sera were specific for the modified peptides. Similarly, as shown in FIGS. 18E, 18F, 18Q and 18H, methylation of the Fba peptide at position 6, 7, 8, or 9, respectively, did not have significant effect on antibody binding to peptides. Finally, as shown in FIGS. 18I and 18J, peptide 10 (methylated at position 1 and 8) and peptide 11 (two cysteine insertions at position 5 and 8), respectively, bound well to antibody. The binding of peptide 11, which has two extra cysteines may indicate that the binding site of Fba with antibody is located at the carboxyl part of the peptide.

To test for antibody response as measured using ELISA from serum of mice immunized with the modified peptides, two mice per group with 11 groups for peptides 1 to 11 were used. Mice were i.p. injected three times with 15 μg peptide mixed with 50 μg alum, and each injection spaced three weeks apart. As shown in FIG. 19, all modified Fba peptides were able to induce antibody responses, but the response was not as strong as Fba peptide 1.

All of the modified Fba peptides were tested in mice, using different routes of immunization (intraperitoneal (i.p.) or subcutaneous (s.c.)) and different combinations of human acceptable adjuvants (alum alone or alum+MPL). Each experiment involved two mice per group and was conducted to test if any of peptides induced robust anti-Fba antibody responses in animals. FIG. 20A shows the anti-Fba antibody response in mice immunized with the Fba derivatives by i.p. injection and using peptides in alum. FIG. 20B shows the anti-Fba antibody response in mice immunized with the Fba derivatives by i.p. injection and using peptides in alum and MPL. FIG. 20C shows the anti-Fba antibody response in mice immunized with the Fba derivatives by s.c. injection and using peptides in alum. FIG. 20D shows the anti-Fba antibody response in mice immunized with the Fba derivatives by s.c. injection and using peptides in alum and MPL. As shown in FIGS. 20A-20D, all the modified Fba peptides were able to induce antibody responses, but again not as strong as the original Fba peptide. The immunization route of subcutaneous and a combination of alum & MPL induced the highest antibody responses. For several peptides, better antibody responses were observed when the serum was serially diluted to obtain actual antibody titers. These modified peptides may be used as vaccines for candidiasis. These modified peptides can also be linked to the β-(Man)$_3$ glycan and/or to tetanus toxoid by the methods described below to increase the vaccine effectiveness.

Section B: Conjugate Vaccines

Example 12

Materials and Methods

*Candida albicans* Strains.

*C. albicans* 3153A and SC5314 (ATCC) were grown as stationary-phase yeast cells in glucose-yeast extract-peptone broth at 37° C., washed and suspended to the appropriate cell concentration (5×106/ml) in Dulbecco's PBS (DPBS; Sigma), and used to infect mice intravenously (i.v.) as described [25, 29]. *C. albicans* strain 3153A was used also for serum antibody absorption, immunofluorescence staining and flow cytometric analysis.

Mouse Strains.

Inbred strains BALB/c and C57BL/6, and outbred Swiss Webster (ND4) female mice (NCI Animal Production Program or Harlan) 5 to 7 weeks old were used. Mice were maintained and handled in accordance with protocol approved by the Institutional Animal Care & Use committee (IACUC) regulations at Children's Hospital Research Institute in New Orleans.

Synthesis of the Conjugate Vaccine.

The glycoconjugate vaccine (GV) and the control vaccine lacking the mannotriose component (PV) were synthesized from the advanced building blocks as summarized in FIG. 29. The compounds in FIG. 29 are numbered to match the numbered compounds in the more detailed synthesis shown in FIGS. 30A-30E. β-1,2 mannotriose derivatized with a triethylene glycol spacer (Compound 3) was synthesized as previously described [62]. The T-cell tetradecameric peptide (Fba) was assembled on a peptide synthesizer and a triethylene glycol tether was introduced at the C terminal end followed by a single lysine residue which was derivatized on its side chain by a thioacetic acid residue. This gave the building blocks 2a or 2b. Bromoacetate groups were introduced on approximately 20 of the lysine residues present in tetanus toxoid (State Serum Institute, Cophenhagen) to give compound 5. GV was assembled by reacting 3 with 2a and then conjugating this product with 5. PV was prepared by conjugating 2b with 5. A more detailed account of this synthesis is shown below in Example 21.

Immunizations of Mice.

Conjugates β-(Man)$_3$-Fba or β-(Man)$_3$-Fba-TT were administered at a subcutaneous (s.c.) location in the nape of the neck. The conjugates were given alone or as a mixture made either with alum (aluminum hydroxide gel, Sigma) or MPL (Lipid A, monophosphoryl, Sigma) or as a combination of both adjuvants. Negative control groups of mice were given DPBS buffer or adjuvant only. Immunization doses and schedules were 100 µl of 2.5 µg or 10 µg of either conjugate alone, or as a mixture containing either conjugate along with 50 µg alum or 10 µg MPL on days 1, 21 and 62. In some experiments the two adjuvants were combined and mixed with antigen for the priming and booster doses. Serum samples were collected 14 days after each immunization and tested by ELISA.

Serological Assays.

Immune sera were analyzed for antibody titers after each immunization as described below. Although the titers increased after each dosing, the most profound changes were usually observed after the first booster, which is the result chosen to show for comparison of vaccine responses between the various groups.

For DC/CFA-based immunizations, DCs were pulsed in vitro with β-(Man)$_3$-Fba vaccine as described above and previously [53]. The mice were given a priming dose and boosted at day 14 with fresh antigen-pulsed DCs and boosted a second time at day 28 with antigen (2.5 µg) emulsified in complete Freund adjuvant (CFA) given subcutaneously (s.c.). Control groups consisted of mice given DPBS, DC, or DC+CFA alone at the time of priming and boosters. For β-(Man)$_3$-Fba, Fba-TT or (β-(Man)$_3$-Fba-TT administered alone or with alum or MPL, control groups were given adjuvant alone or DPBS buffer. Serum samples were collected 14 days after each immunization, diluted 1:100 and tested by ELISA on plates coated with cell wall mannan extract from *C. albicans*, or Fba-MAP peptide (GenScript) or β-(Man)$_3$-BSA as previously described [53]. Briefly, *C. albicans* mannan extract, which is composed mainly of mannan, or synthetic β-(Man)$_3$ coupled to BSA was dissolved at 4 µg/ml in carbonate buffer (pH 9.6); Fba-MAP (GenScript) was dissolved at 10 µg/ml in carbonate coating buffer (pH 9.5). Each was used to coat 96-well ELISA plates for testing duplicate 1:100 dilutions of samples of each immune serum and control sera. Color development for each well was achieved by secondary antibody, goat anti-mouse polyvalent immunoglobulin (IgG, IgA, IgM) peroxidase conjugated antibody (diluted 1:10,000 in PBST) (Sigma) and substrate (O-phenylenediamine and $H_2O_2$); OD reading was determined at 492 nm. To determine dilution endpoint ELISA titers, serial 2-fold dilutions of sera in blocking buffer were prepared. The endpoint ELISA titer was taken as the reciprocal of the last serum dilution with an OD reading at least two-fold greater than the mean OD of negative control samples plus twice the standard deviation.

For antibody isotype and subclass determinations, peroxidase-conjugated rabbit anti-mouse heavy chain specific IgM, IgG1, IgG2a, IgG2b, and IgG3 (Rockland, Pa.) were diluted 1:10,000 in blocking buffer and added to the appropriate wells, followed by addition of O-phenylenediamine substrate and $H_2O_2$ for color development and absorbance as before.

Fungal Challenge and Assessment of Protection.

Two weeks after the second boost, immune and control mice were infected i.v. with a lethal dose of live *C. albicans* yeast cells (5×10$^5$ in 0.1 ml of DPBS) prepared as described above and previously [53]. Passively immunized mice (below) also received the same challenge dose. Protection was evaluated by monitoring animal survival for 50-120 days, depending on the experiment. The mice were monitored for development of a moribund state, defined as being listless, disinterested in food or water, and nonreactive to finger probing. At the time that a mouse was deemed moribund, it was sacrificed and their kidneys were homogenized in DPBS and plated onto a nutrient agar to determine colony forming units of fungal cells (CFUs). After 50-120 days, the experiments were terminated and all the survivors at that time were sacrificed and their kidneys were assessed for CFU as before. The lowest limit of detection for the CFU assay was 50 CFU per kidney pair.

Passive Transfer of Immune Sera.

Immune sera were obtained from vaccinated mice, pooled and stored at −20° C. or absorbed before freezing with *C. albicans* 3153A yeast cells as described above or previously [53, 25]. Immune sera pre-absorbed with yeast or DBPS buffer were used as passive transfer negative controls. Pre-absorbed immune sera were tested and found negative for antibodies against both β-(Man)$_3$ and Fba peptide by ELISA as described above. Naïve BALB/c mice received 0.5 ml at an intraperitoneal (i.p.) location of full-strength immune serum or control serum or DBPS buffer. Four hours later, all mice were challenged i.v. with *C. albicans* (5×10$^5$ yeast cells). All animals received a second dose (200 µl) of serum or negative control material i.p. 24 h after the first dose. Infected mice were sacrificed when they became moribund and their kidneys were assessed for CFUs as above.

Flow Cytometric Analysis and Immunofluorescence Microscopy.

Distribution of the β-(Man)$_3$ and Fba peptide epitopes on yeast cells was determined by use of immune serum for flow cytometric analysis and indirect immunofluorescence. One hundred microliters of immune serum (1:100 dilution in 1% BSA/DPBS) was added to a pellet of *C. albicans* yeast cells (5×10$^6$) that was prewashed with DPBS buffer three times. The yeast cells were suspended in the immune serum [from β-(Man)$_3$-Fba-TT immunized mice] preparation and incubated while shaking by rotation at room temperature (RT, 22-24° C.) for 1-2 h. After incubation, the yeast cells were washed with DPBS three times, suspended in 200 µl of fluorescein-labeled goat anti-mouse IgM (µ-chain specific; Sigma) (stock solution, 1 mg/ml; working solution, 20 µg/ml of DPBS) and incubated at RT described above for 0.5 h. The yeast cells were washed with DPBS three times and suspended in 500 µl of DPBS. Flow cytometry was performed using a BD Biosciences FACSVantage SE equipped with an argon laser excitation at 488 nm. 10,000 cells in each sample were analyzed (CellQuest Pro software).

For immunofluorescence assays, the fungal cells were immunostained and washed as described above and suspended in the 200 µl DPBS buffer. The cells were observed by confocal microscopy (LSM 510, Zeiss). The distribution of the β-(Man)$_3$ and Fba peptide epitopes on the yeast cell surface was compared to that obtained with yeast cells fluorescently stained for detection of the MAb B6.1 epitope. Negative controls included showing non-reactivity of an irrelevant isotype control IgM MAb S-9 [45] (data not shown) and use of fluorescein-labeled goat anti-mouse secondary antibody only. As an additional control, pre-absorbed immune serum prepared as described above was tested for the binding reactivity to the *C. albicans* cell surface.

Statistical Analysis.

Data were analyzed by GraphPad Prism 4 software (GraphPad Inc.). ELISA data were assessed for statistical significance by curve fit analysis. Differences in median survival time and in survival rates in *C. albicans*-challenged mice were analyzed by nonparametric two-tailed Mann-Whitney U test or Fisher's exact test, respectively. Differences in survival curves were assessed by the log-rank test. Data from CFU counts, in both in vitro and in vivo experiments, were analyzed by two-tailed Student's t test. Multiple comparisons were made by analysis of variance (one-way ANOVA) followed by Newman-Keuls post-test.

Example 13

Protective Efficacy of β-(Man)$_3$-Fba Conjugate Vaccine in a Different Mouse Strain and Against an Additional *C. albicans* Strain As previously described, the β-(Man)$_3$-Fba conjugate vaccine induced strong antibody responses and protective immunity in BALB/c mice [53] that express the H-2d MHC haplotype and have a Th-2 immunologic bias [3]. C57BL/6 mice express an H-2b MHC haplotype, are more prone to Th1 responses and supposedly more resistant to disseminated candidiasis than are BALB/c mice [3]. As described above in Example 5, using the Fba peptide, immune responses were similar in both mouse strains—BALB/c and C57BL/6. Dendritic cells were derived in vitro as described above and previously [53] and used the same immunization DC/CFA-strategy on the C57BL/6 mice as was used on BALB/c mice [53], which included a priming dose followed by two boosters; the last booster consisted of the vaccine emulsified in CFA. C57BL/6 mice responded to the vaccine by making specific antibody against each of the two vaccine epitopes, i.e., the β-(Man)$_3$ and the Fba peptide (data not shown). Following the first booster, an isotype switch from IgM to IgG occurred in response to each epitope. The immunized C57BL/6 mice showed 80% survival throughout the 120 days post challenge and survived significantly longer (p<0.001) as compared to the control groups of mice given DPBS buffer, DC or DC+CFA (FIG. 21A). The survival data were consistent with the trend of colony forming units (CFU) in kidney homogenates. That is, immunized C57BL/6 mice had greatly reduced or non-detectable kidney CFU as compared to controls that were sacrificed when they became moribund following i.v. challenge with the fungus (FIG. 21B). Indeed, the protection in C57BL/6 mice was similar to that which we observed for BALB/c mice [53].

To answer whether antibody responses were responsible for the protection, antisera were collected from separate groups of immunized mice and transferred i.p. to naïve mice 4 h before i.v. challenge with a lethal dose of *C. albicans* strain 3153A. Control groups were given either immune sera pre-absorbed with live *C. albicans* yeast cells or DPBS buffer prior to the challenge. The immune serum donors, which were immunized with β-(Man)$_3$-Fba by the DC/CFA method, were used as positive controls for protection. After challenge, immunized mice and mice treated with the antiserum had prolonged survival times as compared to the two control groups (p<0.05) (FIG. 21C), and as expected, mice that received the antiserum had significantly reduced fungal counts in their kidneys (p<0.05) (FIG. 21D). These data provide strong evidence that antibodies are responsible, at least in part, for the vaccine-induced protection against a lethal challenge with the fungus in C57BL/6 mice.

*C. albicans* strain 3153A was used in our previous studies [7, 17, 19]. To test if DC/CFA vaccination with the β-(Man)$_3$-Fba protects C57BL/6 mice challenged with another *C. albicans* strain, similar to Example 4 above for Fba peptide, we challenged immunized mice with *C. albicans* strain SC5314, a clinical isolate commonly used in research. As a positive control, a group of immunized mice was challenged with strain 3153A. Similar protection patterns were observed in both groups of mice regardless of the challenge strain (FIG. 21E). In addition to prolonged survival times, immunized groups had reduced or non-detectable CFUs in their kidneys as compared to non-immune mice (data not shown). These results are similar for both the Fba peptide and the β-(Man)$_3$-Fba conjugate and to those we observed from BALB/c mice challenged with the 3153A strain [53, 52]. The above experiments, and those in Examples 4 and 5, are important as they show that vaccine-induced antibody protection is not animal or fungal-strain dependent.

Example 14

Immunization with β-(Man)$_3$-Fba Combined with Alum or MPL Induced Modest Antibody Responses and Slight Protection Although the DC/CFA-based immunization approach was successful in mice for protection against disseminated candidiasis, the use of DC and complete Freund adjuvant are inappropriate for human use. To test new adjuvants suitable for human use, the β-(Man)$_3$-Fba conjugate was administered as a mixture with either alum or MPL adjuvants in BALB/c mice. Serum samples were collected 14 days after immunization, diluted 1:100 and tested by ELISA on plates coated with synthetic β-(Man)$_3$ or Fba-MAP. After the first booster immunization, immune sera from vaccinated mice showed modest antibody responses (OD values of a 1/100 serum dilution: 0.7-0.9) to Fba peptide (FIG. 22A) and relatively weak antibody responses (OD values of a 1/100 serum dilution: 0.45-0.55) to β-(Man)$_3$ epitope (FIG. 22B) As shown in FIG. 22C, the survival was also slightly extended in mice that received β-(Man)$_3$-Fba in MPL and slight protection was observed when alum was used as the adjuvant as compared to DPBS or adjuvant unimmunized controls.

Following the second booster immunization, an isotype switch from IgM to IgG of either β-(Man)$_3$ or Fba specific antibodies was low to negligible in immune sera (data not shown, results summarized in Table 2, below), which suggested that an immune memory response had not occurred. In addition, the β-(Man)$_3$-Fba vaccinated groups had insignificantly longer survival times as compared to the two non-immunized control groups after challenge with a lethal dose of *C. albicans* cells (p=0.77) (FIG. 22C).

TABLE 2

Antibody isotype distribution of responses to Fba and β-(Man)3

| Sera induced by vaccines | Anti β-(Man)$_3$ | Anti Fba-peptide |
|---|---|---|
| β-(Man)$_3$-Fba-TT with MPL | IgM; IgG1, IgG2a; IgG2b | IgM; IgG1 |
| β-(Man)$_3$-Fba-TT with alum | IgM; IgG1; IgG2a | IgM; IgG1; IgG2a |
| β-(Man)$_3$-Fba-TT | IgM; IgG1; IgG2a | IgM; IgG1; IgG2a |
| β-(Man)$_3$-Fba | IgM | IgM |
| β-(Man)$_3$-Fba with alum | IgM | IgM |
| β-(Man)$_3$-Fba with MPL | IgM | IgM |
| β-(Man)$_3$-Fba + DC + CFA | IgM; IgG1 | IgM; IgG1 |

In an attempt to increase the antibody and protective responses, the dose of β-(Man)$_3$-Fba conjugate was increased from 2.5 μg to 10 μg in the β-(Man)$_3$-Fba+alum formulation. FIGS. 23A-23C show a comparison of DC/CFA and alum as adjuvants for induction of immune responses to the β-(Man)$_3$-Fba conjugate vaccine. Serum samples were collected 14 days after immunization, diluted 1:100 and tested by ELISA on plates coated with either synthetic Fba-MAP or β-(Man)$_3$. Immune sera from mice immunized with the β-(Man)$_3$-Fba DC/CFA showed greater antibody titers to both the Fba peptide (FIG. 23A) and the β-(Man)$_3$ epitopes (FIG. 23B) than sera from groups that received β-(Man)$_3$-Fba in alum. As shown in FIG. 23C, a high degree of protection was induced by the β-(Man)$_3$-Fba pulsed DCs, and slight protection was observed when alum was used as the adjuvant as compared to DPBS, DC+CFA or alum adjuvant unimmunized controls.

The levels of anti-Fba peptide (FIG. 23A) and anti-β-(Man)$_3$ (FIG. 23B) were markedly less than antibody levels (OD values of a 1/100 serum dilution: 1.7-1.9) in sera from control animals immunized with the β-(Man)$_3$-Fba+DC/CFA. Likewise, when titers were assessed by end-point dilution, the immune sera from the positive control group showed significantly greater antibody responses for both epitopes (Table 3, below). Interestingly, even though the antibody titers against both epitopes in response to the 10 microgram dosage was greater than the response to the 2.5 μg dose, disease protection was not observed to the extent of protection induced by the DC/CFA immunization approach (FIG. 23C). In summary, the greatest antibody responses occurred in mice that received the β-(Man)$_3$-Fba+DC/CFA, the animals of which also showed evidence of an IgM-IgG shift (Table 3, below) and the highest degree of protection [7].

TABLE 3

ELISA titers against microtiter wells coated with synthetic β-(Man)3 and Fba peptide A. Wells coated with synthetic β-(Man)$_3$

| Sera from vaccine groups | anti-β-(Man)$_3$ ELISA titers* (*n = 5 mice per group) | | | | |
|---|---|---|---|---|---|
| β-(Man)$_3$-Fba-TT + Alum | 12,800 | 25,600 | 25,600 | 25,600 | 25,600 |
| β-(Man)$_3$-Fba-TT + MPL | 12,800 | 12,800 | 25,600 | 12,800 | 25,600 |
| β-(Man)$_3$-Fba-TT | 12,800 | 25,600 | 25,600 | 12,800 | 25,600 |
| β-(Man)$_3$-Fba + Alum | 1,600 | 400 | 400 | 400 | 800 |
| β-(Man)$_3$-Fba + MPL | 1,600 | 800 | 800 | 400 | 400 |
| β-(Man)$_3$-Fba | 400 | 400 | 400 | 400 | 400 |
| β-(Man)$_3$-Fba + DC | 51,200 | 25,600 | 25,600 | 25,600 | 51,200 |

B. Wells coated with Fba peptide

| Sera from vaccine groups | anti-Fba peptide ELISA titers* (*n = 5 mice per group) | | | | |
|---|---|---|---|---|---|
| β-(Man)$_3$-Fba-TT + Alum | 51,200 | 25,600 | 51,200 | 51,200 | 25,600 |
| β-(Man)$_3$-Fba-TT + MPL | 51,200 | 25,600 | 25,600 | 25,600 | 25,600 |
| β-(Man)$_3$-Fba-TT | 51,200 | 25,600 | 25,600 | 51,200 | 25,600 |
| Fba-TT + Alum | 400 | 400 | 200 | N/A | N/A |
| Fba-TT + MPL | 400 | 400 | 200 | N/A | N/A |
| β-(Man)$_3$-Fba + Alum | 800 | 800 | 1,600 | 800 | 800 |
| β-(Man)$_3$-Fba + MPL | 800 | 800 | 800 | 400 | 800 |
| β-(Man)$_3$-Fba | 400 | 400 | 400 | 400 | 400 |
| β-(Man)$_3$-Fba + DC | 51,200 | 102,400 | 51,200 | 51,200 | 102,400 |

Example 15

Addition of Tetanus Toxoid (TT) to the Vaccine, β-(Man)$_3$-Fba-TT, Markedly Enhanced Antibody Responses to Both Epitopes in the Presence of Alum or MPL In an attempt to improve immunogenicity of the glycopeptide vaccine in the presence of adjuvant suitable for human use, the β-(Man)₃-Fba conjugate was modified by coupling it to tetanus toxoid designated as β-(Man)₃-Fba-TT and tested with the peptide conjugate Fba-TT. Both conjugates were administered as mixtures with alum or MPL. Negative control groups included adjuvant only and DPBS buffer only. FIGS. 24A and 25B show that vaccination with β-(Man)₃-Fba-TT in either alum or MPL markedly increased both β-(Man)₃ and Fba peptide-specific antibody titers in sensitized mice as compared to controls. Serum samples were collected 14 days after immunization, diluted 1:100 and tested by ELISA on plates coated with cell wall mannan or peptide. MAbs B6.1 and E2-9 that are specific for β-(Man)₃ and Fba, respectively, were used as positive controls.

After the first booster, mice immunized with β-(Man)₃-Fba-TT prepared in either alum or MPL produced robust antibody responses against both the Fba peptide (FIG. 24A) and the β-(Man)₃ epitopes (FIG. 24B), titers of which were 100 fold greater than that of sera from groups that received Fba-TT (p<0.001) (Table 3, above), the latter of which responded about the same as animals that received Fba in alum without TT (FIG. 24A). After the first booster, IgM and IgG antibodies against both epitopes were detected in the sera of mice immunized with β-(Man)₃-Fba-TT with added alum or MPL adjuvants (Table 2), whereas very low levels of anti-Fba IgM and IgG antibodies were detected in the sera of mice that received Fba or Fba-TT in adjuvant. No antibody against the epitopes was detectable in any of the negative (i.e., adjuvant or DPBS mice) control sera (data not shown). Although the Fba-TT as linked by the method described in Example 21 did not give a good response, this was only an initial trial using only one type of linker for the Fba and TT. It is believed that linking tetanus toxoid by other methods known in the field (63, 64, 65) or to tetanus $T_H$ epitopes (e.g., U.S. Patent Application Publication No. 2004/0101534 can produce a peptide conjugate that would give a stronger response.

Example 16

The β-(Man)₃-Fba-TT Conjugate Vaccine Induced High Antibody Responses and Protection Even in the Absence of Adjuvant To determine whether the immunogenicity of β-(Man)₃-Fba-TT vaccine was dependent on additional adjuvant, β-(Man)₃-Fba-TT was administered alone and the response of these mice was compared to those that received the vaccine as a mixture made with alum or MPL adjuvants. FIGS. 25A-D show results of using β-(Man)₃-Fba-TT conjugate with or without adjuvant markedly as analyzed by antibody titers and protection against disseminated candidiasis. Mice immunized with β-(Man)₃-Fba-TT prepared in either alum or MPL, or without adjuvant developed robust antibody responses against both the Fba peptide (FIG. 25A) and the β-(Man)₃ epitope (FIG. 25B). FIG. 25C shows that protective immunity was induced by β-(Man)₃-Fba-TT when either alum or MPL was used as the adjuvant. Protection was nearly as great even when adjuvant was omitted as compared to DPBS or adjuvant only controls (P<0.01). FIG. 25D shown that immunized mice had reduced or non-detectable CFUs per kidney pairs compared to control groups (P<0.001).

Thus, mice that received the vaccine prepared in either adjuvant responded as expected by making robust antibody responses. Surprisingly, mice that received the β-(Man)₃-Fba-TT without adjuvant responded only slightly, but not significantly, less than those that received the vaccine plus adjuvant (FIGS. 25A and 25B). Importantly, all three groups of mice, vaccinated with β-(Man)₃-Fba-TT conjugate vaccine with or without additional adjuvant, showed a high degree of protection against a lethal challenge with *C. albicans* (FIG. 25C). The induced protective immunity was evidenced by significantly prolonged survival times (p<0.005) and reduced kidney fungal burden (p<0.001) as compared to control groups that received only adjuvants or DPBS buffer prior to challenge (FIG. 25D). These results showed the self-adjuvanticity power of the β-(Man)₃-Fba-TT vaccine.

Example 17

Anti-β-(Man)₃-Fba-TT Immune Sera Induced by Non-DC/CFA-Based Immunization Approaches Provided Passive Protection Passive transfer experiments have shown that antibodies induced by the DC/CFA-based immunization approach are responsible for protection against disseminated candidiasis. To confirm that vaccine-induced antibodies are protective regardless of the use of dendritic cells, immune sera were collected and pooled from β-(Man)₃-Fba-TT (with or without alum or MPL adjuvants) immunized mice and transferred i.p. to naïve mice 4 h before i.v. challenge with a lethal dose of *C. albicans*. Control groups were given either immune serum pre-absorbed with live *C. albicans* yeast cells or DPBS buffer prior to the challenge. Antibodies were tested against the β-(Man)₃ and Fba epitopes before and after absorption with yeast cells. Immune serum donors, which were immunized with β-(Man)₃-Fba-TT conjugate vaccine, were used as a positive control for protection. After challenge, immunized positive control mice and mice treated with the antiserum had prolonged survival times as compared to the two negative control groups (p<0.01) (FIG. 26A), confirming that induced antibodies were protective and that their induction was not dependent on the use of dendritic cells or CFA during the immunizations. Consistently, mice that received the antiserum had significantly fewer fungal counts in their kidneys compared with the infectious burden in mice that were given DPBS or pre-absorbed serum prior to challenge (p<0.001) (FIG. 26B).

Example 18

Immunization Induced an Isotype Switch from IgM to IgG for Antibodies Specific for Either Fungal Epitope in the Vaccine Conjugate Antibody isotype responses were compared to both the glycan and peptide epitopes induced by the β-(Man)₃-Fba conjugate when the DC/CFA-based immunization approach was employed to that produced by the β-(Man)₃-Fba-TT modified conjugate administered with alum or MPL or when given alone (Table 2, above). β-(Man)₃-Fba+DC/CFA and β-(Man)₃-Fba-TT immunized mice produced antibodies to both the β-(Man)₃ epitope and Fba peptide, and the isotype analysis revealed an abundance of IgM and IgG subclasses in the immune sera against both epitopes, which is consistent with the induction of a T cell-dependent memory immune response.

The isotype distribution of antibodies specific for the fungal epitopes differed depending on the adjuvant system (Table 2). Whereas IgM and IgG1 responses to β-(Man)₃ were induced regardless of the presence of adjuvant, an IgG2a response to the glycan epitope was induced by β-(Man)₃-Fba-TT with or without the use of alum or MPL, but IgG1 was the only subclass detectable in mice immunized by the DC/CFA approach. Only mice immunized with the β-(Man)₃-Fba-TT mixed with MPL produced an IgG2b response to the glycan epitope. Antibody IgM and IgG1 isotype responses to the Fba peptide were similar for mice immunized with the β-(Man)$_3$-Fba regardless of the adjuvant system, however, IgG2a specific for the peptide epitope was induced only by β-(Man)$_3$-Fba-TT with alum or when no adjuvant was used. No IgG2a isotype was detected against the peptide when MPL was the test adjuvant. The level of protection observed against disseminated candidiasis was similar in mice immunized with the glycan-peptide conjugate in the DC/CFA approach, or in mice immunized with the glycan-peptide-TT with or without alum or MPL, which indicated that the protective antibodies are likely to be primarily of the IgM and IgG1 isotypes.

Example 19

The Glycopeptide-TT Conjugate is Immunogenic and Protective Against Disseminated Candidiasis in Outbred Mice The efficacy of the β-(Man)$_3$-Fba-TT conjugate vaccine against disseminated candidiasis was also demonstrated in outbred mice. Since a combination of MPL and alum may enhance the vaccine response by rapidly triggering a local cytokine response leading to an optimal activation of antigen-presenting cells (APCs), Swiss Webster mice were immunized with the β-(Man)$_3$-Fba-TT conjugate alone or as a mixture with both alum and MPL. Negative control mice were immunized with the adjuvant combination or DPBS only. Outbred Swiss Webster (01S60) mice were immunized with the β-(Man)$_3$-Fba-TT conjugate alone or mixed with adjuvants alum and MPL; control mice were immunized with adjuvants (alum+MPL) only or DPBS buffer.

The β-(Man)$_3$-Fba-TT, with or without adjuvant, induced robust and consistent antibody responses against both the β-(Man)$_3$ (FIG. 27A) and the Fba epitopes (FIG. 27B) in immunized outbred mice. Fourteen days following the last booster, immunized mice were infected via the tail vein with a lethal dose of C. albicans 3153A, as described above. Similar to the findings in BALB/c mice, the outbred mice vaccinated with β-(Man)$_3$-Fba-TT conjugate vaccine, when administered alone or with alum and MPL, markedly improved the survival of infected mice (FIG. 27C). Protective immunity was induced by β-(Man)$_3$-Fba-TT with or without adjuvant as noted by their prolonged survival time as compared to control mice that received DPBS or adjuvants alone (P<0.01). Consistently, the immunized mice had significantly lower live fungal cells in their kidneys as compared to negative controls (p<0.001) (FIG. 27D).

Example 20

Antibodies in Immune Sera Bind Yeast and Hyphal Forms of C. albicans

Immune serum from animals immunized with the β-(Man)$_3$-Fba-TT conjugate contained antibodies specifically reactive with the cell surface of yeast forms as demonstrated by flow cytometric analyses. Immune serum from β-(Man)$_3$-Fba-TT vaccinated mice detected the presence of the vaccine epitopes on the surface of C. albicans, as shown by flow cytometry. FIG. 28A shows antibodies in immune sera binding to the both epitopes expressed on the C. albicans cell surface, and shown that the reactivity of immune serum with live C. albicans cells to that of MAb B6.1, which is specific for the C. albicans cell surface epitope β-(Man)$_3$. Control serum was non-immune serum from mice that received adjuvant only. FIG. 28B shown pre-absorbed MAb B6.1 and pre-absorbed immune sera were not reactive with fungal cell surface. FIG. 28C are micrographs from confocal microscopic analyses, confirming that antibodies in immune serum detected the vaccine epitopes on the surface of yeast forms, but were also reactive with the surface of hyphal forms of C. albicans. The epitope display was similar to that due to fungal reactivity with MAb B6.1, which is specific for β-(Man)$_3$ and was used as a positive immunofluorescence control. As an additional negative control, immune serum pre-absorbed with C. albicans 3153A yeast cells did not react with either yeast or hyphal forms of C. albicans.

Thus, a fluorescence shift similar in magnitude to the control antibody, MAb B6.1, was observed upon testing of the immune serum (FIG. 28A). This reactivity of immune serum was removed by pre-absorption with C. albicans yeast forms (FIG. 28B). The binding pattern was similar with immune sera collected from mice vaccinated with β-(Man)$_3$-Fba-TT alone, or when mixed with either alum or MPL (data not shown).

Microscopic observations after immunofluorescence staining with anti-β-(Man)$_3$-Fba-TT conjugate immune serum showed reactivity with both yeast and filamentous forms of C. albicans strain 3153A (FIG. 28C). The microscopic analysis confirmed the flow cytometry results and extended the observations to include hyphal forms of the fungus. The specific antibody reactivity was again confirmed by the absence of fluorescence by immune serum pre-absorbed with yeast forms of the fungus (FIG. 28C). As with the flow cytometry analyses, the positive reaction of immune serum compared favorably with reactivity of MAb B6.1, which is specific for the glycan epitope [26]. Moreover, essentially the same pattern of C. albicans fluorescence was observed with immune serum from mice vaccinated with β-(Man)$_3$-Fba-TT alone, or when mixed with alum/MPL. No reactivity with the fungus was observed upon testing of serum from mice given adjuvant only or pooled serum from untreated normal mice. In addition to these findings, serum from mice immunized with the β-(Man)$_3$-Fba-TT conjugate reacted similarly with another C. albicans isolate (strain SC5314) (data not shown).

To summarize the above, the vaccine effectiveness has been shown to include C57BL/6 mice, which are more prone to Th1 responses and more resistant to disseminated candidiasis as compared to the BALB/c mice. By the same DC/CFA-based immunization protocols that favored production of protective antibody, the β-(Man)$_3$-Fba conjugate induced a similar level of protection in C57BL/6 mice as found for BALB/c animals. Furthermore, protection was observed regardless of the challenge strain of C. albicans. As with the BALB/c mice, passive transfer of antibodies against the two fungal epitopes to C57BL/6 naïve mice protected these animals against disseminated candidiasis.

To increase the immunogenicity of the β-(Man)$_3$-Fba conjugate when using an acceptable immunization approach for human use, the effects of coupling the conjugate to tetanus toxoid (TT) was tested, and the new glycopeptide vaccine conjugate, β-(Man)$_3$-Fba-TT, proved to be highly immunogenic as it induced robust antibody responses when administered with either alum or MPL as adjuvants. Moreover, prior to the second booster dose, an isotype switch occurred from IgM to IgG antibodies against for both the β-(Man)$_3$ and Fba peptide epitopes. This result indicated a memory cell response and, a vaccine that could induce long-term immunity. Most importantly, the β-(Man)$_3$-Fba-TT conjugate administered with either alum or MPL induced protection against disseminated candidiasis on a par with the high level of protection observed with the original DC/CFA immunization approach [7].

β-(Man)$_3$-Fba-TT was also administered alone and compared to administration of the conjugate as either a mixture made with alum or MPL. Mice that received the β-(Man)$_3$-Fba-TT conjugate prepared in either adjuvant responded as expected by making robust antibody responses. Surprisingly, mice that received the β-(Man)$_3$-Fba-TT without any adjuvant also responded well. All three groups of vaccinated mice showed a high level of protection against a lethal challenge with *C. albicans* as evidenced by significantly increased survival times and reduced or non-detectable kidney fungal burden at the time of sacrifice as compared to control groups that received only adjuvants or DPBS buffer prior to challenge. Furthermore, sera from mice immunized against the β-(Man)$_3$-Fba-TT conjugate transferred protection against disseminated candidiasis to naïve mice, whereas *C. albicans*-preabsorbed immune sera did not, which confirmed that induced antibodies were protective. These results demonstrate that the addition of the TT to the vaccine conjugate provided sufficient self-adjuvanting activity without the need for additional adjuvant, which supports the use of self-adjuvanting glycopeptide as vaccines.

The efficacy of the β-(Man)$_3$-Fba-TT conjugate vaccine in prolonging the survival of mice after a lethal challenge with *C. albicans* was also demonstrated in outbred mice. The β-(Man)$_3$-Fba-TT conjugate vaccine was immunogenic in Swiss Webster mice in the absence of an adjuvant, eliciting strong glycan- and peptide-specific antibodies and induced protection against candidiasis. Vaccine-mediated protection in this outbred mouse model was associated with a reduction in the levels of CFU in kidneys. Taken together, no evidence was found that protection had an MHC bias as evidenced by vaccine efficacy in BALB/c and C57BL/6 mice, and the vaccine effectiveness in outbred mice provides further support that this formulation can induce protection in humans as well. Without wishing to be found by this theory, we believe that establishment of active immunity when the host is immunologically normal will protect that host upon an immunocompromised event later.

Detection of specific antibodies induced by the β-(Man)$_3$-Fba-TT vaccine were determined by ELISA in which wells of the plate were coated with either β-(Man)$_3$ conjugated to bovine serum albumin or Fba peptide as a MAP conjugate to detect anti-glycan and peptide antibodies, respectively. The specificity of the response was confirmed to both the glycan and peptide epitopes by inhibition ELISA, in which free soluble β-(Man)$_3$ or Fba peptide inhibited the binding of antibodies in immune sera in a dose-dependent manner (data not shown). The binding of the specific antibodies to the actual fungal cell surface was confirmed by flow cytometric analyses, which demonstrated binding to *C. albicans* yeast forms, and by indirect immunofluorescence microscopy showing antibody reactivity with yeast and hyphal forms.

One advantage of keeping the glycan as part of the vaccine is that, although the Fba peptide is unique to *C. albicans* (except for the modified Fba reported above), responses against the β-(Man)$_3$ would be expected to protect against infection with a variety of other clinically important *Candida* species, including *C. tropicalis* [25], *C. lusitaniae* [59], *C. guilliermondii* [60] and the majority of *C. glabrata* strains [61].

Example 21

Synthesis of β-Man Trisaccharide-Fba and Fba Peptide Conjugated to Tetanus Toxoid The syntheses of the conjugates 6 and 7 are illustrated in FIGS. 29 and 30A-30E. The trisaccharide triethyleneglycol linker was synthesized as described for Compound 5 of S. Dziadek et al., "A novel linker methodology for the synthesis of tailored conjugate vaccines composed of complex carbohydrate antigens and specific T$_H$-cell peptide epitopes," *Eur. Chem.*, vol. 14, pp. 5908-5917 (2008)[62]. (For clarity, note that Dziadek et al.'s Compound 5 is designated instead as Compound 3 in the present disclosure; and that Compound 5 of the present disclosure differs from Dziadek et al.'s Compound 5.)

The Fba peptide was synthesized by first attaching Lys to a solid-phase peptide synthesis matrix. The α-amino group was protected with Fmoc, and the 6-amino group was protected with ivDde (1-(4,4-Dimethyl-2,6-dioxocyclo-hexylidene)-3-methylbutyl). Then a new linker was used to introduce a triethylene glycol spacer. The Fba peptide was then elaborated at the N terminus of this new linker. Prior to cleavage from the resin, the N terminus was either N-acetylated to provide a control reference peptide, or thiolproprionic acid was added to provide the thiol to link to Compound 3. For both the control peptide and the glycosylated peptide the ivDde group was removed, and the S-acetylthioglycolic acid was added to the ω-amino group of lysine. This provided a reactive C-terminal thiol group that could then conjugate either the Fba peptide 1 or the Man$_3$-Fba peptide 4 to tetanus toxoid. Tetanus toxoid was activated for conjugation by first introducing bromoacetate groups to accessible lysine residues in the carrier protein, and then reacting them with the tetanus toxoid peptide. Reacting Compounds 1 and 5 yielded the control conjugate 6. Reacting glycopeptide 4 with 5 yielded the vaccine conjugate 7. The final conjugates used for the immunization and challenge experiments were Compounds 6 and 7.

Reagents and General Methods

Acetic acid (AcOH) and dichloromethane (DCM) were obtained from Fisher Scientific. N,N'-dimethylformamide (DMF), N-methylpyrrolidone (NMP) and acetonitrile (CH$_3$CN) for HPLC were obtained from Calcdon Labs. Hydroxybenzotriazole (HOBt) and O-Benzotriazole-N,N,N', N'-tetramethyluronium hexafluorophosphate (HBTU) were obtained from Matrix Innovation. N,N'-diisopropylcarbodiimide (DIC), N,N-diisopropylethylamine (DIPEA), 4-(dimethylamino)pyridine (DMAP), trifluoroacetic acid (TFA), and triisopropyl silane (TIPS) were obtained from Sigma-Aldrich (Milwaukee, Wis.). Novasyn TGA resin and N$^\alpha$-Fmoc-amino derivatives were obtained from Nova Biochem.

The synthesis of the Fmoc-protected triethyleneglycol spacer followed the procedure as described in Keil, C. Claus, W. Dippold, H. Kunz, *Angew. Chem.* 2001, 113, 379; and *Angew. Chem. Int. Ed.* 2001, 40, 366 [66]. Deionized water was prepared with a Millipore ion-exchange device. Manual treatment of the solid support both before and after peptide synthesis was carried out with a spherical 250 mL peptide synthesis reactor with a female 45/50 fitting on top, and a 24/40 male vacuum fitting covered by a filter fit on the bottom (Schott, Germany). An IKA Vibrax VR vortexing apparatus was used to gently agitate resin suspensions during manual treatments. Fba was synthesized with an ABI 433A automated peptide synthesizer from Applied BioSystems.

A Waters HPLC system with Empower 2 software, Delta 600 solvent delivery system, and W2996 photodiode array detector was used for HPLC analyses and purifications. Phenomenex Luna C18 (2) 5 μm HPLC columns were used for both analytical and preparative separations. Analytical HPLC separations used a mobile phase flow rate of 1 mL min$^{-1}$ over a 4.6 mm×250 mm column. Preparative separations used a flow rate of 10 mL min$^{-1}$ over a 21.5 mm×250 mm column.

UV absorbance at 212 nm was used to determine elution of peptide-derived compounds for analytical and purification purposes. Matrix ionization laser desorption ionization (MALDI)—time of flight mass spectrometry (TOF MS) was used to identify UV-active HPLC fractions containing the desired peptides or glyco-peptide conjugates. The MALDI-TOF used a sinapinic acid matrix on a stainless steel plate, from which components ionized and desorbed for identification as protonated and sodium-adduct ions.

Fmoc-Lys(ivDde)-NovasynTG

Under an argon atmosphere, NovaSyn TGA resin (0.5 g, 90 μm, nominal capacity 0.26 mmol/g) was swelled in dry DCM (5 mL) in a Merrifield reactor. After two hours, excess DCM was removed by filtration, and dry DMF (2 mL) was added. The resin was then digested for 30 minutes. Running in parallel, 154 (7.7 eq) DIC were added dropwise under argon to a cold (0° C.) solution of 1.150 g (15.4 eq) Fmoc-Lys(ivDde)-OH in dry DCM (15 mL), and the mixture was stirred for 20 minutes. The mixture was concentrated under reduced pressure, and the resulting symmetrical anhydride was isolated as a white solid. Subsequently, dry DMF (2 mL) was added, and the resulting solution was transferred into the manual peptide reactor. Then 8 mg (0.5 eq) DMAP were added to catalyze coupling of the anhydride with the hydroxybenzyl functionality on the resin. After three hours, the resin was washed with five 10 mL portions of dry DMF, followed by five 10 mL portions of DCM. The resin loading was determined as previously described [54], (0.26 mmol/g, 100%). The resin was dried for 16 h under reduced pressure. The net weight of the remaining dried resin was 540 mg (94%).

H-YGKDVKDLFDYAQE(SEQ ID NO:1)-TEG-K(ivDde)-NovasynTG

The side chain-protected, resin-bound peptide was assembled with an ABI 433A automated synthesizer, starting with 540 mg Fmoc-Lys-(ivDde)-NovaSynTG, using a modified version of the standard Fast Moc 0.10 mmol protocol. In a Teflon reactor vessel mounted in a mechanical vortexing apparatus the amino acid residues were appended sequentially from the C to the N termini in 15 cycles. During each cycle, the antecedent N-terminal W-Fmoc group was removed from the peptide chain in a deprotection step employing a solution of piperidine (20%) in DMF, followed by a coupling step elongating the peptide chain by one aminoacyl residue. Unreacted peptide chains were acetylated in a capping step, and reagents and side-products were removed in a washing step in preparation for the following cycle. The number of $N^{\alpha}$-Fmoc deprotection steps varied from cycle to cycle, depending on the detection of Fmoc-piperidine adduct in the effluent, following up to four initial treatments of the resin-bound peptide with 20% piperidine in NMP. The concentration of Fmoc-piperidine adduct formed after each treatment was measured with a Perkin-Elmer Series 200 UV detector using an aliquot of deprotection effluent, diluted in methanol. Following the second and third treatments, measurement of a signal weaker than 4.5% of that measured after the first treatment indicated completion and automatically concluded deprotection for the cycle. If the third treatment did not meet this condition, then the synthesizer performed additional treatments of 8 minutes each until a signal less than or equal to 300 units was measured.

Next, 1 mmol of the corresponding $N^{\alpha}$-Fmoc amino acid derivative held in a sealed Teflon cartridge was dissolved in 3 mL NMP. Then 0.9 mmol HBTU was added to the cartridge to produce the corresponding aminoacyl HOBt ester in the presence of 1 mmol HOBt and 2 mmol DIPEA. Nitrogen gas pressure transferred the active ester from the cartridge to the resin, and mechanical vortexing of the resin in its reactor vessel accelerated permeation of the solid support to promote rapid reaction. Treatment with a capping solution of 0.5M acetic anhydride, 0.014M HOBt, and 0.129M DIPEA was used to truncate unreacted peptide chains and prevent synthesis of deletion sequences. The synthesis was completed by a final cycle in which the $N^{\alpha}$-Fmoc group was removed by the previously described deprotection step, and the resin-bound peptide was thoroughly washed with NMP and then DCM. In the manual peptide reactor, the resin was treated 5 times with 10 mL DCM and 5 times with 10 mL methanol, and subsequently dried under vacuum. The mass of resin and resin-bound protected peptide was 708 mg (80% yield by crude mass).

AcYGKDVKDLFDYAQE(SEQ ID NO:1)-TEG-K(SATA)-OH (Compound 1)

Dry, side-chain-protected, peptide-bearing resin (320 mg, 44 mmol) H-YGKDVKDLFDYAQE (SEQ ID NO:1)-TEG-K(ivDde)-NovasynTG was swirled gently with 5 mL dry DCM in a manual peptide reactor. Then 120 mL pyridine (1.5 mmol, 34 eq) and 60 μL $Ac_2O$ (636 mmol, 14 eq) were added to acetylate the N-terminal amine while the mixture was stirred for two hours. Subsequently, the liquid phase was drained from the reactor, and the resin was washed with three 10 mL portions of DCM. The ivDde protecting group of the C-terminal lysine residue was removed by three treatments with 3.3 mL 5% (w/v) hydrazine in DMF for five minutes each. After washing with five aliquots of 10 mL DMF, 40 mg (173 mmol, 3.9 eq) N-hydroxysuccinimidyl S-acetyl-thioacetate (SATA) dissolved in 2 mL dry DMF and 15 μL (86 mmol, 2.0 eq) DIPEA were added, and the resin was shaken for one hour. The solution was drained from the reaction vessel, and the resin was washed with three 5 mL aliquots of DMF followed by three 5 mL aliquots of DCM. The peptide was cleaved from the solid support with simultaneous removal of the side-chain-protecting groups by treating the resin with a mixture of 7 mL TFA: 450 μL $H_2O$: 450 μL TIS for two hours. The solution was drained from the reactor into a 100 mL round-bottom flask, and the resin was rinsed with two 10 mL portions of TFA. A rotary evaporator removed most of the TFA from the crude peptide solution. Three 5 mL portions of toluene were added to the flask to assist in removing volatile compounds under reduced pressure at room temperature.

The peptide was precipitated by adding 15 mL of diethyl ether at 0° C. The precipitated peptide appeared as a white solid that adhered to the flask. The supernatant was removed with a Pasteur pipette, and the peptide was washed twice with 15 mL aliquots of diethyl ether to remove impurities. The crude peptide was dried thoroughly overnight under reduced pressure. The final mass of crude peptide was 54 mg. The crude peptide was then dissolved in a solution of 75% $CH_3CN$ and 25% $H_2O$ with 0.1% TFA, and purified by reverse-phase chromatography under a gradient from 75:25 to 60:40 $H_2O$:$CH_3CN$ with a modifier of 0.1% TFA over 50 minutes. The eluent was collected from 25.8 to 27.2 minutes, flash-frozen, and lyophilized to give Compound 1 as a white solid, mass 26 mg (12 μmol, 27.1%).

$HS(CH_2)_2CO$-YGKDVKDLFDYAQE(SEQ ID NO:1)-TEG-K(SATA)-OH (Compound 2)

In the 433A synthesizer, 335 mg (46 μmol) of resin-bound, side-chain-protected peptide H-YGKDVKDLFDYAQE (SEQ ID NO:1)-TEG-K(ivDde)-NovasynTG was swelled with DCM and then NMP. Subsequently, the free amino terminus was acylated with 1 mmol 3-(S-trityl)-thiopropanoic acid, activated by an HBTU solution following standard protocols for Fmoc-amino acids, to give the protected, resin-bound pentadecapeptide. Washing with DMF and then DCM removed reaction side-products. The peptide resin was then transferred to the manual peptide reactor. Three treatments with 3.3 mL 5% (w/v) hydrazine in DMF for five minutes each were used to remove the ivDde protecting group from the C-terminal lysine residue. The resin was washed with five aliquots of 10 mL DMF. Then 44 mg (190 μmol, 4.1 eq) N-hydroxysuccinimidyl S-acetyl-thioacetate (SATA) dissolved in 2 mL dry DMF and 15 μL (86 mmol, 1.9 eq) DIPEA were added, and the resin was shaken for one hour. The solution was drained from the reactor, and the resin was washed with three 5 mL aliquots of DMF followed by three 5 mL aliquots of DCM. The solid support was treated for two hours with a mixture of 8.3 mL TFA: 420 μL $H_2O$: 420 μL TIS: 830 μL EDT to remove the side-chain-protecting groups and to cleave the peptide from the resin. The solution was drained from the reactor into a 100 mL round-bottom flask, and the resin was rinsed with two 10 mL portions of TFA. A rotary evaporator was used to remove most of the TFA from the crude peptide solution. Three 5 mL portions of toluene were added to the flask to assist with the removal of volatile compounds under reduced pressure at room temperature. The peptide was precipitated by adding 15 mL of diethyl ether at 0° C. The peptide precipitate was a white solid that adhered to the flask. The supernatant was removed with a Pasteur pipette, and the peptide was washed twice with 15 mL aliquots of diethyl ether to remove impurities. The crude peptide was dried overnight under reduced pressure. The final mass of crude peptide was 40 mg (18.3 mmol, 41%). The crude peptide was dissolved in a solution of 75% $CH_3CN$ and 25% $H_2O$ with 0.1% TFA, and purified by reverse-phase chromatography under a gradient from 75:25 to 65:35 $H_2O$:$CH_3CN$ with a modifier of 0.1% TFA over 50 minutes. The eluent was collected from 34.0 to 35.2 minutes, flash-frozen, and lyophilized to give Compound 2 as a white solid, mass 24 mg (11 μmol, 24%).

βMan$_3$-S(CH$_2$)$_2$CO-YGKDVKDLFDYAQE(SEQ ID NO:1)-TEG-K(SATA)-OH (Compound 4)

A mixture of 1 mL of 50 mM Tris HCl buffer (pH 8.9) and 250 μL methanol was degassed by sonication under reduced pressure for 10 minutes, followed by sparging with argon. The degassed buffer solution was used to dissolve 2.7 mg (3.1 mop β-mannoside acrylate (Compound 3) and 8.7 mg (3.9 mmol, 1.3 eq) HS(CH$_2$)$_2$CO-YGKDVKDLFDYAQE (SEQ ID NO:1)-TEG-K(SATA)-OH (Compound 2) in a 2 mL microcentrifuge vial. The mixture was centrifuged briefly to assess whether any material remained undissolved, and was then placed in the dark for two hours to react. The mixture was filtered with a 10 mm, 0.2 μm PVDF filter to remove undissolved materials, and then the mixture was immediately purified by HPLC using a gradient from 85:15 to 65:35 $H_2O$: $CH_3CN$ containing 0.02% acetic acid. The glycol-peptide conjugate eluted from 50.5-52.3 minutes. This material was collected, flash-frozen, and lyophilized, yielding 6.6 mg (2.1 μmol, 69%) of the title Compound 4 as a white solid.

Conjugation of the Peptides AcYGKDVKDLFDYAQE(SEQ ID NO:1)-TEG-K(SATA)-OH and βMan$_3$-S(CH$_2$)$_2$CO-YGKDVKDLFDYAQE(SEQ ID NO: 1)-TEG-K(SATA)-OH to Tetanus Toxoid To monomeric tetanus toxoid (10 mg) in PBS (1.3 mL, pH 7.4) in a 4 mL glass Kimbal vial with a magnetic stirring bar, 2 mg of bromoacetic acid NHS ester was added. The vial was wrapped with aluminum foil and left on a magnetic stirrer for 3 hours. Bromoacetylated tetanus toxoid (Compound 5) was purified in PBS on a calibrated G 25 column. Collected fractions were concentrated in an Amicon Millipore centrifugal filter unit (10 kDa) to ~0.5 mL, and the solution was transferred to a 2 mL Eppendorf tube. Fba peptide (Compound 1) (6.5 mg) was dissolved in 0.1M PBS (0.5 mL, pH 7.4) containing 0.5 M hydroxylamine and 25 mM EDTA, and the solution was added to the bromoacetylated tetanus toxoid, Compound 5. The tube was wrapped with aluminum foil and left for two days at 37° C. on an inverting mixer. The conjugate was then purified on a Superdex S200 column (2×100 cm) equilibrated with 0.1M Tris HCl (pH 7.5). Fractions corresponding to the conjugate were collected, dialyzed against PBS, and concentrated.

The glycopeptide βMan$_3$-Fba Compound 4 (3.9 mg) was conjugated to the bromoacetylated tetanus toxoid Compound 5 (4.4 mg) using the same procedure.

Before delivery, each conjugate was desalted on a G-25 column, equilibrated with water, and lyophilized.

The incorporation of peptide to give the Fba-tetanus toxoid conjugate Compound 6 was estimated by MALDI to be an average of 11.7, and an incorporation average of 5.5 was determined for the βMan$_3$-Fba-tetanus toxoid conjugate Compound 7. I.e., the average number of peptide or glycopeptide molecules bound per molecule of tetanus toxoid was determined to be 11.7 (most values within the range of 11-12) or 5.5 (most values within the range of 5-6).

REFERENCE LIST

1. Antonsson A and Johansson P. J. H. 2001. Binding of human and animal immunoglobulins to the IgG Fc receptor induced by human cytomegalovirus. Journal of general virology 82:1137-1145.
2. Ashman, R. B. 1987. Mouse candidiasis. II. Host responses are T-cell dependent and regulated by genes in the major histocompatibility complex. Immunogenetics 25:200-203.
3. Ashman, R. B. 1990. Murine candidiasis: Susceptibility is associated with the induction of T cell-mediated, strain-specific autoreactivity. Immunol. Cell Biol. 68:179-185.
4. Ashman, R. B. and J. M. Papadimitriou. 1987. Murine candidiasis. Pathogenesis and host responses in genetically distinct inbred mice. Immunol. Cell Biol. 65:163-171.
5. Brena, S., M. J. Omaetxebarria, N. Elguezabal, J. Cabezas, M. D. Moragues, and J. Pontón. 2007. Fungicidal monoclonal antibody C7 binds to *Candida albicans*. Infect. Immun. 75:3680-3682.
6. Brett S. J. and Butler R. 1988. Macrophage activity in resistant and susceptible mouse strains infected with *Mycobacterium* lepraemurium. Immunol. 63:701-706.
7. Cabezas J, Albaina O, Montañez D, Sevilla M J, Moragues M D, and Pontón J. 2010. Potential of anti-*Candida* antibodies in immunoprophylaxis. Immunotherapy 2:171-183.
8. Casadevall, A., E. Dadachova, and L.-A. Pirofski. 2004. Passive antibody therapy for infectious diseases. Nature Reviews 2:695-703.
9. Casadevall, A. and L.-A. Pirofski. 2007. Antibody-mediated protection through cross-reactivity introduces a fungal heresy into immunological dogma. Infect. Immun. 75:5074-5078.
10. Cassone, A., F. De Bernardis, and A. Torosantucci. 2005. An outline of the role of anti-*Candida* antibodies within the context of passive immunization and protection from candidiasis. Curr. Mol. Med. 5:377-382.
11. Clancy, C. J., M. L. Nguyen, S. Cheng, H. Huang, G. Fan, R. A. Jaber, J. R. Wingard, C. Cline, and M. H. Nguyen. 2008. Immunoglobulin G responses to a panel of *Candida albicans* antigens as accurate and early markers for the presence of systemic candidiasis. J. Clin. Microbiol. 46:1647-1654.

12. Crowe J. D., Sievwright I. K., Auld G. C., Moore N. R., Gow. N. A., and Booth N. A. 2003. *Candida albicans* binds human plasminogen: identification of eight plasminogen-binding proteins. Mol. Microbiol. 47:1637-1651.
13. Cutler, J. E. 2005. Defining criteria for anti-mannan antibodies to protect against candidiasis. Curr. Mol. Med. 5:383-392.
14. Cutler, J. E., D. L. Brawner, K. C. Hazen, and M. A. Jutila. 1990. Characteristics of *Candida albicans* adherence to mouse tissue. Infect. Immun. 58:1902-1908.
15. Cutler, J. E., G. S. Deepe, Jr., and B. S. Klein. 2007. Advances in combating fungal diseases: Vaccines on the threshold. Nat. Rev. Microbiol. 5:13-28.
16. Cutler, J. E., T. Kanbe, R. K. Li, Q. Qian, Y. Han, and M. Riesselman. 1995. Mannan adhesins of *Candida albicans*: Characterization and pathogenetic implications. Jpn. J. Med. Mycol. 36:193-201.
17. De Bernardis, F., M. Boccanera, D. Adriani, E. Spreghini, G. Santoni, and A. Cassone. 1997. Protective role of anti-mannan and anti-aspartyl proteinase antibodies in an experimental model of *Candida albicans* vaginitis in rats. Infect. Immun. 65:3399-3405.
18. Eggimann, P., J. Garbino, and D. Pittet. 2003. Epidemiology of *Candida* species infections in critically ill non-immunosuppressed patients. Lancet Infect. Dis. 3:685-702.
19. Elguezabal, N., J. L. Maza, M. D. Moragues, and J. Pontón. 2009. Monoclonal antibody-mediated inhibition of adhesion of *Candida albicans* and *Candida dubliniensis* to human epithelial cells. Eur J Oral Sci 117:474-478.
20. Fernandez-Arenas, E., G. Molero, C. Nombela, R. Deiz-Orejas, and C. Gil. 2004. Contribution of the antibodies response induced by a low virulent *Candida albicans* strain in protection against systemic candidiasis. Proteomics 4:1204-1215.
21. Fernandez-Arenas, E., G. Molero, C. Nombela, R. Diez-Orejas, and C. Gil. 2004. Low virulent strains of *Candida albicans*: unravelling the antigens for a future vaccine. Proteomics 4:3007-3020.
22. Grappel, S. F. and R. A. Calderone. 1976. Effect of antibodies on the respiration and morphology of *Candida albicans*. S. Afr. Med. J. 14:51-60.
23. Guttman, A. and T. Pritchett. 1995. Capillary gel electrophoresis separation of high-mannose type oligosaccharides derivatized by 1-aminopyrene-3,6,8-trisulfonic acid. Electrophoresis 16:1906-1911.
24. Han, Y. 2010. Efficacy of combination immunotherapy of IgM MAb B6.1 and amphotericin B against disseminated candidiasis. Int. Immunopharmacol. 10:1526-1531.
25. Han, Y. and J. E. Cutler. 1995. Antibody response that protects against disseminated candidiasis. Infect. Immun. 63:2714-2719.
26. Han, Y., T. Kanbe, R. Chemiak, and J. E. Cutler. 1997. Biochemical characterization of *Candida albicans* epitopes that can elicit protective and nonprotective antibodies. Infect. Immun. 65:4100-4107.
27. Han, Y., T. R. Kozel, M. X. Zhang, R. S. MacGill, M. C. Carroll, and J. E. Cutler. 2001. Complement is essential for protection by an IgM and an IgG3 monoclonal antibody against experimental hematogenously disseminated candidiasis. J. Immunol. 167:1550-1557.
28. Han, Y., R. P. Morrison, and J. E. Cutler. 1998. A vaccine and monoclonal antibodies that enhance mouse resistance to *Candida albicans* vaginal infection. Infect. Immun. 66:5771-5776.
29. Han, Y., M. H. Riesselman, and J. E. Cutler. 2000. Protection against candidiasis by an immunoglobulin G3 (IgG3) monoclonal antibody specific for the same mannotriose as an IgM protective antibody. Infect. Immun. 68:1649-1654.
30. Han, Y., M. A. Ulrich, and J. E. Cutler. 1999. *Candida albicans* mannan extract-protein conjugates induce a protective immune response against experimental candidiasis. J. Infect. Dis. 179:1477-1484.
31. Hobson, R. P., C. A. Munro, S. Bates, D. M. MacCallum, J. E. Cutler, S. E. M. Heinsbroek, G. D. Brown, F. C. Odds, and N. A. R. Gow. 2004. Loss of cell wall mannosylphosphate in *Candida albicans* does not influence macrophage recognition. J. Biol. Chem. 279:39628-39635.
32. Horn, D. L., D. Neofytos, E. J. Anaissie, J. A. Fishman, W. J. Steinbach, A. J. Olyaei, K. A. Marr, M. A. Pfaller, C. H. Chang, and K. M. Webster. 2009. Epidemiology and outcomes of candidemia in 2019 patients: data from the prospective antifungal therapy alliance registry. Clin. Infect. Dis. 48:1695-1703.
33. Hsu, F. C., P. C. Lin, C. Y. Chi, M. W. Ho, and J. H. Wang. 2009. Prognostic factors for patients with culture-positive *Candida* infection undergoing abdominal surgery. J. Microbiol. Immunol. Infect. 42:378-384.
34. Jarvis, W. R. and W. J. Martone. 1992. Predominant pathogens in hospital infections. J. Antimicrob. Chemother. 29:19-24.
35. JAX Mice. H-2 haplotypes of mice from Jackson Laboratory colonies. 1988. JAX Mice Literature, JAX Lab. Ref Type: Pamphlet
36. Kavishwar, A. and P. K. Shukla. 2006. Candidacidal activity of a monoclonal antibody that binds with glycosyl moieties of proteins of *Candida albicans*. Med. Mycol. 44:159-167.
37. Kobayashi, H., P. Giummelly, S. Takahashi, M. Ishida, J. Sato, M. Takaku, Y. Nishidate, S, Nobuyuki, Y. Okawa, and S. Suzuki. 1991. *Candida albicans* serotype A strains grow in yeast extract-added Sabouraud liquid medium at pH 2.0, elaborating mannans without b-1,2 linkage and phosphate group. Biochem. Biophys. Res. Commun. 175:1003-1009.
38. Magliani, W., S. Conti, L. Giovati, D. Maffei, and L. Polonelli. 2008. Anti-beta-glucan-like immunoprotective candidacidal antiidiotypic antibodies. Front Biosci 13:6920-6937.
39. Marsh J J and Lebherz H G. 1992. Fructose-bisphosphate aldolases: an evolutionary history. Trends Biochem. Sci. 17:110-113.
40. Matthews, R. C., G. Rigg, S. Hodgetts, T. Carter, C. Chapman, C. Gregory, C. Illidge, and J. Burnie. 2003. Preclinical assessment of the efficacy of mycograb, a human recombinant antibody against fungal HSP90. Antimicrob. Agents Chemother. 47:2208-2216.
41. Mochon, A. B. and J. E. Cutler. 2005. Is a vaccine needed against *Candida albicans*? Med. Mycol. 43:97-115.
42. Moragues, M. D., M. J. Omaetxebarria, N. Elguezabal, M. J. Sevilla, S. Conti, L. Polonelli, and J. Ponton. 2003. A monoclonal antibody directed against a *Candida albicans* cell wall mannoprotein exerts three anti-*C. albicans* activities. Infect. Immun. 71:5273-5279.
43. Nooney, L. M., R. C. Matthews, and J. P. Burnie. 2005. Evaluation of Mycograb, amphotericin B, caspofungin, and fluconazole in combination against *Cryptococcus neoformans* by checkerboard and time-kill methodologies. Diagn. Microbiol. Infect. Dis. 51:19-29.

44. Pachl, J., P. Svoboda, F. Jacobs, K. Vandewoude, B. van der Hoven, P. Spronk, G. Masterson, M. Malbrain, M. Aoun, J. Garbino, J. Takala, L. Drgona, J. Burnie, R. Matthews, and Mycograb Invasive Candidiasis Study Group. 2006. A randomized, blinded, multicenter trial of lipid-associated amphotericin B alone versus in combination with an antibody-based inhibitor of heat shock protein 90 in patients with invasive candidiasis. Clin. Infect. Dis. 42:1404-1413.

45. Pincus, S. H., A. O, Shigeoka, A. A. Moe, L. P. Ewing, and H. R. Hill. 1988. Protective efficacy of IgM monoclonal antibodies in experimental group B streptococcal infection is a function of antibody. J. Immunol. 140:2779-2785.

46. Pitarch, A., J. Abian, M. Carrascal, M. Sanchez, C. Nombela, and C. Gil. 2004. Proteomics-based identification of novel *Candida albicans* antigens for diagnosis of systemic candidiasis in patients with underlying hematological malignancies. Proteomics 4:3084-3106.

47. Richards, M. J., J. R. Edwards, D. H. Culver, R. P. Gaynes, and National Nosocomial Infections Surveillance System. 1998. Nosocomial infections in coronary care units in the United States. Am. J. Cardiol 82:789-793.

48. Rodaki A, Young T, and Brown A J. 2006. Effects of depleting the essential central metabolic enzyme fructose-1,6-bisphosphate aldolase on the growth and viability of *Candida albicans*: implications for antifungal drug target discovery. Eukaryot Cell 5:1371-1377.

49. Son, Y.-I., S. Egawa, T. Tatsumi, R. E. Redlinger, P. Kalinski, and T. Kanto. 2002. A novel bulk-culture method for generating mature dendritic cells from mouse bone marrow cells. Immunol. Meth. 262:145-157.

50. Torosantucci, A., C. Bromuro, P. Chiani, F. De Bernardis, F. Berti, C. Galli, F. Norelli, C. Bellucci, L. Polonelli, P. Costantino, R. Rappuoli, and A. Cassone. 2005. A novel glyco-conjugate vaccine against fungal pathogens. J. Exp. Med 202:597-606.

51. Torosantucci, A., P. Chiani, C. Bromuro, F. De Bernardis, A. S. Palma, Y. Liu, G. Mignogna, B. Maras, M. Colone, A. Stringaro, S. Zamboni, T. Feizi, and A. Cassone. 2009. Protection by anti-beta-glucan antibodies is associated with restricted beta-1,3 glucan binding specificity and inhibition of fungal growth and adherence. PLoS One 4:e5392.

52. Xin, H. and J. E. Cutler. 2006. Hybricoma passage in vitro may result in reduced ability of antimannan antibody to protect against disseminated candidiasis. Infect. Immun. 74:4310-4321.

53. Xin, H., S. Dziadek, D. R. Bundle, and J. E. Cutler. 2008. Synthetic glycopeptide vaccines combining b-mannan and peptide epitopes induce protection against candidiasis. Proc. Natl. Acad. Sci. USA 105:13526-13531.

54. Fmoc Solid Phase Peptide Synthesis: A Practical Approach, Chan W C and White P D (Eds), Oxford University Press, Oxford, Copyright 2000, reprinted 2004, p. 63.

55. Yang, Q., L. Wang, D. N. Lu, R. J. Gao, J. N. Song, P. Y. Hua, and D. W. Yuan. 2005. Prophylactic vaccination with phage-displayed epitope of *C. albicans* elicits protective immune responses against systemic candidiasis in C57B1/6 mice. Vaccine 23:4088-4096.

56. Bromuro C, Romano M, Chiani P, Berti F, Tontini M, Proietti C, Mori E, Torosantucci A, Costantino P, Rappuoli R, Cassone A (2010) Beta-glucan-CRM 197 conjugates as candidates antifungal vaccines. Vaccine 28: 2615-2623.

57. Wu X, Bundle D R (2005) Synthesis of glycoconjugate vaccines for *Candida albicans* using novel linker methodology. J Org Chem 70: 7381-7388.

58. Wu X, Lipinski T, Carrel F R, Bailey J J, Bundle D R (2007) Synthesis and immunochemical studies on a *Candida albicans* cluster glycoconjugate vaccine. Org Biomol Chem 5: 3477-3485.

59. Shibata N, Kobayashi H, Okawa Y, Suzuki S (2003) Existence of novel b-1,2 linkage-containing side chain in the mannan of *Candida* lusitaniae, antigenically related to *Candida albicans*. Eur J Biochem 270: 2565-2575.

60. Suzuki A, Shibata N, Suzuki M, Saitoh F, Oyamada H, Kobayashi H, Suzuki S, Okawa Y (1997) Characterization of b-1,2-mannosyltransferase in *Candida* guilliermondii and its utilization in the synthesis of novel oligosaccharides. J Biol Chem 272: 16822-16828.

61. Goins T, Cutler J E (2000) Relative abundance of oligosaccharides in *Candida* species as determined by fluorophore-assisted carbohydrate electrophoresis. J Clin Microbiol 38: 2862-2869.

62. Dziadek S, Jacques S, Bundle D R (2008) A novel linker methodology for the synthesis of tailored conjugate vaccines composed of complex carbohydrate antigens and specific TH-cell peptide epitopes. Chemistry 14: 5908-5917.

63. Jacob, C. O., Sela M, Amon R (1983) Antibodies against synthetic peptides of the B subunit of *cholera* toxin: cross-reaction and neutralization of the toxin. PNAS 80: 7611-7615.

64. Jacob, C O, Sela, M, Pines M, Hurwitz S, Amon R (1984) Both *cholera* toxin-induced adenylate cyclase activation and *cholera* toxin biological activity are inhibited by antibodies against related synthetic peptides. PNAS 81:7893-7896.

65. Brandt E R, Teh T, Reif W A, Hobb R I, Good M F (2000) Protective and nonprotective epitopes from amino termini of M proteins from Australian aboriginal isolates and reference strains of Group A streptococci. Infection and Immunity 68(12):6587-6594.

66. Keil S, Claus C, Dippold W, Kunz H (2001) Towards the development of antitumor vaccines: a synthetic conjugate of a tumor-associated MUCI glycopeptide antigen and a tetanus toxin epitope. Angew. Chem. Int. Ed., 40:366-369.

The complete disclosures of all references cited in this application are hereby incorporated by reference. Specifically incorporated by reference are the following: (1) H. Xin, J. Cartmell, D. R. Bundle, and J. E. Culter, "New strategies to present an anti-Candidiasis synthetic glycopeptides vaccine acceptable for human use," a poster presented at the Gordon Conference, January 2011, in Galveston, Tex.; (2) H. Xin, J. Cartmell, D. R. Bundle, and J. E. Cutler, "Anti-candidasis synthetic glycopeptides vaccine with adjuvant can induce protective immunity in mice," an abstract for the 111th General Meeting of the American Society of Microbiology, New Orleans, La., May 20-24, 2011; (3) H. Xin et al., "Vaccine and monoclonal antibody that enhance mouse resistance to Candidiasis," Clinical and Vaccine Immunology, vol. 18, pp. 1656-1667 (2011; epub Aug. 10, 2011); and H. Xin et al., "Self-adjuvanting glycopeptide conjugate vaccine against disseminated Candidiasis, accepted by PLoS, 2012. In the event of an otherwise irreconcilable conflict, however, the present specification shall control.

What is claimed:

1. A composition comprising a first monoclonal antibody and a second monoclonal antibody; wherein said first and second monoclonal antibodies differ; wherein said first monoclonal antibody binds to *Candida* cell wall peptide SEQ ID NO: 1; and wherein said second monoclonal antibody binds to a *Candida* cell wall peptide selected from the group consisting of SEQ ID NOS: 2, 3, and 8-20.

2. The composition of claim 1, wherein said second monoclonal antibody binds SEQ ID NO:2.

3. The composition of claim 1, further comprising one or more antifungal compounds are selected from the group consisting of a polyene antifungal, an azole, an allylamine, an echinocandin, and a monoclonal antibody specific for β-(1,2)-mannotriose.

4. A method of passive immunization against candidiasis, comprising administering to a mammal in need thereof the composition of claim 1.

5. A method of passive immunization against candidiasis, comprising administering to a mammal in need thereof the composition of claim 2.

6. A method of passive immunization against candidiasis, comprising administering to a mammal in need thereof the composition of claim 3.

* * * * *